United States Patent
Li et al.

(10) Patent No.: US 11,596,653 B2
(45) Date of Patent: Mar. 7, 2023

(54) COMPOSITIONS AND METHODS OF CELLULAR IMMUNOTHERAPY

(71) Applicant: CRAGE medical Co., Limited, Hong Kong (CN)

(72) Inventors: Zonghai Li, Shanghai (CN); Huiping Gao, Shanghai (CN); Peng Wang, Shanghai (CN); Hua Jiang, Shanghai (CN); Huamao Wang, Shanghai (CN)

(73) Assignee: CRAGE MEDICAL CO., LIMITED, Hong Kong (CN)

( * ) Notice: Subject to any disclaimer, the term of this patent is extended or adjusted under 35 U.S.C. 154(b) by 931 days.

(21) Appl. No.: 16/164,995

(22) Filed: Oct. 19, 2018

(65) Prior Publication Data

US 2019/0151362 A1    May 23, 2019

Related U.S. Application Data

(63) Continuation of application No. PCT/CN2017/081446, filed on Apr. 21, 2017.

(30) Foreign Application Priority Data

Apr. 22, 2016 (CN) .......................... 201610256568.9

(51) Int. Cl.
| | | |
|---|---|---|
| *A61K 35/17* | (2015.01) | |
| *A61P 35/00* | (2006.01) | |
| *C07K 14/705* | (2006.01) | |
| *A61K 48/00* | (2006.01) | |
| *C07K 16/30* | (2006.01) | |
| *C07K 14/725* | (2006.01) | |
| *A61K 9/00* | (2006.01) | |
| *A61K 31/519* | (2006.01) | |
| *A61K 31/664* | (2006.01) | |
| *A61K 31/7048* | (2006.01) | |
| *A61K 31/7076* | (2006.01) | |
| *A61K 38/20* | (2006.01) | |

(52) U.S. Cl.
CPC ............ *A61K 35/17* (2013.01); *A61K 9/0019* (2013.01); *A61K 31/519* (2013.01); *A61K 31/664* (2013.01); *A61K 31/7048* (2013.01); *A61K 31/7076* (2013.01); *A61K 38/202* (2013.01); *A61K 38/204* (2013.01); *A61K 38/2013* (2013.01); *A61K 38/2073* (2013.01); *A61K 48/00* (2013.01); *A61P 35/00* (2018.01); *C07K 14/7051* (2013.01); *C07K 14/70517* (2013.01); *C07K 16/303* (2013.01); *A01K 2207/12* (2013.01); *A01K 2227/105* (2013.01); *C07K 2317/24* (2013.01); *C07K 2317/622* (2013.01); *C07K 2319/02* (2013.01); *C07K 2319/03* (2013.01); *C07K 2319/33* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 7,919,086 B2 | 4/2011 | Nakano et al. | |
| 10,731,127 B2 | 8/2020 | Li et al. | |
| 2007/0190599 A1 | 8/2007 | Nakano et al. | |
| 2010/0247579 A1* | 9/2010 | Shiku | A61P 35/04 424/277.1 |
| 2014/0170114 A1 | 6/2014 | Kaplan | |
| 2015/0093822 A1 | 4/2015 | June et al. | |
| 2016/0215261 A1 | 7/2016 | Li et al. | |
| 2017/0204177 A1 | 7/2017 | Wang et al. | |
| 2017/0369561 A1* | 12/2017 | Kaplan | C07K 16/18 |
| 2018/0201902 A1 | 7/2018 | Wang et al. | |
| 2019/0262397 A1* | 8/2019 | Connolly | A61P 31/00 |
| 2019/0314369 A1* | 10/2019 | Lannutti | A61K 9/2027 |

FOREIGN PATENT DOCUMENTS

| | | |
|---|---|---|
| CN | 101186650 A | 5/2008 |
| CN | 101633693 A | 1/2010 |
| CN | 102702353 A | 10/2012 |
| CN | 104140974 A | 11/2014 |
| CN | 105246504 A | 1/2016 |
| CN | 105331585 A | 2/2016 |
| EP | 2995682 A1 | 3/2016 |
| JP | 2009091348 A | 4/2009 |
| KR | 20150042784 A | 4/2015 |
| KR | 20160003287 A | 1/2016 |
| WO | WO-2008045437 A2 | 4/2008 |
| WO | WO-2010025177 A1 | 3/2010 |
| WO | WO-2012145469 A1 | 10/2012 |
| WO | WO-2012156747 A1 | 11/2012 |

(Continued)

OTHER PUBLICATIONS

Abou-Alfa, et al. Randomized phase II placebo controlled study of codrituzumab in previously treated patients with advanced hepatocellular carcinoma. J Hepatol. Aug. 2016;65(2):289-95. doi: 10.1016/j.jhep.2016.04.004. Epub Apr. 13, 2016.

Ali, et al. Remissions of Multiple Myeloma during a First-in-Humans Clinical Trial of T Cells Expressing an Anti-B-Cell Maturation Antigen Chimeric Antigen Receptor. Blood. Dec. 3, 2015. 126(23): LBA-1. doi: https://doi.org/10.1182/blood.V126.23.LBA-1.LBA-1 (3 pages).

An-Sheng Bai, et al. "Expression of Kinase Insert Domain-containing Receptor in Prostate Adenocarcinoma," National Journal of Andrology, vol. 13, No. 4, Apr. 2007, pp. 324-326 (English Abstract).

(Continued)

*Primary Examiner* — Michail A Belyavskyi
(74) *Attorney, Agent, or Firm* — Wilson Sonsini Goodrich & Rosati

(57) ABSTRACT

Disclosed herein are methods of treating a subject exhibiting a solid tumor that expresses Glypican-3 (GPC3). The methods typically utilize g GPC3 chimeric antigen receptor immunoresponsive cells to a subject in need thereof to effect killing of tumor cells.

29 Claims, 13 Drawing Sheets

Specification includes a Sequence Listing.

(56) References Cited

FOREIGN PATENT DOCUMENTS

| WO | WO-2013070468 A1 | 5/2013 |
|---|---|---|
| WO | WO-2014179759 A1 | 11/2014 |
| WO | WO-2014180306 A1 | 11/2014 |
| WO | WO-2014201021 A2 | 12/2014 |
| WO | WO-2015136001 A1 | 9/2015 |
| WO | WO-2015188141 A2 | 12/2015 |
| WO | WO-2016036973 A1 | 3/2016 |
| WO | WO-2016049459 A1 | 3/2016 |
| WO | WO-2018018958 A1 | 2/2018 |

OTHER PUBLICATIONS

Bot, et al. Cyclophosphamide and Fludarabine Conditioning Chemotherapy Induces a Key Homeostatic Cytokine Profile in Patients Prior to CAR T Cell Therapy. Blood. Dec. 3, 2015. 126(23): 4426. doi: https://doi.org/10.1182/blood.V126.23.4426.4426 (3 pages).
Carpenito et al. Control of large, established tumor xenografts with genetically retargeted human T cells containing CD28 and CD137 domains. PNAS USA 106(9):3360-3365 (2009).
European search report with written opinion dated Oct. 21, 2016 for EP Application No. 14794936.
Hartmann, et al., Clinical development of CAR T cells—challenges and opportunities in translating innovative treatment concepts, EMBO Molecular Medicine, 2017, 9(9):1183-1197.
Ho Mitchell, et al. "Giypican-3: A new target for cancer immunotherapy," European Journal of Cancer, 2011, No. 47, pp. 333-338.
Hui Liu, et al. Synthesis of full length recombinant chimeric receptor anti-erbB2 scFv-CD28-(and construction of its eukaryotic expression vector. Journal of Chinese PLA Postgraduate Medical School, vol. 31, No. 4, Apr. 2010, pp. 360-362, (English Abstract).
International Search Report dated Aug. 19, 2014 for Application No. PCT/CN2014/076913 filed dated May 6, 2014, 7 pages.
Li Yonghai, et al. Validation of glypican-3-specific scFv isolated from paired display/secretory yeast display library. BMC Biotechnology, vol. 12 (23):2012, 10 pages.
McGinley, et al. Lentiviral Vector Mediated modification of Mesenchymal Stem Celle & Enhanced Survival in Vitro Model of Ischaemia. Stem Cell Res & Therapy. 2:12:2011, pp. 1-12, doi:10.1186/scrt53.
Milone et al. Chimeric receptors containing CD137 signal transduction domains mediate enhanced survival of T cells and increased antileukemic efficacy in vivo. Mol Ther 17(8):1453-1464 (2009).
Notice of allowance dated Mar. 27, 2020 for U.S. Appl. No. 14/889,778.
Notice of allowance dated Aug. 3, 2018 for U.S. Appl. No. 14/889,778.
Office Action dated Aug. 15, 2017 for U.S. Appl. No. 14/889,778.
Office Action dated Dec. 27, 2017 for U.S. Appl. No. 14/889,778.
PWPT-GFP, plasmid #12255; www.addgene.org/12255/; last visited Aug. 8, 2017.
Sadelain et al. The basic principles of chimeric antigen receptor design. Cancer Discov. 3(4):388-98 (2013).
Tamada et al., Redirecting gene-modified T cells toward various cancer types using tagged antibodies, Clinical Cancer Research, vol. 18, No. 23 Dec. 1, 2012, pp. 6436-6445, e-pub Oct. 2, 2012.
Turtle, et al. Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. Dec. 3, 2015. 126(23): 184. doi: https://doi.org/10.1182/blood.V126.23.184.184 (4 pages).
Vu Sawada, et al. Phase I Trial of a Glypican-3-Derived Peptide Vaccine for Advanced Hepatocellular Carcinoma: Immunologic Evidence and Potential for Improving Overall Survival. Clinical Cancer Research, vol. 18, No. 13, Jul. 1, 2012, pp. 3686-3696.
Wang, et al., The status and development of tumor microenvironment simulation platforms, Int. J Clin Exp. Pathol, 2017, 10(2):842-852.
Zhang, CAR T-cell therapy: opportunities and Challenges, Immunotherapy, 2016, 8(3):245-247.
Zhao, et al. Affinity maturation of T-cell receptor-like antibodies for Wilms tumor 1 peptide greatly enhances therapeutic potential. Leukemia. Nov. 2015;29(11):2238-47. doi: 10.1038/leu.2015.125. Epub May 19, 2015.
European search report and opinion dated Nov. 19, 2019 for EP Application No. 17833264.9.
Li, et al. Adoptive Immunotherapy Using T Lymphocytes Redirected to glypican-3 for the Treatment of Lung Squamous Cell Carcinoma. Oncotarget. Jan. 19, 2016;7(3):2496-507. doi: 10.18632/oncotarget.6595.
Newick, et al. Chimeric antigen receptor T-cell therapy for solid tumors. Mol Ther Oncolytics. 2016; 3:16006. Published online Apr. 13, 2016. doi: 10.1038/mto.2016.6.
Shanghai Genechem Co., Ltd. A Study of GPC3 Redirected Autologous T Cells for Advanced HCC (GPC3-CART). NCT02715362. https://clinicaltrials.gov/ct2/history/NCT02715362. Mar. 16, 2016.
Baumhoer, et al. Glypican 3 expression in human nonneoplastic, preneoplastic, and neoplastic tissues: a tissue microarray analysis of 4,387 tissue samples. Am J Clin Pathol. Jun. 2008;129(6):899-906. doi: 10.1309/HCQWPWD50XHD2DW6.
Baylor College of Medicine. Glypican 3-specific Chimeric Antigen Receptor Expressing T Cells for Hepatocellular Carcinoma (GLYCAR) (GLYCAR).NCT02905188. https://clinicaltrials.gov/ct2/show/study/NCT02905188. Sep. 21, 2016.
CARSGEN Therapeutics, Ltd. Anti-GPC3 CAR T for Recurrent or Refractory Lung Squamous Cell Carcinoma. NCT02876978. https://clinicaltrials.gov/ct2/show/NCT02876978. Aug. 23, 2016.
Erikson, et al. Future supply and demand for oncologists : challenges to assuring access to oncology services. J Oncol Pract. Mar. 2007;3(2):79-86.
Huiping Gao, et al. Development of T Cells Redirected to Glypican-3 for the Treatment of Hepatocellular Carcinoma. Clinical Cancer Research, vol. 20, No. 24, Dec. 15, 2014, pp. 6418-6428.
International search report with written opinion dated Jul. 4, 2017 for PCT/CN2017/081446.
Muranski, et al. Increased intensity lymphodepletion and adoptive immunotherapy—how far can we go? Clin Pract Oncol. Dec. 2006;3(12):668-81.
Xinqiao Hospital of Chongqing. Anti-GPC3 CAR-T for Treating GPC3-positive Advanced Hepatocellular Carcinoma (HCC). NCT03084380. https://clinicaltrials.gov/ct2/show/NCT03084380. Mar. 17, 2017.
Ahmed, et al. Human Epidermal Growth Factor Receptor 2 (HER2)-Specific Chimeric Antigen Receptor-Modified T Cells for the Immunotherapy of HER2-Positive Sarcoma. J Clin Oncol. May 20, 2015;33(15):1688-96. doi: 10.1200/JCO.2014.58.0225. Epub Mar. 23, 2015.
Gao, et al. Cell Culture System for Analysis of Genetic Heterogeneity Within Hepatocellular Carcinomas and Response to Pharmacologic Agents. Gastroenterology. Jan. 2017;152(1):232-242.e4. doi: 10.1053/j.gastro.2016.09.008. Epub Sep. 14, 2016.
Hinrichs, et al. Reassessing target antigens for adoptive T-cell therapy. Nat Biotechnol. Nov. 2013;31(11):999-1008. doi: 10.1038/nbt.2725. Epub Oct. 20, 2013.
Hoyos, et al. Genetic modification of human T lymphocytes for the treatment of hematologic malignancies. Haematologica. Nov. 2012; 97(11): 1622-1631. doi: 10.3324/haematol.2012.064303.
Mirzaei, et al. Chimeric Antigen Receptors T Cell Therapy in Solid Tumor: Challenges and Clinical Applications. Front Immunol. Dec. 22, 2017;8:1850. doi: 10.3389/fimmu.2017.01850. eCollection 2017.
Morgan, R.A., et al., Case report of a serious adverse event following the administration of T cells transduced with a chimeric antigen receptor recognizing ERBB2. Molecular Therapy, Apr. 18, 2010. pp. 843-851 vol. 18, No. 4. e-pub Feb. 23, 2010.
Zhai, et al. A phase I study of anti-GPC3 chimeric antigen receptor modified T cells (GPC3 CAR-T) in Chinese patients with refractory or relapsed GPC3+ hepatocellular carcinoma (r/r GPC3+ HCC). Journal of Clinical Oncology 2017 35:15_suppl, 3049-3049.

* cited by examiner

Pre-treatment (baseline)     Ten weeks after treatment

COMPOSITIONS AND METHODS OF CELLULAR IMMUNOTHERAPY

CROSS-REFERENCE

This application is a continuation of PCT Application PCT/CN2017/081446, filed Apr. 21, 2017, which claims the benefit of CN patent application number CN201610256568.9 filed on Apr. 22, 2016, the content of which is incorporated herein in its entirety.

The instant application contains a Sequence Listing which has been filed electronically in ASCII format and is hereby incorporated by reference in its entirety. Said ASCII copy, created on Jan. 8, 2019, is named 52022-704 301 SL.txt and is 99,903 bytes in size.

BACKGROUND

Cancer has a major impact on society in across the globe. In 2016, an estimated 1,685,210 new cases of cancer will be diagnosed in the United States alone, and 595,690 people will die from the disease. By 2020, 18.2 million Americans, roughly 1 in 19 people, will be cancer patients or cancer survivors, up from 11.7 million (1 in 26) in 2005, according to the *Journal of Oncology Practice* (Erikson 2007).

Chimeric antigen receptors (CARs) are recombinant receptors for antigen, which, in a single molecule, redirect the specificity and function of T cells and other immune cells. Their use in cancer immunotherapy can be to rapidly generate tumor-targeted T cells, bypassing the obstacles of active immunization. Once expressed in cells, the CAR-modified cell may exert both immediate and long-term effects in a subject.

Chimeric antigen receptor (CAR) T cell therapy, which edits a cancer patient's T cells to recognize their tumors, has shown to be effective for treating blood cancers. In recent clinical trials, CAR T cell therapy has dramatically improved the outcomes of blood cancer patients with advanced, otherwise untreatable forms of leukemia and lymphoma. In contract, CAR T cells face a unique set of challenges in the context of solid tumors. Amongst the challenges include the identification of an antigen whose expression clearly demarcates tumor from normal tissue and establishing effective killing of tumor cells within a tumor and hence reduction of tumor size.

SUMMARY OF THE INVENTION

There exists a pressing need for alternative and effective treatment for a wide variety of solid tumors. The present invention addresses this need and provides related advantages as well. Accordingly, the present invention discloses a method of treating a subject exhibiting a solid tumor that can express Glypican-3 (GPC3). In some cases, the method can comprise administering anti-GPC3 chimeric antigen receptor immunoresponsive cells to a subject. In some cases, an administration can take place after or concurrent with subjecting a subject to a lymphocyte reduction treatment. In some cases, immunoresponsive cells can be NK cells (anti-GPC3-CAR NK cells) or T cells (anti-GPC3-CAR T cells). In some cases, an administration of anti-GPC3-CAR T cells to a subject can take place after subjecting a subject to a lymphocyte reduction treatment. In some cases, at least about $5\times10^4$ anti-GPC3-CAR T cells/kg can be administered to a subject. In some cases, from about $5\times10^4$ to about $1\times10^{12}$ anti-GPC3-CAR T cells/kg are administered to a subject. An administration can be effective in reducing tumor size by at least 30% as measured by computerized tomography (CT) scan. In some cases, an administration can be effective in stabilizing tumor size as measured by a less than 10% change in a baseline measurement of a diameter of a tumor lesion as measured by computerized tomography (CT) scan. In some cases, administering of anti-GPC3-CAR T cells and a subjecting a subject to a lymphocyte reduction treatment can synergistically increase a subject's medium survival time by at least about 6 months as compared to administering anti-GPC3-CAR T cells alone. In some cases, a solid tumor can be liver cancer, stomach cancer, thyroid cancer (e.g., thyroid carcinoma), lung cancer, breast cancer, head and neck cancer, ovarian cancer, kidney cancer, bladder cancer, cervical cancer, pancreatic cancer, liposarcoma, testicular nonseminomatous germ cell cancer, melanoma, adenoma of the adrenal gland, schwannoma, malignant fibrous histiocytoma, or esophageal cancer. In some cases, an anit-GPC3 chimeric antigen receptor can comprise an antigen binding unit that can exhibit specific binding to a C-terminus of GPC3. In some cases, an antigen binding unit can comprise a sequence exhibiting at least 50%, 55%, 60%, 65%, 70%, 75%, 80%, 85%, 90%, 91%, 92%, 93%, 94%, 95%, 96%, 97%, 98%, 99%, or up to about 100% sequence homology to SEQ ID NO: 1, SEQ ID NO: 2, SEQ ID NO: 3, SEQ ID NO:4, SEQ ID NO: 5, SEQ ID NO: 6, SEQ ID NO: 7, or SEQ ID NO: 8. In some cases, an anti-GPC3-CAR can comprise a sequence exhibiting at least 50%, 55%, 60%, 65%, 70%, 75%, 80%, 85%, 90%, 91%, 92%, 93%, 94%, 95%, 96%, 97%, 98%, 99%, or up to about 100% sequence identity to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO: 30. An anti-GPC3-CAR can comprise a sequence exhibiting at least 50%, 55%, 60%, 65%, 70%, 75%, 80%, 85%, 90%, 91%, 92%, 93%, 94%, 95%, 96%, 97%, 98%, 99%, or up to about 100% sequence identity to any one of SEQ ID NOS 28 to 30. In some cases, anti-GPC3-CAR T cells can comprise at least two intracellular signaling domains. In some cases, anti-GPC3-CAR T cells can comprise at least three intracellular signaling domains. Intracellular signaling domains can be selected from a signaling domain derived from CD3, CD28, 4-1BB, OX40, DAP10, or ICOS. In some cases, a lymphocyte reduction treatment can comprise reducing a quantity of regulatory T cells in a subject. Reducing a quantity of regulatory T cells can comprise a reduction of at least about 30%, 40%, 50%, 60%, 70%, 80%, 90%, 95% or higher, of regulatory T cells as measured by flow cytometric analysis of circulating $CD4^+$ and $CD25^+$ cells in a subject. In some cases, a lymphocyte reduction treatment can comprise administering radiation or a biological agent to a subject. A lymphocyte reduction treatment can also comprise administering chemotherapy to a subject. An administration of chemotherapy to a subject can comprise administering a chemotherapeutic agent selected from the group consisting of cyclophosphamide, fludarabine, etoposide, cytarabine, methotrexate, vincristine, adriamycin, and any combination thereof. In some cases, a chemotherapeutic agent can be administered to a subject at least one time prior to administration of anti-GPC3-CAR T cells. In some cases, a lymphocyte reduction treatment can reduce a quantity of lymphocytes by at least about 20% as measured by complete blood count (CBC) analysis.

Disclosed herein can also be a method further comprising a second administration of anti-GPC3-CAR T cells to a subject. In some cases, a subject can have refractory, persistent, or progressive disease. Anti-GPC3-CAR T cells can be autologous or allogenic to a subject.

Disclosed herein can also be a method further comprising administering at least one immunostimulatory agent to a subject concurrent or after administration of anti-GPC3 chimeric antigen receptor immunoresponsive cells. An immunostimulatory agent can be selected from the group consisting of aldesleukin (IL-2), IL-3, IL-6, IL-11, GM-CSF, and any combination thereof. A biological agent can be an antibody directed to an antigen expressed on a lymphocyte.

Disclosed herein is a kit for administering anti-GPC3-CAR immunoresponsive cells to a subject exhibiting a solid tumor, comprising: an effective amount of anti-GPC3-CAR immunoresponsive cells; a chemotherapeutic agent effective in reducing lymphocytes present in a subject; and instructions for administering anti-GPC3-CAR immunoresponsive cells after or concurrently with a chemotherapeutic agent to a subject. In some cases, anti-GPC3-CAR immunoresponsive cells can be NK cells or T cells (anti-GPC3-CAR T cells). A chemotherapeutic agent can be selected from the group consisting of cyclophosphamide, fludarabine, etoposide, cytarabine, methotrexate, vincristine, adriamycin, and any combination thereof. A kit can further comprise about 60 mg/kg to about 80 mg/kg cyclophosphamide or about 25 mg/m$^2$ to about 35 mg/m$^2$ fludarabine formulated for administration to a subject in need thereof. In some cases, a kit can comprise from about $1 \times 10^4$ cells to about $1 \times 10^{12}$ anti-GPC3-CAR T cells. In some cases, instructions can provide procedures for administering anti-GPC3-CAR T cells after administering a chemotherapeutic agent. In some cases, instructions can provide procedures for administering anti-GPC3-CAR T cells at least 12 hours after administering a chemotherapeutic agent. In some cases, instructions can provide procedures for administering anti-GPC3-CAR T cells at least 24 hours after administering a chemotherapeutic agent. Anti-GPC3-CAR T cells can be formulated for intravenous injection. Anti-GPC3-CAR T cells can be formulated for intra-arterial injection to a subject's liver that can comprise a solid tumor.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure can be utilized, and the accompanying drawings of which:

DETAILED DESCRIPTION OF THE DISCLOSURE

Figure 1:
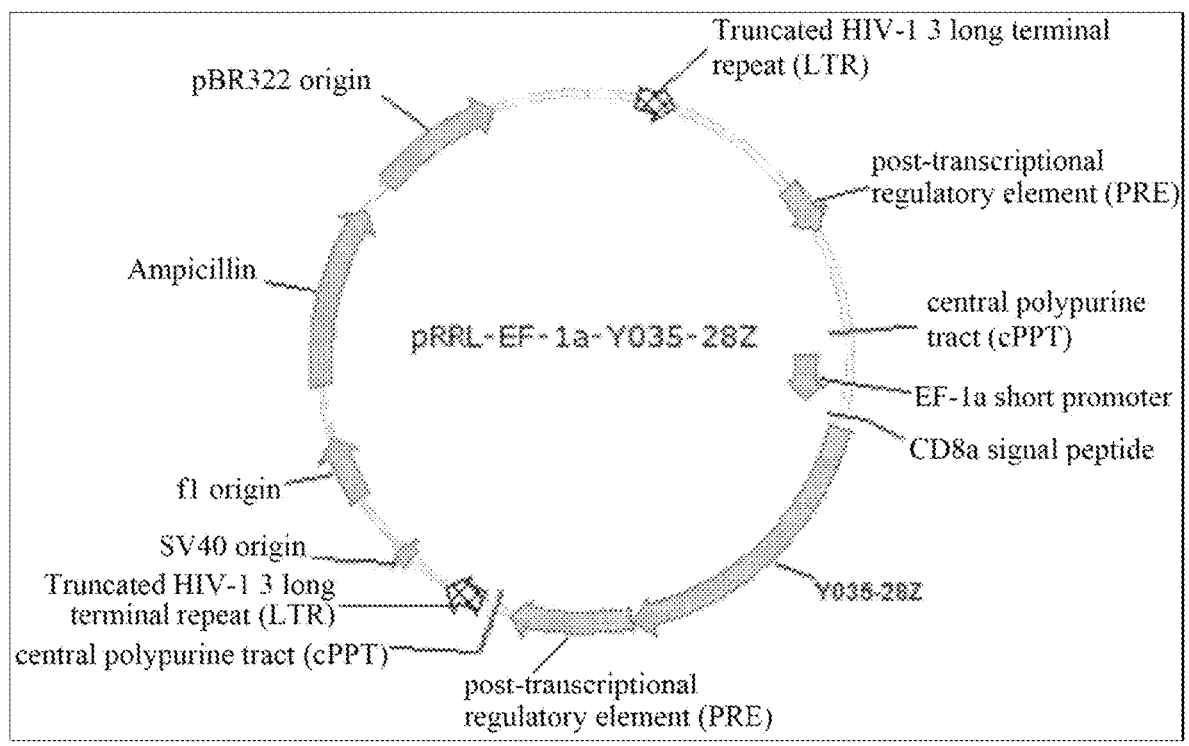
FIG. 1 shows a second generation CAR-T vector encoding a chimeric antigen receptor targeting GPC3.

The following description and examples illustrate embodiments of the disclosure in detail. It is to be understood that this disclosure is not limited to the particular embodiments described herein and as such can vary. Those of skill in the art will recognize that there are numerous variations and modifications of the disclosure, which are encompassed within its scope. Unless otherwise indicated, any embodiment can be combined with any other embodiment.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Definitions

As used herein, unless otherwise indicated, the article "a" means one or more unless explicitly otherwise provided for.

As used herein, unless otherwise indicated, terms such as "contain," "containing," "include," "including," and the like mean "comprising".

The term "activation" and its grammatical equivalents as used herein can refer to a process whereby a cell transitions from a resting state to an active state. This process can comprise a response to an antigen, migration, and/or a phenotypic or genetic change to a functionally active state. For example, the term "activation" can refer to the stepwise process of T cell activation. For example, a T cell can require at least two signals to become fully activated. The first signal can occur after engagement of a TCR by the antigen-MHC complex, and the second signal can occur by engagement of co-stimulatory molecules (Table 3). Anti-CD3 can mimic the first signal and anti-CD28 can mimic the second signal in vitro. For example, an engineered T cell can be activated by an expressed CAR. T cell activation" or T cell triggering, as used herein, can refer to the state of a T cell that has been sufficiently stimulated to induce detectable cellular proliferation, cytokine production and/or detectable effector function.

The term "antigen binding unit" as used herein refers to an immunoglobulin molecule and immunologically active portions of immunoglobulin molecule, i.e., a molecule that contains an antigen-binding site which specifically binds ("immunoreacts with") an antigen. Also encompassed within the term "antigen binding unit" are immunoglobulin molecules of a variety of species origins including invertebrates and vertebrates. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Also encompassed within the term "antigen binding unit" is any polypeptide chain-containing molecular structure that has a specific shape which fits to and recognizes an epitope, where one or more non-covalent binding interactions stabilize the complex between the molecular structure and the epitope.

An antigen binding unit "specifically binds to" or "immunoreactive with" an antigen if it binds with greater affinity or avidity than it binds to other reference antigens including polypeptides or other substances.

"Antigen" as used herein means a substance that is recognized and bound specifically by an antigen binding unit. Antigens can include peptides, proteins, glycoproteins, polysaccharides, and lipids; portions thereof and combinations thereof. Non-limiting exemplary antigen included GPC3 from human, murine, and other homologues thereof. "Antigen" can also refer to a molecule that provokes the immune response. This immune response may involve either antibody production, or the activation of specific immunologically-competent cells, or both. The skilled artisan will understand that any macromolecule, including virtually all proteins or peptides, can serve as an antigen.

The term "immunoglobulin" or "Ig", as used herein can refer to a class of proteins, which function as antibodies. Antibodies expressed by B cells are sometimes referred to as the chimeric antigen receptor or antigen receptor. The five members included in this class of proteins are IgA, IgG, IgM, IgD, and IgE, of which IgG is the most common circulating antibody. It is the most efficient immunoglobulin in agglutination, complement fixation, and other antibody responses, and is important in defense against bacteria and viruses. For example, a tumor cell antigen can be recognized by a CAR.

The term "anti-GPC3 antibody" can refer to an antibody or antibody binding site that is capable of binding GPC3 with sufficient affinity such that the antibody is useful for distinguishing GPC3 from other antigens expressed by a cell. In one embodiment, the extent of binding of an anti-GPC3 antibody to an unrelated, non-GPC3 protein is less than about 10% of the binding of the antibody to GPC3 as measured, e.g., by a radioimmunoassay (RIA). In certain embodiments, an antibody that binds to GPC3 can have a dissociation constant (Kd) of <1 µM, <100 nM, <10 nM, <5 nM, <4 nM, <3 nM, <2 nM, <1 nM, <0.1 nM, <0.01 nM, or <0.001 nM (e.g., $10^{-8}$M or less, e.g. from $10^{-8}$ M to $10^{-13}$ M, e.g., from $10^{-9}$M to $10^{-13}$ M). In certain embodiments, an anti-GPC3 antibody binds to an epitope of GPC3 that is conserved among GPC3 from different species.

The term "autologous" and its grammatical equivalents as used herein can refer to as originating from the same being. For example, a sample (e.g., cells) can be removed, processed, and given back to the same subject (e.g., patient) at a later time. An autologous process is distinguished from an allogenic process where the donor and the recipient are different subjects.

"Xenotransplantation" and its grammatical equivalents as used herein can encompass any procedure that involves transplantation, implantation, or infusion of cells, tissues, or organs into a recipient, where the recipient and donor are different species. Transplantation of the cells, organs, and/or tissues described herein can be used for xenotransplantation in into humans. Xenotransplantation includes but is not limited to vascularized xenotransplant, partially vascularized xenotransplant, unvascularized xenotransplant, xenodressings, xenobandages, and xenostructures.

"Allotransplantation" and its grammatical equivalents (e.g., allogenic transplantation) as used herein can encompass any procedure that involves transplantation, implantation, or infusion of cells, tissues, or organs into a recipient, where the recipient and donor are the same species but different individuals. Transplantation of the cells, organs, and/or tissues described herein can be used for allotransplantation into humans. Allotransplantation includes but is not limited to vascularized allotransplant, partially vascularized allotransplant, unvascularized allotransplant, allodressings, allobandages, and allostructures.

"Autotransplantation" and its grammatical equivalents (e.g., autologous transplantation) as used herein can encompass any procedure that involves transplantation, implantation, or infusion of cells, tissues, or organs into a recipient, where the recipient and donor is the same individual. Transplantation of the cells, organs, and/or tissues described herein can be used for autotransplantation into humans. Autotransplantation includes but is not limited to vascularized autotransplantation, partially vascularized autotransplantation, unvascularized autotransplantation, autodressings, autobandages, and autostructures.

The term "chimeric antigen receptor" or "CAR" as used herein refers to an engineered molecule, which can be expressed by an immune cell including but not limited to T cells. CAR when expressed in T cells and can redirect T cells to induce killing of a target cell with a specificity dictated by the artificial receptor. The CAR's extracellular binding domain can be derived from a murine, humanized, or fully human monoclonal antibody. An "anti-GPC3-CAR" is a CAR that is capable of binding to GPC3.

The term "epitope" and its grammatical equivalents as used herein can refer to a part of an antigen that can be recognized by antibodies, B cells, T cells or engineered cells. For example, an epitope can be a cancer epitope that is recognized by a TCR. Multiple epitopes within an antigen can also be recognized. The epitope can also be mutated.

The term "engineered" and its grammatical equivalents as used herein can refer to one or more alterations of a nucleic acid, e.g., the nucleic acid within an organism's genome. The term "engineered" can refer to alterations, additions, and/or deletion of genes. An engineered cell can also refer to a cell with an added, deleted and/or altered gene.

The term "cell" or "engineered cell" and their grammatical equivalents as used herein can refer to a cell of human or non-human animal origin. An engineered cell can also refer to a CAR-expressing cell.

The term "good manufacturing practices" (GMP) and its grammatical equivalents as used herein can refer to products that are safe, effective, or pure according to the FDA. GMP can also sometimes be referred to as "cGMP". The "c" stands for "current." Manufacturers of a product can employ technologies and systems which are up-to-date in order to comply with regulation of GMP products. GMP compatible products are typically utilized in the clinical setting as opposed to the research setting.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The term "subject", as used herein, refers to any animal, e.g., a mammal or marsupial. Subjects of the present invention include but are not limited to humans, non-human primates (e.g., rhesus or other types of macaques), mice, pigs, horses, donkeys, cows, sheep, rats and fowl of any kind.

The term "recipient" and their grammatical equivalents as used herein can refer to a human or non-human animal in receipt of a therapy or treatment.

The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The term "immunoresponsive cell" can refer to a cell that can elicit an immune response, including but not limited to T cells, B cells, and NKT cells, their respective precursor cells and progeny thereof. An immunoresponsive cell can also refer to a cell of a lymphoid or myeloid lineage.

The term "T cell" and its grammatical equivalents as used herein can refer to a T cell from any origin. For example, a T cell can be a primary T cell, e.g., an autologous T cell, a cell line, etc. The T cell can also be human or non-human.

The term "T cell activation" or "T cell triggering" and its grammatical equivalents as used herein can refer to the state of a T cell that has been sufficiently stimulated to induce detectable cellular proliferation, cytokine production and/or detectable effector function. In some cases, "full T cell activation" can be similar to triggering T cell cytotoxicity. T cell activation can be measured using various assays known in the art. Said assays can be an ELISA to measure cytokine secretion, an ELISPOT, flow cytometry assays to measure intracellular cytokine expression (CD107), flow cytometry assays to measure proliferation, and cytotoxicity assays (51Cr release assay) to determine target cell elimination. Said assays typically use controls (non-engineered cells) to compare to engineered cells (CAR T) to determine relative activation of an engineered cell compared to a control. Additionally, said assays can compare engineered cells incubated or put in contact with a target cell not expressing the target antigen. For example, said comparison can be a CD19-CAR T cell incubated with a target cell that does not express CD19.

The term "sequence" and its grammatical equivalents when used to refer to a nucleotide sequence, can encompass DNA or RNA; and can be either single-stranded or double stranded. A nucleic acid sequence can be mutated. A nucleic acid sequence can be of any length, for example, between 2 and 1,000,000 or more nucleotides in length (or any integer value there between or there above), e.g., between about 100 and about 10,000 nucleotides or between about 200 and about 500 nucleotides.

Methods of Use

In one aspect, disclosed herein are methods of treating a subject exhibiting a solid tumor that expresses Glypican-3 (GPC3). A subject method typically comprises the step of administering anti-GPC3 chimeric antigen receptor immunoresponsive cells to a subject, wherein the administering takes place after or concurrent with subjecting the subject to a lymphocyte reduction treatment.

Subjects treated by methods disclosed herein can exhibit a cancer or a solid tumor. Often, cancer cells or solid tumor cells express one or more tumor antigens. Typically, the tumor antigen is Glypican-3 (GPC3). A subject exhibiting a cancer or solid tumor expressing GPC-3 can be referred to as exhibiting a GPC3-positive cancer.

Cancers that express GPC3 include but are not limited to liver cancer, stomach cancer, esophageal cancer, lung cancer, breast cancer, head and neck cancer, ovarian cancer, kidney cancer, bladder cancer, cervical cancer, pancreatic cancer, liposarcoma, testicular noneminomatous germ cell cancer, melanoma, adenoma, adrenal cancer, schwannoma, malignant, fibrous histiochytoma, or any combination thereof. The subject methods are applicable for treating squamous cell carcinoma or adenocarcinoma, neuroendocrine carcinoma of a GI tract, or any other cancer disclosed in "Glypican-3 expression in gastrointestinal and pancreatic epithelial neoplasms. (2013) 44, 542-550 Human Pathology." Additionally immunoresponsive cells disclosed herein, such as an anti-GPC3-CAR-T disclosed herein, can be utilized to target ovarian carcinoma, cholangiocarcinoma, mesothelioma, breast cancer, squamous cell carcinoma of the lunch, cervical intraethithelial neoplasia, squamous cell carcinoma of the cervix, intrahepatic and extrahepatic cancer, gallbladder carcinoma, invasive ductal carcinoma, clear cell carcinoma, oncocytoma, papillary carcinoma, adenocarcinoma, papillary carcinoma, and lobular and medullary carcinoma of the breast. Additional targets for anti-GPC3 therapy can include those found in, "Glypican 3 expression in human nonneoplastic, preneoplastic, and neoplastic tissues. (2008) 129:899-906 Am J ClinPathol."

In some cases, a cancer or tumor cell can be evaluated for GPC3 expression by flow cytometry or immunohistochemistry. A level of GPC3 on a cancer or tumor cell can be classified as low, medium, or high.

In some cases, a cancer or tumor cell can express GPC3 on the cell surface. Expression of GPC3 on a cell surface can be determined, for example, using antibodies to GPC3 in a method such as immunohistochemistry or flow cytometric analysis. Alternatively, GPC3 mRNA expression can be considered to correlate to GPC3 expression on a cell surface and can be determined by a method selected from in situ hybridization and RT-PCR.

In some cases, GPC3 is encoded by a gene comprising the nucleic acid sequence exhibiting at least 50% sequence identity to the referenced gene in Table 2. GPC3 can be encoded by a gene comprising the nucleic acid sequence exhibiting at least about 50%, 55%, 60%, 65%, 70%, 75%, 80%, 85%, 90%, 95%, 96%, 97%, 98%, 99%, or up to about 100% sequence identity to the referenced gene in Table 2.

In some embodiments, anti-GPC3 chimeric antigen receptor immunoresponsive cells are administered to a subject exhibiting a solid tumor expressing GPC3 after or concurrent with subjecting the subject to a lymphocyte reduction treatment.

A subject anti-GPC3 chimeric antigen receptor (CAR) typically comprises an extracellular antigen binding region, a transmembrane domain, and an intracellular signaling region that controls immunoresponsive cell activation. In some cases, the anti-GPC3 CAR further comprises a hinge or spacer. In some cases, the anti-GPC3 CAR further comprises one or more co-stimulatory domains.

A chimeric antigen receptor typically comprises an extracellular antigen binding region. In one embodiment, the extracellular antigen binding region can be fully human. In other cases, the extracellular antigen binding region can be humanized. In other cases, the extracellular antigen binding region can be murine or a chimeric in the extracellular antigen binding region is composed of amino acid sequences derived from at least two different animal species. In some cases, the extracellular antigen binding region can be non-human. A variety of antigen binding regions can be designed to target GPC3. Non-limiting examples include single-chain variable fragments (scFv's) derived from antibodies, fragment antigen binding region (Fab) selected from libraries, single domain fragment, or nature ligands that engage their cognate receptor. An extracellular antigen binding region can encompass a scFv, a Fab, or a nature ligand, as well as any of their derivatives. An extracellular antigen binding region can refer to a molecule other than an intact antibody that can comprise a portion of an intact antibody and that can bind an antigen to which an intact antibody binds. Examples of antibody fragments can include but are not limited to Fv, Fab, Fab', Fab'-SH, F (ab') 2; diabodies; linear antibodies; single-chain antibody molecules (e.g. scFv); and multispecific antibodies formed from antibody fragments.

An extracellular antigen binding region, for example the scFv, Fab, or natural ligand, can be a portion of a CAR that determines antigen specificity. An extracellular antigen binding region can bind to any complementary target. An extracellular antigen binding region can be derived from an antibody for which sequences of a variable region are known. An extracellular antigen binding region can be derived from an antibody sequence obtained from an available mouse hybridoma. Alternatively, an extracellular antigen binding region can be obtained from whole-exomic sequencing of a tumor cell or primary cell, such as a tumor infiltrating lymphocyte (TIL).

In some cases, binding specificity of an extracellular antigen binding region can be determined by complementarity determining regions, or CDRs, such as light chain CDRs or heavy chain CDRs. In many cases, binding specificity can be determined by light chain CDRs and heavy chain CDRs. A given combination of heavy chain CDRs and light chain CDRs can provide a given binding pocket that can confer a greater affinity and/or specificity towards an antigen, such as GPC3, as compared to other reference antigens. For example, a CDR specific to glypican-3 can be expressed in an extracellular binding region of a CAR such that the CAR targeting the GPC3 can target the immunoresponsive cell to a tumor cell expressing GPC3.

In some aspects of any of the embodiments disclosed herein, an extracellular antigen binding region, such as a scFv, can comprise a light chain CDR specific for GPC3. A light chain CDR can be a complementarity determining region of a light chain of an antigen binding unit, such as a scFv of a CAR. A light chain CDR can comprise a continuous sequence of amino acid residues, or two or more contiguous sequences of amino acid residues separated by, and optionally flanked by, non-complementarity determining regions, such as framework regions. In some cases, a light chain CDR can comprise two or more light chain CDRs, which can be referred to as light chain CDR-1, CDR-2, and so on. In some cases, a light chain CDR can comprise three light chain CDRs, which can be referred to as light chain CDR-1, light chain CDR-2, and light chain CDR-3 respectively. In some examples, a group of CDRs present on a common light chain can collectively be referred to as light chain CDRs.

In some aspects of any of the embodiments disclosed herein, extracellular antigen binding region, such as a scFv, can comprise a heavy chain CDR specific for GPC3. A heavy chain CDR can be a complementarity determining region of a heavy chain of an antigen binding unit such as a scFv. A heavy chain CDR can comprise a continuous sequence of amino acid residues, or two or more contiguous sequences of amino acid residues separated by, and optionally flanked by, non-complementarity determining regions, such as framework regions. In some cases, a heavy chain CDR can comprise two or more heavy chain CDRs, which can be referred to as heavy chain CDR-1, CDR-2, and so on. In some cases, a heavy chain CDR can comprise three heavy chain CDRs, which can be referred to as heavy chain CDR-1, heavy chain CDR-2, and heavy chain CDR-3 respectively. In some cases, a group of CDRs present on a common heavy chain can collectively be referred to as heavy chain CDRs.

In some cases, an extracellular antigen binding region targeting GPC3 can be expressed by an anti-GPC3 CAR immunoresponsive cell. In some cases, CDRs, light chain and/or heavy chain that bind a GPC3 antigen can be comprised within an extracellular antigen binding region of a CAR immunoresponsive cell, such as CAR T cells. In some cases, modified anti-GPC3 CDRs can be expressed on an extracellular antigen binding region of a CAR immunoresponsive cell and have from about 50% homology to about 100% homology to original anti-GPC3 CDRs. In some cases, a modified anti-GPC3 CDR can comprise from about 50%, 55%, 60%, 65%, 70%, 75%, 80%, 85%, 90%, 91%, 92%, 93%, 94%, 95%, 96%, 97%, 98%, 99%, or up to about 100% homology to an unmodified anti-GPC3 CDR.

In some cases, a scFv targeting GPC3 can be expressed by an anti-GPC3 CAR immunoresponsive cell. In some cases, CDRs, light chain and/or heavy chain that bind a GPC3 antigen can be expressed on a scFv of a CAR immunoresponsive cell, such as CAR T cells. In some cases, modified anti-GPC3 CDRs can be expressed on a scFv of a CAR immunoresponsive cell, such as CAR T cells, and have from about 50% homology to about 100% homology to original anti-GPC3 CDRs. In some cases, a modified anti-GPC3 CDR can comprise from about 50%, 55%, 60%, 65%, 70%, 75%, 80%, 85%, 90%, 91%, 92%, 93%, 94%, 95%, 96%, 97%, 98%, 99%, or up to about 100% homology to an unmodified anti-GPC3 CDR.

TABLE 1

Exemplary anti-GPC3 extracellular antigen binding regions:

| SEQ ID NOS: | 1, 2, 3, 4, 5, 6, 7, 8 |
|---|---|

In preferred cases, an extracellular antigen binding region specifically recognizes GPC3. GPC3 can comprise a sequence exhibition at least 80% identical to a referenced GPC3 gene in Table 2. In some cases, extracellular antigen binding region can target an N-terminus, a C-terminus, or any portion from an N-terminus to a C-terminus of GPC3. A C-terminus of a GPC3 can be attached to a cell membrane covalently via a glycosylphosphatidylinositol (GPI) anchor. A C-terminus can comprise from about 1 to about 800 bases in some cases. A C-terminus can comprise from about 1, 50, 100, 150, 300, 500, 600 up to about 800 bases from a C-terminal end. In some cases, an extracellular antigen binding region can target the GPI anchor of GPC3.

TABLE 2

| GPC3 | | | | | |
|---|---|---|---|---|---|
| Abbrev. | Name | NCBI No: GRCh38.p7 | Start | Stop | Location in Genome |
| GPC3 | Glypican 3 | 2719 | 133535745 | 133985646 | Xq26.2 |

By employing genetic engineering, an extracellular antigen binding region may be modified in a variety of ways. In some cases, an extracellular antigen binding region can be mutated, so that the extracellular antigen binding region may be selected for higher affinity to its target. In some cases, the affinity of the extracellular antigen binding region for its target can be optimized for targets that can be expressed at low levels on normal tissues. This optimization can be performed to minimize potential toxicities. In other cases, the cloning of an extracellular antigen binding region that has a higher affinity for the membrane bound form of a target can be preferable over its soluble form counterpart. This modification can be performed because some targets can also be detected in soluble form at different levels and their targeting can cause unintended toxicity.

In some cases, a extracellular antigen binding region can be from about 50% to about 100% similar in homology to any one of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In some cases, a extracellular antigen binding region can comprise about 50%, 60%, 70%, 80%, 90%, 91%, 92%, 93%, 94%, 95%, 96%, 97%, 98%, 99%, or up to about 100% homology to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In some cases, extracellular antigen binding region can be murine, humanized, or fully human. An extracellular antigen binding region can be from about 1% to about 100% human. In some cases, a extracellular antigen binding region can be from about 10%, 20%, 30%, 40%, 50%, 60%, 70%, 80%, 90%, or up to about 100% human.

In some cases, an extracellular antigen binding region comprises a hinge or spacer. The terms hinge and spacer can be used interchangeably. A hinge can be considered a portion of a CAR used to provide flexibility to an extracellular antigen binding region. In some cases, a hinge can be used to detect a CAR on the cell surface of a cell, particularly when antibodies to detect the extracellular antigen binding region are not functional or available. For instance the length of the hinge derived from an immunoglobulin may require optimization depending on the location of the epitope on the target that the extracellular antigen binding region is targeting.

In some cases, a hinge may not belong to an immunoglobulin but instead to another molecule such the native hinge of a CD8 alpha molecule. A CD8 alpha hinge can contain cysteine and proline residues known to play a role in the interaction of a CD8 co-receptor and MHC molecule. Said cysteine and proline residues can influence the performance of said CAR.

A CAR hinge can be size tunable and can compensate to some extent in normalizing the orthogonal synapse distance between CAR immunoresponsive cell and a target cell. This topography of the immunological synapse between an immunoresponsive cell and a target cell also defines a distance that cannot be functionally bridged by a CAR due to a membrane-distal epitope on a cell-surface target molecule that, even with a short hinge CAR, cannot bring the synapse distance in to an approximation for signaling. Likewise, membrane-proximal CAR target antigen epitopes have been described for which signaling outputs are only observed in the context of a long hinge CAR. A hinge can be tuned according to the extracellular antigen binding region that is used. A hinge can be of any length.

A transmembrane domain can anchor a CAR to the plasma membrane of a cell. A native transmembrane portion of CD28 can be used in a CAR. In other cases, a native transmembrane portion of CD8 alpha can also be used in the CAR. By "CD8" it can be meant a protein having at least 85, 90, 95, 96, 97, 98, 99 or 100% identity to NCBI Reference No: NP_001759 or a fragment thereof that has stimulatory activity. By "CD8 nucleic acid molecule" it can be meant a polynucleotide encoding a CD8 polypeptide. In some cases, a transmembrane region can be a native transmembrane portion of CD28. By "CD28" it can be meant a protein having at least 85, 90, 95, 96, 97, 98, 99 or 100% identity to NCBI Reference No: NP_006130 or a fragment thereof that has stimulatory activity. By "CD28 nucleic acid molecule" can be meant a polynucleotide encoding a CD28 polypeptide. In some cases, the transmembrane portion can comprise CD8a region.

An intracellular signaling region of a CAR can be responsible for activation of at least one of an effector function of the immunoresponsive cell in which the CAR has been placed in. A CAR can induce the effector function of a T cell, for example, which may be cytolytic activity or helper activity including the secretion of cytokines. Thus the term intracellular signaling region refers to the portion of a protein which transduces the effector function signal and directs the cell to perform a specialized function. While usually the entire intracellular signaling region can be employed, in many cases it is not necessary to use the entire chain of a signaling domain. In some cases, a truncated portion of the intracellular signaling region is used. In some cases, the term intracellular signaling region is thus meant to include any truncated portion of the intracellular signaling region sufficient to transduce the effector function signal.

Preferred examples of signaling domains for use in a CAR can include a cytoplasmic sequence of the T cell receptor (TCR) and co-receptors that act in concert to initiate signal transduction following target-receptor engagement, as well as any derivative or variant of these sequences and any synthetic sequence that has the same functional capability.

In some cases, said intracellular signaling region may contain signaling motifs which are known as immunoreceptor tyrosine-based activation motifs (ITAMs). Examples of ITAM containing cytoplasmic signaling sequences include those derived from TCR zeta, FcR gamma, FcR beta, CD3 gamma, CD3 delta, CD3 epsilon, CD5, CD22, CD79a, CD79b, and CD66d. However, in preferred embodiments, the intracellular signaling domain is derived from CD3 zeta chain.

An example of a T cell signaling domain containing one or more ITAM motifs is the CD3 zeta domain, also known as T-cell receptor T3 zeta chain or CD247. This domain is part of the T-cell receptor-CD3 complex and plays an important role in coupling antigen recognition to several intracellular signal-transduction pathways with primary effector activation of the T cell. As used herein, CD3 zeta is primarily directed to human CD3 zeta and its isoforms as known from Swissprot entry P20963, including proteins having a substantially identical sequence. As part of the chimeric antigen receptor, again the full T cell receptor T3 zeta chain is not required and any derivatives thereof comprising the signaling domain of T-cell receptor T3 zeta chain are suitable, including any functional equivalents thereof.

An intracellular signaling domain can be selected from any one of the domains of Table 3. In some cases, a domain may be modified so that homology to any one of the referenced domains may from about 50% to about 100%. Any one of the domains of Table 3 may be modified such that a modified version may comprise from about 50, 60, 70, 80, 90, 95, 96, 97, 98, 99, or up to about 100% homology.

An intracellular signaling region of a CAR can further comprise one or more costimulatory domains. An intracellular signaling region can comprise a single co-stimulatory domain, for example a zeta-chain ($1^{st}$ generation CAR), or CD28 or 4-1BB ($2^{nd}$ generation CAR). In other examples, an intracellular signaling region can comprise two co-stimulatory domains, such as CD28/OX40 or CD28/4-1BB ($3^{rd}$ generation).

Together with intracellular signaling domains such as CD8, these co-stimulatory domains can produce downstream activation of kinase pathways, which support gene transcription and functional cellular responses. Co-stimulatory domains of CARs can activate proximal signaling proteins related to either CD28 (Phosphatidylinositol-4, 5-bisphosphate 3-kinase) or 4-1BB/OX40 (TNF-receptor-associated-factor adapter proteins) pathways, and MAPK and Akt activation.

In some cases, signals generated through the CAR can be complexed with secondary or co-stimulatory signals. With respect to the co-stimulatory signaling domain, the chimeric antigen receptor like complex can be designed to comprise several possible co-stimulatory signaling domains. As is well known in the art, in naïve T-cells the mere engagement of the T-cell receptor is not sufficient to induce full activation of T-cells into cytotoxic T-cells. Full, productive T cell activation requires a second co-stimulatory signal. Several receptors that have been reported to provide co-stimulation for T-cell activation, include, but are not limited to CD28, OX40, CD27, CD2, CD5, ICAM-1, LFA-1 (CD11a/CD18), 4-1BBL, MyD88 and 4-1BB. The signaling pathways utilized by these co-stimulatory molecules share the common property of acting in synergy with the primary T cell receptor activation signal. These co-stimulatory signaling regions provide a signal that can be synergistic with the primary effector activation signal originating from one or more ITAM motifs, for example a CD3 zeta signaling domain, and can complete the requirements for activation of the T cell.

In some cases, addition of co-stimulatory domains to a chimeric antigen receptor-like complex can enhance efficacy and durability of engineered cells. In another embodiment the T cell signaling domain and the co-stimulatory domain are fused to one another thereby composing the signaling region.

TABLE 3

Co-stimulatory domains

| Gene Symbol | Abbreviation | Name |
|---|---|---|
| CD27 | CD27; T14; S152; Tp55; TNFRSF7; S152. LPFS2 | CD27 molecule |
| CD28 | Tp44; CD28; CD28 antigen | CD28 molecule |
| TNFRSF9 | ILA; 4-1BB; CD137; CDw137 | tumor necrosis factor receptor superfamily, member 9 |
| TNFRSF4 | OX40; ACT35; CD134; IMD16; TXGP1L | tumor necrosis factor receptor superfamily, member 4 |
| TNFRSF8 | CD30; Ki-1; D1S166E | tumor necrosis factor receptor superfamily, member 8 |
| CD40LG | IGM; IMD3; TRAP; gp39; CD154; CD40L; HIGM1; T-BAM; TNFSF5; hCD40L | CD40 ligand |
| ICOS | AILIM; CD278; CVID1 | inducible T-cell co-stimulator |
| ITGB2 | LAD; CD18; MF17; MFI7; LCAMB; LFA-1; MAC-1 | integrin, beta 2 (complement component 3 receptor 3 and 4 subunit) |
| CD2 | T11; SRBC; LFA-2 | CD2 molecule |
| CD7 | GP40; TP41; Tp40; LEU-9 | CD7 molecule |
| KLRC2 | NKG2C; CD159c; NKG2-C | killer cell lectin-like receptor subfamily C, member 2 |
| TNFRSF18 | AITR; GITR; CD357; GITR-D | tumor necrosis factor receptor superfamily, member 18 |
| TNFRSF14 | TR2; ATAR; HVEA; HVEM; CD270; LIGHTR | tumor necrosis factor receptor superfamily, member 14 |
| HAVCR1 | TIM; KIM1; TIM1; CD365; HAVCR; KIM-1; TIM-1; TIMD1; TIMD-1; HAVCR-1 | hepatitis A virus cellular receptor 1 |
| LGALS9 | HUAT; LGALS9A, Galectin-9 | lectin, galactoside-binding, soluble, 9 |
| CD83 | BL11; HB15 | CD83 molecule |

In some cases, a subject CAR can comprise a sequence or portion thereof exhibiting from about 50% to about 100% sequence identity to any one of SEQ ID NO: 9 to SEQ ID NO: 13, Table 4. In some cases, a subject CAR can comprise a sequence exhibiting about 50%, 60%, 70%, 80%, 90%, 91%, 92%, 93%, 94%, 95%, 96%, 97%, 98%, 99%, or up to about 100% sequence identity to any one of SEQ ID NO: 9 to SEQ ID NO: 13.

TABLE 4

CAR-T domains encompassing exemplary hinge, transmembrane, intracellular domains:

| SEQ ID NOS: | 9, 10, 11, 12, 13 |
|---|---|

In some cases, a subject CAR can comprise a sequence exhibiting from about 50% to about 100% sequence identity to any one of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO: 30 (Table 5). In some cases, a subject CAR can comprise a sequence exhibiting about 50%, 60%, 70%, 80%, 90%, 91%, 92%, 93%, 94%, 95%, 96%, 97%, 98%, 99%, or up to about 100% sequence identity to any one of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26, SEQ ID NO: 27, SEQ ID NO: 28, SEQ ID NO: 29, or SEQ ID NO: 30.

TABLE 5

Exemplary Anti-GPC3 CARs

| SEQ ID NO | Construct |
|---|---|
| 14 | 4-28Z |
| 15 | 4-28BBZ |
| 16 | 4-4-28BBZ |
| 17 | 4-4-28Z |
| 18 | 4-14-28BBZ |
| 19 | 4-14-28Z |
| 20 | 4-20-28BBZ |
| 21 | 4-20-28Z |
| 22 | 4-35-28BBZ |
| 23 | 4-35-28Z |
| 24 | 4-42-28BBZ |
| 25 | 4-42-28Z |
| 26 | 33-28Z |
| 27 | 33-28BBZ |
| 28 | 92-28Z |
| 29 | 92-BBZ |
| 30 | 92-28BBZ |

In some cases, anti-GPC3 CAR can have at least one or more of the following characteristics, in any combination: a) binds to recombinant human GPC3; b) binds to recombinant cynomolgus monkey GPC3; c) binds to endogenous GPC3 on the surface of HepG2 cells; d) binds to cynomolgus monkey GPC3 expressed on the surface of 293 cells; e) binds to endogenous GPC3 on the surface of a cancer cell; f) binds to endogenous GPC3 on the surface of hepatocellular carcinoma cell; g) binds to endogenous GPC3 on the surface of cells of a cell line selected from HepG2, Hep3B, Huh7, and JHH-7; h) binds to an epitope within amino acids 25 to 137 of human GPC3; i) binds to an epitope spanning the furin cleavage site at amino acids R358/S359 of human GPC3; j) binds to full-length mature human GPC3, but does not bind to an N-terminal fragment of human GPC3 or to a C-terminal fragment of human GPC3 k) binds to an epitope within amino acids 420 to 470 of human GPC3; 1) binds to an epitope within amino acids 470 to 509 of human GPC3; m) competes for binding to human GPC3 with antibody 7H1; n) competes for binding to human GPC3 with antibody 4G7; o) competes for binding to human GPC3 with antibody 15G1; binds a C-terminal fragment of human GPC3; and/or p) competes for binding to human GPC3 with antibody 4A11.

A transgene encoding a subject anti-GPC3 CAR can be incorporated into a cell. For example, a transgene can be incorporated into an immunoresponsive cell, such as a T cell. When inserted into a cell, a transgene can be either a complementary DNA (cDNA) segment, which is a copy of messenger RNA (mRNA), or a gene itself residing in its original region of genomic DNA (with or without introns).

A nucleic acid, e.g., DNA, encoding a transgene sequence can be randomly inserted into a chromosome of a cell. A random integration can result from any method of introducing a nucleic acid, e.g., DNA, into a cell. For example, the method can be, but is not limited to, electroporation, sonoporation, use of a gene gun, lipotransfection, calcium phosphate transfection, use of dendrimers, microinjection, and use of viral vectors including adenoviral, AAV, and retroviral vectors, and/or group II ribozymes.

A DNA encoding a transgene can be introduced into a cell via electroporation. A DNA can also be introduced into a cell via lipofection, infection, or transformation. Electroporation and/or lipofection can be used to transfect primary cells. Electroporation and/or lipofection can be used to transfect primary hematopoietic cells. A DNA can also be introduced into a cell genome without the use of homologous recombination. In some cases, a DNA can be flanked by engineered sites that are complementary to the targeted double strand break region in a genome. In some cases, a DNA can be excised from a polynucleic acid so it can be inserted at a double strand break region without homologous recombination.

A transgene to be inserted can be flanked by engineered sites analogous to a targeted double strand break site in the genome to excise the transgene from a polynucleic acid so it can be inserted at the double strand break region.

A DNA encoding a transgene can also be designed to include a reporter gene so that the presence of a transgene or its expression product can be detected via activation of the reporter gene. Any reporter gene can be used, such as those disclosed above. By selecting in cell culture those cells in which a reporter gene has been activated, cells can be selected that contain a transgene.

Expression of a CAR can be verified by an expression assay, for example, qPCR or by measuring levels of RNA. Expression level can be indicative also of copy number. For example, if expression levels are extremely high, this can indicate that more than one copy of a CAR was integrated in a genome. Alternatively, high expression can indicate that a transgene was integrated in a highly transcribed area, for example, near a highly expressed promoter. Expression can also be verified by measuring protein levels, such as through Western blotting.

A subject anti-GPC3 CAR immunoresponsive cell can comprise one or more transgenes. One or more transgenes can express a CAR protein recognizing and binding to at least one epitope (e.g., GPC3) on an antigen or bind to a mutated epitope on an antigen. A CAR can be a functional CAR. A subject anti-GPC3 CAR immunoresponsive cell can also comprise one or more CARs, or it can comprise a single CAR and a secondary engineered receptor.

A transgene can encode for a suicide gene. As evidenced in many effective treatments in cancer patients, objective tumor regressions in response to CAR immunoresponsive cells can be accompanied by toxicities. In some cases, a CAR immunoresponsive cell may be unable to distinguish between tumor and normal tissues when the targeted antigen is shared between them ("on-target/off-tumor" toxicity). In other cases, systemic perturbation of the immune system, known as cytokine release syndrome (CRS), can occur. Said CRS can comprise systemic inflammatory response syndrome or cytokine storm, which can be consequences of the rapid in vivo expansion of CAR immunoresponsive cells. CRS is a condition characterized by fever and hypotension that, in severe cases, can lead to multiple organ failure. In most cases, said toxicity correlates with the in vivo expansion of infused CAR immunoresponsive cells, which can cause a general perturbation of the immune system, and release of high levels of pro-inflammatory cytokines, such as TNF alpha and IL-6.

In some cases, CAR immunoresponsive cells targeting antigens shared with normal tissues can be generated such that they transiently express the CAR, for example after electroporation of mRNA encoding the receptor. In addition, there are significant efforts to further engineer CAR immunoresponsive cells by including safety switches that can allow the drastic elimination of CAR immunoresponsive cells in case of severe on-target toxicity. Vectors encoding a CAR can be combined with safety switches, such as the inducible caspase-9 gene (activated by a chemical inducer of dimerization) or a truncated form of the EGF receptor R (activated by the monoclonal antibody cetuximab) or RQR8.

A subject anti-GPC3 CAR immunoresponsive cell can encode a suicide gene transgene. Said transgene can also comprise a CAR receptor or another similar receptor. A suicide gene can induce elimination of CAR immunoresponsive cells. A suicide gene can be any gene that induces apoptosis in said CAR immunoresponsive cell. A suicide gene can be encoded within a viral vector along with an anti-GPC3 CAR.

One or more transgenes can be from different species. For example, one or more transgenes can comprise a human gene, a mouse gene, a rat gene, a pig gene, a bovine gene, a dog gene, a cat gene, a monkey gene, a chimpanzee gene, or any combination thereof. For example, a transgene can be from a human, having a human genetic sequence. One or more transgenes can comprise human genes. In some cases, one or more transgenes are not adenoviral genes.

A transgene can be inserted into a genome of an immunoresponsive cell in a random or site-specific manner, as described above. For example, a transgene can be inserted to a random locus in a genome of an immunoresponsive cell. These transgenes can be functional, e.g., fully functional if inserted anywhere in a genome. For instance, a transgene can encode its own promoter or can be inserted into a position where it is under the control of an endogenous promoter. Alternatively, a transgene can be inserted into a gene, such as an intron of a gene or an exon of a gene, a promoter, or a non-coding region. A transgene can be inserted such that the insertion disrupts a gene, e.g., an endogenous immune checkpoint.

Sometimes, more than one copy of a transgene can be inserted into more than a random locus in a genome. For example, multiple copies can be inserted into a random locus in a genome. This can lead to increased overall expression than if a transgene was randomly inserted once. Alternatively, a copy of a transgene can be inserted into a gene, and another copy of a transgene can be inserted into a different gene. A transgene can be targeted so that it could be inserted to a specific locus in a genome of a immunoresponsive cell.

In some cases, a polynucleic acid comprising a sequence encoding a subject anti-GPC3 CAR, can take the form of a plasmid vector. A plasmid vector can comprise a promoter. In some cases, a promotor can be constitutive. In some cases, a promoter can be inducible. A promoter can be or can be derived from CMV, U6, MND, or EF1a. In some cases, a promoter can be adjacent to a CAR sequence. In some cases, a plasmid vector further comprises a splicing acceptor. In some cases, a splicing acceptor can be adjacent to a CAR sequence. A promoter sequence can be a PKG or an MND promoter. An MND promoter can be a synthetic promoter that contains a U3 region of a modified MoMuLV LTR with a myeloproliferative sarcoma virus enhancer.

In some cases, a polynucleic acid, encoding a subject anti-GPC3 CAR, can be designed to be delivered to a cell by non-viral techniques. In some cases, a polynucleic acid can be a good manufacturing practices (GMP) compatible reagent.

Expression of a polynucleic acid encoding for a subject anti-GPC3 CAR can be controlled by one or more promoters. A promoter can be a ubiquitous, constitutive (unregulated promoter that allows for continual transcription of an associated gene), tissue-specific promoter or an inducible promoter. Expression of a transgene that is inserted adjacent to or near a promoter can be regulated. For example, a transgene can be inserted near or next to a ubiquitous promoter. Some ubiquitous promoters can be a CAGGS promoter, an hCMV promoter, a PGK promoter, an SV40 promoter, or a ROSA26 promoter.

A promoter can be endogenous or exogenous. For example, one or more transgenes can be inserted adjacent or near to an endogenous or exogenous ROSA26 promoter. Further, a promoter can be specific to an immunoresponsive cell. For example, one or more transgenes can be inserted adjacent or near to a porcine ROSA26 promoter.

Tissue specific promoter or cell-specific promoters can be used to control the location of expression. For example, one or more transgenes can be inserted adjacent or near to a tissue-specific promoter. Tissue-specific promoters can be a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter.

Tissue specific promoter or cell-specific promoters can be used to control the location of expression. For example, one or more transgenes can be inserted adjacent or near to a tissue-specific promoter. Tissue-specific promoters can be a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter.

Inducible promoters can be used as well. These inducible promoters can be turned on and off when desired, by adding or removing an inducing agent. It is contemplated that an inducible promoter can be, but is not limited to, a Lac, tac, trc, trp, araBAD, phoA, recA, proU, cst-1, tetA, cadA, nar, PL, cspA, T7, VHB, Mx, and/or Trex.

Furthermore, although not required for expression, transgene sequence may also include transcriptional or translational regulatory sequences, for example, promoters, enhancers, insulators, internal ribosome entry sites, sequences encoding 2A peptides and/or polyadenylation signals.

In some instances, a transgene encodes a subject anti-GPC3 CAR wherein the transgene is inserted into a safe harbor such that an anti-GPC3 CAR is expressed. In some instances, the transgene is inserted into a PD1 and/or a CTLA-4 locus. In other cases, a transgene is delivered to the cell in a lentivirus for random insertion while the PD1- or CTLA-4 specific nucleases can be supplied as mRNAs. In some instances, the transgene is delivered via a viral vector system such as a retrovirus, AAV or adenovirus along with mRNA encoding nucleases specific for a safe harbor (e.g. AAVS1, CCR5, albumin or HPRT). The cells can also be treated with mRNAs encoding PD1 and/or CTLA-4 specific nucleases. In some cases, the polynucleotide encoding a CAR is supplied via a viral delivery system together with mRNA encoding HPRT specific nucleases and PD 1- or CTLA-4 specific nucleases. CARs that can be used with the methods and compositions disclosed herein can include all types of these chimeric proteins, including first, second and third generation designs. Other agents such as CCR2 or siRNA can be applied to reduce PD-1 expression.

In some cases, a retroviral vector (either gamma-retroviral or lentiviral) can be employed for the introduction of the transgene into an immunoresponsive cell. For example, a transgene encoding a CAR (e.g., anti-GPC3 CAR), or any receptor that binds a GPC3 antigen, or a variant, or a fragment thereof, can be cloned into a retroviral vector and expression can be driven from its endogenous promoter, from the retroviral long terminal repeat, or from a promoter specific for a target cell type of interest. Non-viral vectors may be used as well. Non-viral vector delivery systems can include DNA plasmids, naked nucleic acid, and nucleic acid complexed with a delivery vehicle such as a liposome or poloxamer.

A number of viral based systems have been developed for gene transfer into mammalian cells. For example, retroviruses provide a convenient platform for gene delivery systems. A selected gene can be inserted into a vector and packaged in retroviral particles using techniques known in the art. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells. They also have the added advantage of low immunogenicity. Adenoviral vectors have the advantage that they do not integrate into the genome of the target cell thereby bypassing negative integration-related events.

A cell can be transfected with a transgene encoding a CAR. A transgene concentration can be from about 100 picograms to about 50 micrograms. In some cases, the amount of nucleic acid (e.g., ssDNA, dsDNA, RNA) that may be introduced into a cell may be varied to optimize transfection efficiency and/or cell viability. For example, 1 microgram of dsDNA may be added to each cell sample for electroporation. In some cases, the amount of nucleic acid (e.g., dsDNA) required for optimal transfection efficiency and/or cell viability may be specific to the cell type. In some cases, the amount of nucleic acid (e.g., dsDNA) used for each sample may directly correspond to the transfection efficiency and/or cell viability. For example, a range of concentrations of transfections. A transgene encoded by a vector can integrate into a cellular genome. In some cases, integration of a transgene encoded by a vector is in the forward direction. In other cases, integration of a transgene encoded by a vector is in the reverse direction.

In some cases, the starting cell density for cellular modification, such as viral delivery of a CAR, may be varied to optimize transfection efficiency and/or cell viability. In some cases, the starting cell density for transfection or transduction of cells with a viral vector may be less than about $1 \times 10^5$ cells. In some cases, the starting cell density for cellular modification with a viral vector may be at least about $1 \times 10^5$ cells to at least about $5 \times 10^7$ cells. In some cases, the starting cell density for optimal transfection efficiency and/or cell viability may be specific to the cell type. For example, a starting cell density of $1.5 \times 10^6$ cells may optimal (e.g., provide the highest viability and/or transfection efficiency) for macrophage cells. In another example, a starting cell density of $5 \times 10^6$ cells may optimal (e.g., provide the highest viability and/or transfection efficiency) for human cells. In some cases, a range of starting cell densities may be optimal for a given cell type. For example, a starting cell density between of $5.6 \times 10^6$ and $5 \times 10^7$ cells may optimal (e.g., provide the highest viability and/or transfection efficiency) for human cells such as T cells.

The efficiency of integration of a nucleic acid sequence encoding CAR into a genome of a cell with, for example, a viral system, can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some cases, detection of a CAR on a cellular membrane of an engineered cell can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9% as measured by flow cytometry.

In some cases, the immunoresponsive cell can be a stem memory $T_{SCM}$ cell comprised of CD45RO (−), CCR7(+), CD45RA (+), CD62L+(L-selectin), CD27+, CD28+ and/or IL-7Rα+, said stem memory cells can also express CD95, IL-2Rβ, CXCR3, and/or LFA-1, and show numerous functional attributes distinctive of said stem memory cells. Alternatively, the immunoresponsive cell can also be central memory $T_{CM}$ cells comprising L-selectin and CCR7, where the central memory cells can secrete, for example, IL-2, but not IFNγ or IL-4. The immunoresponsive cells can also be effector memory $T_{EM}$ cells comprising L-selectin or CCR7 and produce, for example, effector cytokines such as IFNγ and IL-4.

Vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, T cells, bone marrow aspirates, tissue biopsy), followed by reimplantation of the cells into a patient, usually after selection for cells which have incorporated the vector. Prior to or after selection, the cells can be expanded.

A suitable immunoresponsive cell for expressing anti-GPC3-CAR can be a cell that may be autologous or non-autologous to a subject in need thereof.

A source of suitable immunoresponsive cells can be obtained from a subject. In some cases T cells can be obtained. Said T cells can be obtained from a number of sources, including PBMCs, bone marrow, lymph node tissue, cord blood, thymus tissue, and tissue from a site of infection, ascites, pleural effusion, spleen tissue, and tumors. In certain cases, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps.

Alternatively, a cell can be derived from a healthy donor, from a patient diagnosed with cancer, or from a patient diagnosed with an infection. In another embodiment, a cell can be part of a mixed population of cells which present different phenotypic characteristics. A cell line can also be obtained from a transformed T cell according to the method previously described. A cell can also be obtained from a cell therapy bank. Modified cells resistant to an immunosuppressive treatment can be obtained by any of the method described herein. A desirable cell population can also be selected prior to modification. An engineered cell population can also be selected after modification. An engineered cell can be used in autologous transplantation. Alternatively, a cell can be used in allogeneic transplantation. In some instances, a cell is administered to the same patient whose sample was used to identify the cancer-related target sequence. In other instances, a cell is administered to a patient different from the patient whose sample was used to identify the cancer-related target sequence.

In some cases, an immune responsive cell can be a primary cell including primary T cell, a stem cell, or a progenitor cell. A progenitor cell can be a hematopoietic progenitor cell. A cell of the present invention can be a human cell. Suitable cells can be expanded ex vivo. A suitable cell can also be CD45RO(−), CCR7(+), CD45RA (+), CD62L(+), CD27(+), CD28(+), IL-7Ra(+), or combinations thereof.

In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cells including any T-cell such as tumor infiltrating cells (TILs), such as CD3+ T-cells, CD4+ T-cells, CD8+ T-cells, or any other type of T-cell. The T cell can also include memory T cells, memory stem T cells, or effector T cells. The T cells can also be selected from a bulk population, for example, selecting T cells from whole blood. The T cells can also be expanded from a bulk population. The T cells can also be skewed towards particular populations and phenotypes. For example, the T cells can be skewed to phenotypically comprise, CD45RO (−), CCR7 (+), CD45RA (+), CD62L (+), CD27 (+), CD28 (+) and/or IL-7Ra (+). Suitable cells can be selected that comprise one of more markers selected from a list comprising: CD45RO (−), CCR7 (+), CD45RA (+), CD62L (+), CD27 (+), CD28 (+) and/or IL-7Rα (+). Suitable cells also include stem cells such as, by way of example, embryonic stem cells, induced pluripotent stem cells, hematopoietic stem cells, neuronal stem cells and mesenchymal stem cells. Suitable cells can comprise any number of primary cells, such as human cells, non-human cells, and/or mouse cells. Suitable cells can be progenitor cells. Suitable cells can be derived from the subject to be treated (e.g., patient). Suitable cells can be derived from a human donor. Suitable cells can be stem memory $T_{SCM}$ cells comprised of CD45RO (−), CCR7(+), CD45RA (+), CD62L+(L-selectin), CD27+, CD28+ and IL-7Rα+, said stem memory cells can also express CD95, IL-2Rβ, CXCR3, and LFA-1, and show numerous functional attributes distinctive of said stem memory cells. Suitable cells can be central memory $T_{CM}$ cells comprising L-selectin and CCR7, said central memory cells can secrete, for example, IL-2, but not IFNγ or IL-4. Suitable cells can also be effector memory T$_{EM}$ cells comprising L-selectin or CCR7 and produce, for example, effector cytokines such as IFNγ and IL-4.

In some cases, a method can include enriching cultured T cells for CD8$^+$ T cells prior to rapid expansion of cells. Following culture of T cells in IL-2, the T cells can be depleted of CD4$^+$ cells and enriched for CD8$^+$ cells using, for example, a CD8 microbead separation (e.g., using a CliniMACS$^{plus}$ CD8 microbead system (Miltenyi Biotec)). Without being bound to a particular theory, it can be believed that CD4$^+$, CD25$^+$ regulatory T-cells can impede anti-tumor responses. Accordingly, it can be believed that enriching cultured T cells for CD8$^+$ T cells and reducing or eliminating CD4$^+$ cells may improve the impact of adoptively transferred anti-tumor CD8$^+$ cells, improve the response rates in patients, and/or reduce the toxicities seen by production of cytokines by CD4$^+$ cells. Additionally, enriched CD8$^+$ "young" T cells can be believed to behave more reliably and predictably in clinical scale rapid expansions than the bulk T cells.

A cell can be a good manufacturing practices (GMP) compatible reagent. A cell can be part of a combination therapy to treat cancer, infections, autoimmune disorders, or graft-versus-host disease (GVHD) in a subject in need thereof. In some cases, a cell of the present invention can be administered of a subject in need thereof as a monotherapy.

In some cases, cells expressing a subject CAR include heterogeneous T cell populations. In some cases, cells used can be largely composed of a heterogeneous proportion of CD4 and CD8 T cells. Said CD4 and CD8 cells can have phenotypic characteristics of circulating effector T cells. Said CD4 and CD8 cells can also have a phenotypic characteristic of effector-memory cells. In another embodiment, cells can be central-memory cells.

Suitable cells that can be isolated from a donor can be at any stage of development including, but not limited to, fetal, neonatal, young and adult. For example, donor immunoresponsive cells can be isolated from adult human Donor human immunoresponsive cells can be under the age of 10, 9, 8, 7, 6, 5, 4, 3, 2, or 1 year(s). For example, immunoresponsive cells can be isolated from a human under the age of 6 years Immunoresponsive cells can also be isolated from a human under the age of 3 years. A donor can be older than 10 years.

A method of attaining suitable cells can comprise selecting based on a given marker. For example, such marker can comprise GFP, a resistance gene, a cell surface marker, or an endogenous tag. Cells can be selected using any endogenous marker. Applicable cell selection techniques include flow cytometry and/or magnetic columns. Selected cells can subsequently be infused into a subject. Selected cells can also be expanded to large numbers. Selected cells can be expanded prior to infusion.

The amount of cells that are necessary to be therapeutically effective in a patient may vary depending on the viability of the cells, and the efficiency with which the cells have been genetically modified (e.g., the efficiency with which a transgene has been integrated into one or more cells, or a level of expression of a protein encoded by the transgene). In some cases, the product (e.g., multiplication) of the viability of cells post genetic modification and the efficiency of integration of a transgene may correspond to the therapeutic aliquot of cells available for administration to a subject. In some cases, an increase in the viability of cells post genetic modification may correspond to a decrease in the amount of cells that are necessary for administration to be therapeutically effective in a patient. In some cases, an increase in the efficiency with which a transgene has been integrated into one or more cells may correspond to a decrease in the amount of cells that are necessary for administration to be therapeutically effective in a patient. In some cases, determining an amount of cells that are necessary to be therapeutically effective may comprise determining a function corresponding to a change in the viability of cells over time. In some cases, determining an amount of cells that are necessary to be therapeutically effective may comprise determining a function corresponding to a change in the efficiency with which a transgene may be integrated into one or more cells with respect to time dependent variables (e.g., cell culture time, electroporation time, cell stimulation time). In some cases, therapeutically effective cells can be a population of cells that comprise from about 30% to about 100% expression of an anti-GPC3 CAR on a cellular surface. In some cases, therapeutically effective cells can express an anti-GPC3 CAR on a cellular surface from about 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, to more than about 99.9% as measured by flow cytometry.

A variety of cells can be used to express the subject CAR, as described above. Anti-GPC3 CAR can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell.

When present in the plasma membrane of a eukaryotic cell, a CAR can be active in the presence of its binding target. For example, an anti-GPC3 CAR can be active in the presence of GPC3. A target, such as GPC3, can be expressed on a membrane. A target can also be soluble (e.g., not bound to a cell). A target can be present on the surface of a cell such as a target cell. A target can be presented on a solid surface such as a lipid bilayer; and the like. A target can be soluble, such as a soluble antigen. A target can be an antigen. An antigen can be present on the surface of a cell such as a target cell. An antigen can be presented on a solid surface such as a lipid bilayer; and the like. In some cases, a target can be an epitope of an antigen. In methods disclosed herein, the antigen is typically GPC3 and the GPC3 expressing target cell is a cancer or tumor cell.

In some instances, a CAR, when present on the plasma membrane of a cell, and when activated by binding its target, can result in cytotoxic activity by the cell toward a target that expresses on its cell surface an antigen to which the binding domain of the CAR binds. For example, in some cases a cell can be a cytotoxic cell (e.g., an NK cell or a cytotoxic T lymphocyte), a CAR of the present disclosure, when present in the plasma membrane of a cell, and when activated by binding its target, can increase cytotoxic activity of a cytotoxic cell toward a target cell that expresses on its cell surface an antigen to which the binding domain of a CAR binds. For example, in some cases a cell can be an NK cell or a T lymphocyte, a CAR of the present disclosure, when present in the plasma membrane of a cell, and when activated by binding of its target, can increase cytotoxic activity of a cell by at least 10%, at least 15%, at least 20%, at least 25%, at least 30%, at least 40%, at least 50%, at least 75%, at least 2-fold, at least 2.5-fold, at least 5-fold, at least 10-fold, or more 10-fold, compared to the cytotoxic activity of the cell in the absence of the binding target.

In some cases, a CAR, when activated by binding its target, can result in other CAR activation related events such as proliferation and expansion (either due to increased cellular division or anti-apoptotic responses). Cellular proliferation can be visually measured by the observance of cellular clumping as seen under a microscope. Cellular expansion can be measured by a hemocytometer measurement. In some cases, a CAR-T cell can have increased cellular proliferation and expansion when compared to a comparable T cell, a non-CAR T cell. Increased cellular expansion can be from about 1 fold to about 20 hold over that of a comparable cell. Increased cellular expansion can be from about 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 16 fold, 17 fold, 18 fold, 19 fold, or up to 20 fold over that of a comparable cell. Cellular expansion can be measured over a period of time. For example, cellular expansion can take place from cellular acquision to the time of infusion into a subject. In other cases, cellular expansion can take place from about 1 day to up to about 30 days after acquisition. Cellular expansion can take place from about 1, 2, 3, 4, 5, 6, 7, 8, 9, 10, 11, 12, 13, 14, 15, 16, 17, 18, 19, 20, 21, 22, 23, 24, 25, 26, 27, 28, 29, or up to 30 days after acquisition. In some cases, a rapid expansion protocol (REP) can be utilized to expand cells prior to infusion into a subject. A REP can occur over a period of about 14 days in some cases.

In some cases, a CAR, when activated by binding its target, can result in other CAR activation related events such as intracellular signaling modulation, cellular differentiation, or cell death. In some cases, expression of a CAR on a cell may alter intracellular signaling of a cell. In other cases, expression of a CAR may alter cellular differentiation.

Subject anti-GPC3 CAR immunoresponsive cells can be administered to a subject exhibiting a GPC3 expressing cancer or tumor either concurrently or after a lymphocyte reduction treatment.

In some aspects, anti-GPC3 CAR immunoresponsive cells are administered after a lymphocyte reduction treatment. The treatment can reduce the circulating lymphocytes in a treated subject, or substantially deplete the circulating lymphocytes the lymphocyte (i.e., lymphocyte reduction). For example, anti-GPC3 CAR immunoresponsive cells can be administered at least 1 hour to at least 1 week after a lymphocyte reduction treatment. For example, anti-GPC3 CAR immunoresponsive cells can be administered at least 1 hour, 2 hours, 4, hours, 6, hours, 8 hours, 10 hours, 12, hours, 14 hours, 16 hours, 18 hours, 20 hours, 24 hours, 36 hours, 48 hours, 3 days, 4 days, 5 days, 6 days, or 7 days or longer after lymphocyte reduction treatment. In some cases, CAR-T can be administered about 1, 2, 3, 4, 5, 6 weeks, or longer after a lymphocyte reduction treatment.

In some cases, host lymphopenia can facilitate expansion of anti-GPC3 CAR immunoresponsive cells, such as CAR T cells. On the one hand, lymphopenia can create "space" for oncoming adoptively transferred cells and, on the other, it can induce their homeostatic expansion. The latter effect can be likely mediated through chemotherapeutic ablation of endogenous regulatory T cells, which can normally secrete inhibitory cytokines (e.g. TGF-β and IL-10) that can limit effector cell expansion, such as CAR T cells. In some cases, a lymphocyte reduction treatment can improve expansion of anti-GPC3 CAR immunoresponsive cells in vivo by about 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 16 fold, 17 fold, 18 fold, 19 fold, or up to 20 fold over treatment with anti-GPC3 CAR immunoresponsive cells without a lymphocyte reduction treatment.

Additionally, T-cell growth homeostatic cytokines, such as IL-7 and IL-15, which may ordinarily exist in limiting amounts, may become readily available due to less competition and increased production by lymphopoietic stromal cells. Thus, induction of lymphocyte reduction prior to infusion of anti-GPC3 CAR immunoresponsive cells may be performed to increase efficacy of anti-GPC3 CAR immunoresponsive cells in treating a subject. In some cases, a lymphocyte reduction treatment may improve anti-tumor efficacy as measured by tumor reduction or control by about 10% to about 100% over treatment without a lymphocyte reduction treatment. For example a lymphocyte reduction treatment may improve anti-tumor efficacy from about 10%, 15%, 20%, 25%, 30%, 35%, 40%, 45%, 50%, 55%, 60%, 65%, 70%, 75%, 80%, 85%, 90%, 95%, or up to 100% over treatment without a lymphocyte reduction treatment.

A lymphocyte reduction can be performed using various means. Lymphocyte reduction before anti-GPC3 CAR immunoresponsive cells administration can be performed using total body irradiation (TBI) or cytotoxic drugs. Although these modalities may intended to deplete the lymphoid compartment of a recipient, they can also facilitate the presentation of tumor antigens by triggering tumor cell death and antigen release. Subsequently, these antigens can be taken up and presented by antigen presenting cells (APCs) to enhance the activation of anti-GPC3 CAR immunoresponsive cells.

Irradiation and/or chemotherapy can lead to activation of host cells, resulting in the release of proinflammatory cytokines, such as TNF-α, IL-1 and IL-4, and upregulation of co-stimulatory molecules, such as CD80. In some cases, a lymphocyte reduction treatment may improve anti-GPC3 CAR immunoresponsive cell therapy by activation of host cells. In some cases, a lymphocyte reduction treatment may improve anti-GPC3 CAR immunoresponsive cell therapy by upregulation of co-stimulatory molecules. In addition to enhanced APC function and availability, a preconditioning regimen can damage the integrity of mucosal barriers through radiation-induced apoptosis of cells lining these organs. Damage inflicted on the intestinal tract might permit the translocation of bacterial products, such as LPS, into the systemic circulation. LPS can in turn activate anti-GPC3 CAR immunoresponsive cells in vivo and might enhance the antitumor response. Thus, proinflammatory cytokines and microbial products provide crucial 'danger signals' for the activation and maturation of DCs, thus enhancing anti-GPC3 CAR immunoresponsive cell-mediated tumor treatment.

In some cases, a lymphocyte reduction treatment can selectively deplete CD25-expressing cells in humans, including humanized anti-Tac (anti-CD25) and ONTAK™ (IL-2 conjugated to diphtheria toxin).

In some cases, a chemotherapeutic can be administered to effect lymphocyte reduction in a subject. In some cases, a subject may receive nonmyeloablative lympho-reduction chemotherapy. A nonmyeloablative lympho-reduction chemotherapy can be any suitable such therapy, which can be administered by any suitable route. Chemotherapeutic regimens may include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin).

A nonmyeloablative lympho-reduction chemotherapy can comprise, for example, administration of cyclophosphamide and fludarabine, particularly if a cancer is GPC3 positive, which can be metastatic. A preferred route of administering cyclophosphamide and fludarabine can be intravenously. Likewise, any suitable dose of cyclophosphamide and fludarabine can be administered. Preferably, around 60 mg/kg of cyclophosphamide can be administered for two days after which around 25 mg/m$^2$ fludarabine can be administered for about five days.

In some cases, lymphocyte reduction can be performed to minimize immune-mediated anti-GPC3 CAR immunoresponsive cell rejection. For example, a subject can be treated with cyclophosphamide (Cy) followed by fludarabine (Flu) lymphocyte reduction treatment. A dose of a chemotherapeutic such as Cy can be from about 1 mg/kg to about 200 mg/kg. A dose of Cy can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 79 80, 81, 82, 83, 84, 85, 86, 87, 88, 89, 90, 95, 100, 110, 120, 130, 140, 150, 160, 170, 180, 190, or up to about 200 mg/kg of a subject.

Alternatively, an exemplary dose and regimen for Cy treatment can be from about 0.5~5 g/m$^2$/day, preferably 0.6~3 g/m$^2$/d, more preferably 1~2 g/m$^2$/day, for 1-3 days, preferably 1-2 days;

A dose of Flu can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 79 80, 81, 82, 83, 84, 85, 86, 87, 88, 89, 90, 95, 100, 110, 120, 130, 140, 150, 160, 170, 180, 190, or up to about 200 mg/m$^2$ of a subject.

Alternatively, an exemplary dose and regimen for fludarabine treatment can be from about 20~80 mg/m$^2$/day, preferably 25~70 mg/m$^2$/day or 25~30 mg/m$^2$/day, for 2~10, 3~8 or 4, 5, 6 or 7 days;

In some cases, combined use of Cy and Flu can be applied. For example, initial dose of Flu in the range of about 10~60 mg/m$^2$/day or 15~50 mg/m$^2$/day or 20~30 mg/m$^2$/day for 2~8 days or 3~6 days, is followed by Cy in the amount of about 0.2~1 mg/m$^2$/day or 0.3~0.8 mg/m$^2$/day or 0.4~0.6 g/m$^2$/day for 1-5 or 2-3 days.

In some cases, a subject can be treated with Cy and Flu at Cy 60 mg/kg×1 administration and Flu 25 mg/m$^2$×3 to 5 administrations before anti-GPC3 CAR immunoresponsive cell infusion. A subject can receive from about 0 to about 20 administrations of a lymphodepletant before an anti-GPC3 CAR immunoresponsive cell infusion. A subject can receive from about 0, 1, 2, 3, 4, 5, 6, 7, 8, 9, 10, 11, 12, 13, 14, 15, 16, 17, 18, 19, up to about 20 administrations of a lymphodepletant, such as Cy or Flu, prior to anti-GPC3 CAR immunoresponsive cell infusion. In other cases, a subject may be co-administered a lymphodepletant, such as Cy and/or Flu, concurrent with anti-GPC3 CAR immunoresponsive cell infusion. In other cases, a subject may be administered a lymphodepletant, such as Cy and/or Flu, after an anti-GPC3 CAR immunoresponsive cell administration. In other cases, a subject may be administered a lymphodepletant prior, concurrent, and/or after an anti-GPC3 CAR immunoresponsive cell administration. A subject may not receive a lymphocyte reduction treatment is some cases. In some cases, different doses of lymphodepletants may be used during the course of a regime. For example, a subject may receive 60 mg/kg of Cy prior to anti-GPC3 CAR immunoresponsive cells, followed by a dose of 40 mg/kg of Cy concurrent with anti-GPC3 CAR immunoresponsive cells. A complete blood count (CBC) may be performed to determine the extent of lymphocyte reduction and if additional administrations may be required. In some cases, Cy may be administered alone. In other cases, Flu may be administered alone. In some cases, Cy and Flu may be alternated during a regime.

Lymphocyte reduction may improve anti-GPC3 CAR immunoresponsive cell expansion. Lymphocyte reduction may improve anti-GPC3 CAR immunoresponsive cell persistence in blood. Anti-GPC3 CAR immunoresponsive cell expansion and persistence may be detected by flow cytometric analysis utilizing an anti-CAR antibody. Anti-GPC3 CAR immunoresponsive cell persistence may also be measured by evaluating copy number of anti-GPC3 CAR immunoresponsive cell by qPCR.

In some cases, a subject may receive a reduction in anti-GPC3 CAR immunoresponsive cell dose if subject to a lymphocyte reduction treatment compared to a subject that may not receive a lymphocyte reduction treatment.

In some cases, a lymphocyte reduction treatment can be administered over a period of time. For example a lymphocyte reduction treatment may be administered over the course of 1 min up to about 24 hours. A lymphocyte reduction treatment may be performed from 1 min, 15 min, 45 min, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or up to about 24 hours. Lympho-reduction agents may be coadministered with additional agents such as diluents, uroprotectants, excipients, or a combination thereof. For example, sodium 2-mercaptoethanesulfonate (Mesna) may be included in a lymphocyte reduction treatment. In some cases, a subject may be administered cyclophosphamide 60 mg/kg/day for about 2 days IV in 250 ml D5W with Mesna 15 mg/kg/day for 2 days over 1 hr. Mesna may be coadministered with a lymphodepletant at various doses. For example, Mesna may be administered from about 1 mg/kg/day up to about 50 mg/kg/day. Mesna may be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or up to about 50 mg/kg/day. In some cases, for obese or pediatric subjects a drug dosage may be calculated using practical weight. Practical weight may be an average of an actual weight and an ideal body weight. For example, ideal body weight may be calculated for a male=50 kg+2.3 (number of inches over 60 inches). An ideal body weight may be calculated for a female=45.5 kg+2.3 (number of inches over 60 inches). In some cases, a Flu administration can be 25 mg/m$^2$/day IVPB daily over 30 minutes for 5 days. In some cases, a Flu administration can occur before a Cy administration. In some cases, a Flu administration can be performed concurrent with Cy. In some cases, a Flu administration can be performed after a Cy administration. In some cases, fludarabine can be started approximately 1 to 2 hours after the Cy and mesna.

Total body irradiation can be a form of radiotherapy. As the name implies, TBI can involve irradiation of the entire body, though in modern practice the lungs can be partially shielded to lower the risk of radiation-induced lung injury. Total body irradiation can be administered at various doses. For example, total body irradiation can be administered from about 10 to about 12 Gy. In some cases, total body irradiation can be fractionated, with smaller doses delivered in several sessions, rather than delivering the entire dose at once. In some cases, 1, 2, 3, 4, 5, 6, 7, 8, 9, or up to 10 different doses of irradiation can be administered.

The reported $D_0$ value—the amount of ionizing radiation necessary to eradicate a particular cell type—of hematopoietic stem cells can be from about 0.5 to about 1.4 Gy, while those of human leukemia cell lines can be from about 0.8 to about 1.5 Gy, indicating that both cells are radiosensitive. The ideal dosing schedule can depend on patient age, disease and the intended type of treatment. Myeloablative TBI can be from about 12 to about 15 Gy given in about 8 to about 12 fractions over about 4 days, with about 2 to about 3 treatments daily. In some cases, myeloablative TBI can be from about 5 to about 20 Gy. Myeloablative TBI can be from about 5, 6, 7, 8, 9, 10, 11, 12, 13, 14, 15, 16, 17, 18, 19, to about 20 Gy. In some cases, myeloablative TBI can be given in about 5 to about 20 fractions. Myeloablative TBI can be given in about 5, 6, 7, 8, 9, 10, 11, 12, 13, 14, 15, 16, 17, 18, 19, to about 20 fractions. Myeloablative therapy can be given over about 1 to about 10 days. Myeloablatic therapy can be administered over about 1, 2, 3, 4, 5, 6, 7, 8, 9 or up to about 10 days.

In some cases, a low-dose TBI can include doses of about 2 to about 8 Gy given in about 1 to about 4 fractions. In some cases, a low-dose TBI can include doses of about 0.5, 1, 1.5, 2, 2.5, 3, 3.5, 4, 4.5, 5, 5.5, 6, 6.5, 7, 7.5, or up to about 8 Gy. A low-dose TBI can be administered to a subject who may not tolerate myeloablation due to age or comorbidity.

TBI can be administered using parallel opposed pairs of high-energy photon beams from about 4 to about 18 MV for TBI. In some cases, photon beams can be from about 1 to about 25 MV for TBI. Photon beams can be from about 1, 2, 3, 4, 5, 6, 7, 8, 9, 10, 11, 12, 13, 14, 15, 16, 17, 18, 19, 20, 21, 22, 23, 24, or up to about 25 MV. TCI can be performed using equipment such as a Varian Clinac iX or a Siemens Artiste.

In some cases a rate of administration can be from about 5 cGy/min to about 100 cGy/min. A Rate of administration can be from about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 79 80, 81, 82, 83, 84, 85, 86, 87, 88, 89, 90, 95, or up to 100 cGy/min.

In some cases, certain organs can be shielded during radiation. For example, a liver, lung, brain, heart, or a combination thereof may be shielded during total body irradiation.

Biological Agents

In some cases, a biological agent such as an antibody can be used to deplete immune cells. Monoclonal antibodies (mAbs) that are cytolytic for lymphocytes may be an alternative means of yielding lymphocyte reduction. In some cases, an antibody for T-cell lymphocyte reduction that may be administered before anti-GPC3 CAR immunoresponsive cell infusion should be effective but short lived in vivo, to permit rapid infusion and repopulation with infused anti-GPC3 CAR immunoresponsive cells. Antibodies used can be directed to markers expressed on a surface of a cell, such as a lymphocyte. In some cases, lympho-reduction antibodies can be anti-CD3, anti-CD4, anti-CD8, anti-CD45, anti-CD25, anti-CD52, and any combination thereof.

Antibodies such as Alemtuzumab (Campath-1H), Bortezomib, thymoglobulin (rabbit ATG, Genzyme), ATGAM (equine ATG, Pfizer), and alemtuzumab (Campath-1H) can be used. Rituximab (IDEC-C2B8), GA101, a humanized IgG1 to CD20, XmAb5574, an Fc-engineered antibody to CD19, alefacept (LFA3-Ig), fingolimod (FTY720), antithymocyte globulin (ATG), anti-CD4 antibodies, anti-CD3 antibodies, anti-CD8 antibodies, can also be used as a lymphocyte reduction agent. In some cases, Cladribine (2-CdA, Leustatin®), a purine analog similar to fludarabine, can be used. In some cases, an antibody lymphocyte reduction treatment can include a single antibody such as alemtuzumab (anti-CD52). In other cases, an antibody-based lymphocyte reduction treatment can include at least two antibodies, such as alemtuzumab and anti-CD45. In some cases, a lymphocyte reduction treatment can include multiple lympho-reduction modalities, such as radiation combined with an antibody therapy or a chemotherapy combined with radiation. Chemotherapy and antibody therapy may also be used in combination.

Antibiotics, Anti-fungals and Anti-virals can be given to subjects as prophylaxis during a lymphocyte reduction treatment. For example, a prophylaxis may include Altrex 500 mg daily, Bactrium DS one tablet q M W F and Fluconazole 200 mg daily. The duration of medication is until Absolute Lymphocyte count (ALC) and Absolute Neutrophil Count (ANC) count may return to pre medication baseline. A biological agent can also be Adriamycin.

One or more cytokines can be introduced with cells. Cytokines can be utilized to boost transferred cells (including adoptively transferred tumor-specific cells) to expand within a tumor microenvironment. In some cases, IL-2 can be used to facilitate expansion of the cells described herein. Cytokines such as IL-15 can also be employed. Other relevant cytokines in the field of immunotherapy can also be utilized, such as IL-2, IL-7, IL-12, and, L-21, or any combination thereof. In some cases, recombinant cytokines are used.

In some cases, a T-cell growth factor can be administered. A growth factor can be administered by any suitable route. If more than one T-cell growth factor is administered, they can be administered simultaneously or sequentially, in any order, and by the same route or different routes. A T-cell growth factor, such as Aldesleukin (IL-2), can be administered intravenously as a bolus injection. A dosage of a T-cell growth factor, such as IL-2, is what is considered by those of ordinary skill in the art to be high. Preferably, a dose of about 720,000 IU/kg of IL-2 can be administered three times daily until tolerance. Is come cases, about 5 to about 15 doses of IL-2 are administered, with an average of around 9 doses. A dosage of a T cell growth factor can be from about 0 to about 20. A T cell growth factor can be administered 1, 2, 3, 4, 5, 6, 7, 8, 9, 10, 11, 12, 13, 14, 15, 16, 17, 18, 19, or up to about 20 times.

IL-2 can be administered at a dose of 720,000 IU/kg (based on total body weight) as an intravenous bolus. In some cases, IL-2 can be administered over a 15-minute period. In some cases, IL-2 can be administered over a 20-minute period. IL-2 can be administered by immediate injection. In some cases IL-2 can be administered over 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 1 hour, 2 hours, 3 hours, 4 hours, 5 hours, or up to a period of 6 hours.

In some cases, IL-2 can be administered beginning within 24 hours of cell infusion and continuing for up to about 4 days (maximum 12 doses). In some cases, IL-2 can be administered for up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 days after an initial administration.

Doses of IL-2 can be administered every eight hours. In some cases, IL-2 can be administered from about every 1, 2, 3, 4, 5, 6, 7, 8, 9, 10, 11, 12, 13, 14, 15, 16, 17, 18, 19, 20, 21, 22, 23, 24 hours after an initial administration. In some cases, IL-2 dosing can be stopped if toxicities are detected. In some cases, doses can be delayed or stopped if patients reach Grade 3 or 4 toxicity due to aldesleukin except for the reversible Grade 3 toxicities common to Aldesleukin such as diarrhea, nausea, vomiting, hypotension, skin changes, anorexia, mucositis, dysphagia, or constitutional symptoms and laboratory changes. In some cases, if these toxicities can be easily reversed within 24 hours by supportive measures, then additional doses may be given. In addition, dosing may be held or stopped at the discretion of the treating physician.

In some cases, an immunoresponsive cell that expresses an anti-GPC3 CAR can have increased anti-tumor efficacy compared to a comparable immunoresponsive cell that does not express the anti-GPC3 CAR.

In some cases, anti-tumor efficacy can refer to cytotoxic activity. In other cases, anti-tumor efficacy can refer to persistence. Anti-tumor efficacy can also refer to the ability of a cell to target a tumor. Anti-tumor efficacy can be measured using various in vitro assays. For example, cytotoxic ability can be measured by an ELISA that measures release of interleukin-2 (IL-2) or Interferon-γ (IFNγ). Cytotoxic activity can be measured by a killing assay such as a chromium-51 release assay or a co-culture assay. In some cases, anti-GPC3 CAR immunoresponsive cells can have increased anti-tumor efficacy and ability when compared to comparable cells.

An anti-GPC3 CAR treatment efficacy can be evaluated using multiple modalities. Efficacy can refer to anti-tumor efficacy that is the extent to which a tumor, such as a GPC3-positive tumor, is controlled, reduced, or eliminated. Treatment efficacy can also refer to CAR immunoresponsive cell expansion, persistence, tumor-targeting, and any combination thereof.

A subject that can be administered an anti-GPC3 CAR immunoresponsive cell therapy, such as anti-GPC3 CAR T cell therapy, can be evaluated during an infusion, immediately after an infusion, or up to years following an infusion. For example, a treated subject can return to a clinic for evaluation for a period of about 1 day to the length of the subject's life. A treated subject can be evaluated from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, or up to 90 years after an initial administration of the subject CAR immunoresponsive cells. In some cases, an evaluation schedule can include daily monitoring, weekly monitoring, monthly monitoring, or yearly monitoring. In some cases, a subject can be seen more frequently as clinically indicated. An evaluation can include a physical exam, chemistry evaluation, complete blood count, thyroid panel, toxicity assessment, computerized tomography (CT) scan of a bodily area, apheresis, and any combination thereof.

In some cases, apheresis may be performed prior to and from about 1 to about 10 weeks following administration of a subject CAR immunoresponsive cell infusion. At other time points, a subject's peripheral blood lymphocytes (PBL) can be obtained from whole blood by purification using centrifugation on a Ficoll gradiant. Aliquots of peripheral blood mononuclear cells (PBMC5) can be cryopreserved for immunological monitoring of cell function. In some cases, a variety of tests can include evaluation of specific lysis and cytokine release, metabolomic and bioenergetic studies (using Seahorse), intracellular FACS of cytokine production, ELISA-spot assays, and lymphocyte subset analysis may be used to evaluate the immunological correlates of a subject CAR immunoresponsive cell treatment. In general, differences of about 2 to about 3 fold in these assays may be indicative of true biologic differences. In some cases, different of about 1, 1.5, 2, 2.5, 3, 3.5, 4, 4.5, up to about 5 fold of in vitro assays, post anti-GPC3 CAR immunoresponsive cell therapy, may be indicative of treatment efficacy.

In some cases, a subject CAR immunoresponsive cell treatment may reduce tumor size by at least 30% as measured by computerized tomography (CT) scan or an MRI. An anti-GPC3 CAR immunoresponsive cell treatment may reduce tumor size by at least about 5%, 10%, 15%, 20%, 25%, 30%, 35%, 40%, 45%, 50%, 55%, 60%, 65%, 70%, 75%, 80%, 85%, 90%, 95%, or up to about 100%. A CAR-T treatment may eliminate a tumor as measured by CT scan. In some cases, an anti-GPC3 CAR immunoresponsive cell treatment may stabilize a tumor size as measured by a less than 10% change in a baseline measurement of a diameter of a tumor lesion as measured by computerized tomography (CT) scan. For example, a tumor may not expand in size after administration of anti-GPC3 CAR immunoresponsive cells. In some cases, stabilization may be considered a less than 10%, 9%, 8%, 7%, 6%, 5%, 4%, 3%, 2%, or 1% change in tumor size as compared to a pre-treatment measurement.

In some cases, anti-GPC3 CAR immunoresponsive cell efficacy can be considered in terms of subject survival time. For example, a subject that is treated with anti-GPC3 CAR immunoresponsive cells, such as an anti-GPC3 CAR T cells, can survive longer than an untreated subject or a subject treated with a different therapy.

In some cases, anti-GPC3 CAR immunoresponsive cell efficacy can be improved by the addition of a secondary treatment, such as lymphocyte reduction treatment. A secondary treatment can synergize with a anti-GPC3 CAR immunoresponsive cell therapy. In some cases, a secondary treatment can produce additive effects of anti-GPC3 CAR immunoresponsive cell therapy. A secondary treatment can be lymphocyte reduction as well as additional forms of cellular therapy, antibody therapy, chemotherapy, radiation therapy, surgery, anti-angiogenic therapy, and any combination thereof.

Treatment response can be evaluated using the international criteria proposed by the revised Response Evaluation Criteria in Solid Tumors (RECIST) guideline (Version 1.1). Changes in the largest diameter (unidimensional measurement) of a tumor lesion and the shortest diameter in the case of malignant lymph nodes can be used in the RECIST criteria. For example, measurable lesions can be those defined as those that can be accurately measured in at least one dimension (longest diameter to be recorded) as >20 mm by chest x-ray, as >10 mm with CT scan, or >10 mm with calipers by clinical exam. To be considered pathologically enlarged and measurable, a lymph node can be >15 mm in short axis when assessed by CT scan. All other lesions (or sites of disease), including small lesions (longest diameter <10 mm or pathological lymph nodes with ≥10 to <15 mm short axis), can be considered non-measurable disease. Bone lesions, leptomeningeal disease, ascites, pleural/pericardial effusions, lymphangitis cutis/pulmonitis, inflammatory breast disease, can be considered as non-measurable.

All measurable lesions up to a maximum of 2 lesions per organ and 5 lesions in total, representative of all involved organs, can be identified as target lesions and recorded and measured at baseline. Target lesions can be selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion which can be measured reproducibly should be selected. A sum of the diameters (longest for non-nodal lesions, short axis for nodal lesions) for all target lesions can be calculated and reported as the baseline sum diameters. If lymph nodes are to be included in the sum, then only the short axis can be added into the sum. A baseline sum diameter will be used as reference to further characterize any objective tumor regression in the measurable dimension of the disease.

In some cases, a clinical lesion can be considered measurable when it can be superficial (e.g., skin nodules and palpable lymph nodes) and about 10 mm diameter as assessed using calipers (e.g., skin nodules). In cases, where a caliper cannot be used to measure a lesion, a CT scan or MRI can also be used. In some cases, a CT scan can yield slices of tissue from about 5 mm or less. A CT scan can have 5 mm, 4 mm, 3 mm, 2 mm, 1 mm or 0.5 mm scan thickness in some cases. If a CT scan has a slice thickness greater than 5 mm, a minimum size for a measurable lesion can be twice the slice thickness. In some cases, an MRI can also be performed to evaluate a subject. Ideally, the same type of scanner should be used and the image acquisition protocol should be followed as closely as possible to prior scans when determining treatment efficacy. Body scans should be performed with breath-hold scanning techniques, if possible. In some cases, a fluorodeoxyglucose (FDG)-positron emission tomography (PET) can be used to measure treatment efficacy.

Once a subject has been evaluated, target lesions can be grouped into stable disease (SD), progressive disease (PD), partial response (PR), and/or a complete response (CR). A SD can be considered neither sufficient shrinkage to qualify for PR nor sufficient increase to qualify for PD, taking as reference the smallest sum of diameters. A PD can be considered at least a 20% increase in the sum of the diameters of target lesions, taking as reference the smallest sum (this can include the baseline sum if that may be the smallest). In some cases, in addition to a relative increase of about 20%, a sum must also demonstrate an absolute increase of at least about 5 mm. A PR can be at least about 30% decrease in a sum of the diameters of target lesions, taking as reference the baseline sum of diameters. A CR can be elimination of target lesions.

In some cases, administration of anti-GPC3-CAR immunoresponsive cells, such as anti-GPC3 CAR T cells, and a lymphocyte reduction treatment can synergistically increase a subject's median survival time by at least about 6 months as compared to administering the anti-GPC3-CAR immunoresponsive cells alone, Table 6. In some cases, a combination of an anti-GPC3-CAR immunoresponsive cell therapy and a lymphocyte reduction treatment can synergistically increase a subject's survival time by at least about 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, or up to about 25 years as compared to administering the anti-GPC3-CAR immunoresponsive cells alone.

TABLE 6

Construct Comparison

| CAR-T Construct | Survival | Response | Lymphocyte reduction treatment |
|---|---|---|---|
| 35-28Z | 2.8 | PD | No |
| 33-28Z | 6.6 | PD | No |
| 33-28Z | 8.8 | PD | No |
| Median OS = 6.6 Mo | | | |
| 33-28Z/33-28BBZ | 3.6 | SD | Yes |
| 35-28Z | 11.1+ | Unknown | Yes |
| 35-28Z | 11.3+ | Unknown | Yes |
| 35-28Z | 11.7+ | PD | Yes |
| 33-28Z/35-28Z | 12.3 | PD | Yes |
| 35-28Z | 15.2+ | SD | Yes |
| 35-28Z | 15.2+ | PR | Yes |
| 33-28Z/33-28BBZ | 21.1 | SD | Yes |
| 33-28Z/35-28Z | 21.4 + | SD | Yes |
| Median OS is not reached current at 12.3 Mo | | | |

Subject anti-GPC3 CAR immunoresponsive cells can be formulation into a pharmaceutical medicament and be used to treat a human or mammal, in need thereof, diagnosed with a disease, e.g., cancer. These pharmaceutical medicaments can be co-administered to a human or mammal, together with one or more chemotherapeutic agent or chemotherapeutic compound.

Populations of subject CAR immunoresponsive cells, such as CAR T cells, may be formulated for administration to a subject using techniques known to the skilled artisan. Formulations comprising populations of CAR immunoresponsive cells may include pharmaceutically acceptable excipient(s). Excipients included in the formulations will have different purposes depending, for example, on the subpopulation of T cells used and the mode of administration. Examples of generally used excipients included, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising populations of CAR immunoresponsive cells will typically have been prepared and cultured in the absence of any non-human components, such as animal serum. A formulation may include one population of CAR immunoresposive cells, or more than one, such as two, three, four, five, six or more populations of CAR immunoresposive cells. For example, a formulation may include one population of CAR T cells, or more than one, such as two, three, four, five, six or more populations of CAR T cells.

Formulations comprising population(s) of anti-GPC3 CAR immunoresponsive cells may be administered to a subject using modes and techniques known to the skilled artisan. Exemplary modes include, but are not limited to, intravenous injection. Other modes include, without limitation, intratumoral, intradermal, subcutaneous (S.C., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection of infusion of the formulations can be used to effect such administration.

Formulations comprising population(s) of CAR immunoresponsive cells that are administered to a subject comprise a number of CAR immunoresponsive cells that is effective for the treatment and/or prophylaxis of the specific indication or disease. Thus, therapeutically-effective populations of CAR immunoresponsive cells can be administered to subjects. In general, formulations are administered that comprise between about $1\times10^4$ and about $1\times10^{10}$ CAR immunoresponsive cells. In most cases, the formulation will comprise between about $1\times10^5$ and about $1\times10^9$ CAR immunoresponsive cells, from about $5\times10^5$ to about $5\times10^8$ CAR immunoresponsive cells, or from about $1\times10^6$ to about $1\times10^7$ CAR immunoresponsive cells. However, the number of CAR immunoresponsive cells administered to a subject will vary between wide limits, depending upon the location, source, identity, extent and severity of the cancer, the age and condition of the individual to be treated etc. A physician will ultimately determine appropriate dosages to be used.

Tumor-targeting molecules are administered to a subject prior to, or concurrent with, or after administration of the CAR immunoresponsive cells. The tumor-targeting molecules bind to target cells in the subject by association to a tumor-associated antigen or a tumor-specific antigen. The tumor-targeting molecules may be formulated for administration to a subject using techniques known to the skilled artisan. Formulations of the tumor-targeting molecules may include pharmaceutically acceptable excipient(s). Examples of generally used excipients include, without limitation: saline, buffered saline, dextrose, water-for-injection, glycerol, ethanol, and combinations thereof, stabilizing agents, solubilizing agents and surfactants, buffers and preservatives, tonicity agents bulking agents, and lubricating agents.

The tumor-targeting molecules may be administered to a subject using modes and techniques known to the skilled artisan. Exemplary modes include, but are not limited to, intravenous, intraperitoneal, and intratumoral injection. Other modes include, without limitation, intradermal, subcutaneous (S.C., s.q., sub-Q, Hypo), intramuscular (i.m.), intra-arterial, intramedullary, intracardiac, intra-articular (joint), intrasynovial (joint fluid area), intracranial, intraspinal, and intrathecal (spinal fluids). In some cases, a CAR-T may be locally administered at a tumor lesion, such as a liver lesion. Any known device useful for parenteral injection or infusion of the formulations can be used to effect such administration.

Formulations comprising the tumor-targeting molecules are administered to a subject in an amount that is effective for treating and/or prophylaxis of the specific indication or disease. In general, formulations comprising at least about 0.1 mg/kg to about 100 mg/kg body weight of the tumor-targeting molecules are administered to a subject in need of treatment. In most cases, the dosage is from about 1 mg/kg to about 100 mg/kg body weight of the tagged proteins daily, taking into account the routes of administration, symptoms, etc. A physician will determine appropriate dosages to be used.

In one embodiment, a chimeric antigen receptor is used for stimulating an immunoresponsive cell-mediated immune response. For example, a T cell-mediated immune response is an immune response that involves the activation of T cells. Activated antigen-specific cytotoxic T cells are able to induce apoptosis in target cells displaying epitopes of foreign antigens on their surface, such as for example cancer cells displaying tumor antigens. In another embodiment, a chimeric antigen receptor is used to provide anti-tumor immunity in the mammal Due to a T cell-mediated immune response the subject will develop an anti-tumor immunity.

In certain cases, methods of treating a subject having cancer can involve administering to a subject in need of treatment one or more formulations of tumor-targeting molecules, wherein these molecules bind to a cancer cell, and administering one or more therapeutically-effective populations of subject CAR immunoresponsive cells, wherein the CAR immunoresponsive cells can bind the tumor-targeting molecules and induce cancer cell death. Another embodiment can relate to methods of treating a subject having cancer comprising administering to a subject in need of treatment one or more therapeutically-effective populations of subject anti-GPC3 CAR immunoresponsive cells, wherein the CAR immunoresponsive cells bind to a cancer cell, thereby inducing cancer cell death.

Administration frequencies of both formulations comprising anti-GPC3 CAR immunoresponsive cells and anti-GPC3 CAR immunoresponsive cells in combination with tumor-targeting molecules will vary depending on factors that include the disease being treated, the elements comprising the CAR immunoresponsive cells and the tumor-targeting molecules, and the modes of administration. Each formulation may be independently administered 4, 3, 2, or once daily, every other day, every third day, every fourth day, every fifth day, every sixth day, once weekly, every eight days, every nine days, every ten days, bi-weekly, monthly and bi-monthly.

A "chemotherapeutic agent" or "chemotherapeutic compound" and their grammatical equivalents as used herein, can be a chemical compound useful in the treatment of cancer. The chemotherapeutic cancer agents that can be used in combination with the disclosed CAR immunoresponsive cell include, but are not limited to, mitotic inhibitors (vinca alkaloids). These include vincristine, vinblastine, vindesine and Navelbine™ (vinorelbine, 5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein includes antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

Subject anti-GPC CAR immunoresponsive cells can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with subject anti-GPC3 CAR immunoresponsive cells include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; avastin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; CAR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen;

ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system; erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

In some cases, subject anti-GPC3 CAR immunoresponsive cell can be introduced by injection, catheter, or the like. In some cases, immunostimulatory agents can also be included, including, but not limited to, interleukins, e.g. IL-2, IL-3, IL-6, and IL-11, as well as the other interleukins, the colony stimulating factors, such as G-, M- and GM-CSF, interferons, e.g. .gamma.-interferon and erythropoietin. In some cases, a subject can be treated with a CAR-T, immunodepletant, and immunostimulant. A subject can be treated with IL-2 to boost performance of a CAR-T cellular product. In some cases, an immunostimulant can be a recombinant protein. An immunostimulant can also comprise an active portion of a protein. In some cases, an immunostimulant may only comprise a portion of a protein. A portion of a protein can be from about 50%, 60%, 70%, 80%, 90%, or up to about 100% of a protein.

Compositions comprising subject anti-GPC3 CAR immunoresponsive cells, such as CAR T cells, can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating genetically modified CAR immunoresponsive cells utilized in practicing the present invention in a required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. Various additives which may enhance stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the genetically modified CAR immunoresponsive cells or their progenitors.

In some cases, compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions. Viscosity of compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

In some cases, for example, in the compositions, formulations and methods of treating cancer, the unit dosage of the composition or formulation administered can be 5, 10, 15, 20, 25, 30, 35, 40, 45, 50, 55, 60, 65, 70, 75, 80, 85, 90, 95 or 100 mg. In some cases, the total amount of the composition or formulation administered can be 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 40, 50, 60, 70, 80, 90, or 100 g.

In some cases, a pharmaceutical composition comprising a subject anti-GPC3 CAR immunoresponsive cell, such as a CAR T cell, can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes.

For example, cells can be administered to a patient in conjunction with (e.g., before, simultaneously, or following) any number of relevant treatment modalities, including but not limited to treatment with agents such as antiviral therapy, cidofovir and interleukin-2, or Cytarabine (also known as ARA-C). In some cases, the engineered cells can be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. The engineered cell composition can also be administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, the engineered cell compositions can be administered following B-cell ablative therapy such as agents that react with CD20, e.g., Rituxan. For example, subjects can undergo standard treatment with high dose chemotherapy followed by peripheral blood stem cell transplantation. In certain embodiments, following the transplant, subjects can receive an infusion of the engineered cells, e.g., expanded engineered cells. Additionally, expanded engineered cells can be administered before or following surgery. The engineered cells obtained by any one of the methods described herein can be used for treating patients in need thereof against Host versus Graft (HvG) rejection and Graft versus Host Disease (GvHD). Therefore, a method of treating patients in need thereof against Host versus Graft (HvG) rejection and Graft versus Host Disease (GvHD) comprising treating said patient by administering to said patient an effective amount of engineered cells comprising inactivated TCR alpha and/or TCR beta genes can be contemplated.

Kits

Disclosed herein can be kits comprising compositions. Disclosed herein can also be kits for the treatment or prevention of a cancer, pathogen infection, immune disorder or allogeneic transplant. In one embodiment, a kit can include a therapeutic or prophylactic composition containing an effective amount of a cell comprising one or more anti-GPC3 CARs in unit dosage form. In some embodiments, a kit comprises a sterile container which may contain a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some cases, a subject anti-GPC3 CAR immunoresponsive cell, such as a CAR T cell, can be provided together with instructions for administering the CAR immunoresponsive cell to a subject having or at risk of developing a cancer, pathogen infection, immune disorder or allogeneic transplant. The instructions will generally include information about the use of the composition for the treatment or prevention of cancer, pathogen infection, immune disorder or allogeneic transplant. In some cases, a kit can include from about $1\times10^4$ cells to about $1\times10^{12}$ cells. In some cases a kit can include at least about $1\times10^5$ cells, at least about $1\times10^6$ cells, at least about $1\times10^7$ cells, at least about $4\times10^7$ cells, at least about $5\times10^7$ cells, at least about $6\times10^7$ cells, at least about $6\times10^7$ cells, at least about $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $6\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $6\times10^{11}$ cells, at least about $6\times10^{11}$ cells, at least about $8\times10^{11}$ cells, at least about $9\times10^{11}$ cells, or at least about $1\times10^{12}$ cells. For example, about $5\times10^{10}$ cells may be included in a kit. In another example, a kit may include $3\times10^6$ cells; the cells may be expanded to about $5\times10^{10}$ cells and administered to a subject.

In some cases, a kit may include allogenic cells. In some cases, a kit may include cells that may comprise a genomic modification. In some cases, a kit may comprise "off-the-shelf" cells. In some cases, a kit may include cells that may be expanded for clinical use. In some cases, a kit may contain contents for a research purpose.

In some cases, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. In some cases, instructions provide procedures for administering the anti-GPC3 CAR immunoresponsive cells, such as anti-GPC3 CAR T cells, after administering a chemotherapeutic agent. In some cases, instructions provide procedures for administering the anti-GPC3 CAR immunoresponsive cells before administering a chemotherapeutic agent. In some cases, instructions provide procedures for administering the anti-GPC3 CAR immunoresponsive cells concurrent with administering a chemotherapeutic agent. In some cases, instructions provide procedures for administering anti-GPC3 CAR immunoresponsive cells at least 12 hours after administering a chemotherapeutic agent. In some cases, instructions provide procedures for administering anti-GPC3 CAR immunoresponsive cells at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or up to 2 days, 3 days, 4 days, 5 days, 6 days, or 7 days after administering a chemotherapeutic agent. In some cases, instructions provide procedures for administering anti-GPC3 CAR immunoresponsive cells at least 24 hours after administering a chemotherapeutic agent. Anti-GPC3 CAR immunoresponsive cells can be formulated for intravenous injection. Anti-GPC3 CAR immunoresponsive cells can be formulated for intra-arterial injection to a subject's liver that can comprise a solid tumor.

In some cases, a kit may contain cyclophosphamide and/or fludarabine, formulated for administration to a subject in need thereof at about 60 mg/kg to about 80 mg/kg and at about 25 mg/m$^2$ to about 35 mg/m$^2$, respectively. In some cases a kit may contain products at a pediatric dosage.

Recombinant methods are well known in the art. The practice of the invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (Gait, ed., 1984); "Animal Cell Culture" (Freshney, ed., 1987); "Methods in Enzymology" (Academic Press, Inc.); "Handbook of Experimental Immunology" (Wei & Blackwell, eds.); "Gene Transfer Vectors for Mammalian Cells" (Miller & Calos, eds., 1987); "Current Protocols in Molecular Biology" (Ausubel et al., eds., 1987); "PCR: The Polymerase Chain Reaction", (Mullis et al., eds., 1994); and "Current Protocols in Immunology" (Coligan et al., eds., 1991). These techniques are applicable to the production of the polynucleotides and polypeptides, and, as such, can be considered in making and practicing the invention. Particularly useful techniques for are discussed in the sections that follow.

ADDITIONAL APPLICATIONS

Effective adoptive cell transfer-based immunotherapies (ACT) can be useful to treat cancer (e.g., metastatic cancer) patients. For example, autologous peripheral blood lymphocytes (PBL) can be modified using non-viral or viral methods disclosed herein to express an anti-GPC3 chimeric antigen receptor (CAR) that recognizes GPC3 on cancer or tumor cells and can be used in the disclosed methods and kits. The present invention can be directed to compositions and methods for immunotherapy, including but not limited to cancer, using a human or humanized chimeric antigen receptor following or concurrent with a lymphocyte reduction treatment to a subject. This chimeric antigen receptor makes use of human or humanized chimeric antigen receptor constructs following or concurrent with a lymphocyte reduction treatment to a subject.

These compositions and methods can provide a cancer therapy with many advantages. In some cases, a method can include modifying immunoresponsive cells to render the immunoresponsive cells substantially non-dependent upon the presence or activity of a major histocompatibility complex (MHC). In some cases, a polynucleic acid described herein can encode for a chimeric antigen receptor. Also disclosed are methods of making immunoresponsive cells expressing chimeric antigen receptors, such as anti-GPC3 CAR. Disclosed can also be a method of treatment in which patients with a cancer or disease can be administered anti-GPC3 CAR immunoresponsive cells.

Described herein is a method of treating a disease (e.g., cancer) in a recipient comprising transplanting to the recipient one or more subject anti-GPC3 CAR immunoresponsive cells following or concurrently with lymphocyte reduction treatment.

Autologous lymphocyte infusion can be used in a treatment. Autologous peripheral blood monocytes (PBMCs) can be collected from a patient in need of treatment and T cells can be activated and expanded using methods described herein and known in the art and then infused back into the patient. In other cases, allogenic cells can be used to treat a patient. Populations of subject CAR immunoresponsive cells may be formulated for administration; and wherein the administration to a subject using techniques known to the skilled artisan. Expanded cells can then be grown under conditions similar to those for unmodified cells, whereby the modified cells can be expanded and used for a variety of purposes.

The method disclosed herein can comprise transplanting. Transplantation can refer to adoptive transplantation of a cellular product. Transplanting can be autotransplanting, allotransplanting, xenotransplanting, or any other transplanting. For example, transplanting can be xenotransplanting. Transplanting can also be allotransplanting.

In some cases, about $5 \times 10^{10}$ subject anti-GPC3 CAR immunoresponsive cells are administered to a subject. In some embodiments, about $5 \times 10^{10}$ cells represents a median amount of cells administered to a subject. In some embodiments, about $5 \times 10^{10}$ cells are necessary to affect a therapeutic response in a subject. In some embodiments, at least about at least about $1 \times 10^7$ cells, at least about $2 \times 10^7$ cells, at least about $3 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^{11}$ cells, at least about $3 \times 10^{11}$ cells, at least about $4 \times 10^{11}$ cells, at least about $5 \times 10^{11}$ cells, at least about $6 \times 10^{11}$ cells, at least about $6 \times 10^{11}$ cells, at least about $8 \times 10^{11}$ cells, at least about $9 \times 10^{11}$ cells, or at least about $1 \times 10^{12}$ cells. For example, about $5 \times 10^{10}$ cells may be administered to a subject. In another example, starting with $3 \times 10^6$ cells, the cells may be expanded to about $5 \times 10^{10}$ cells and administered to a subject. In some cases, cells are expanded to sufficient numbers for therapy. For example, $5 \times 10^7$ cells can undergo rapid expansion to generate sufficient numbers for therapeutic use. In some cases, sufficient numbers for therapeutic use can be $5 \times 10^{10}$. Any number of cells can be infused for therapeutic use. For example, a subject may be infused with a number of cells between $1 \times 10^6$ to $5 \times 10^{12}$ inclusive. A patient may be infused with as many cells that can be generated for them. In some cases, cells that are infused into a patient are not all engineered. For example, at least 90% of cells that are infused into a patient can be engineered. In other instances, at least 40% of cells that are infused into a patient can be engineered. In some embodiments, a method can comprise calculating and/or administering to a subject an amount of engineered cells necessary to affect a therapeutic response in the subject. In some embodiments, calculating the amount of engineered cells necessary to affect a therapeutic response comprises the viability of the cells and/or the efficiency with which an anti-GPC3 CAR transgene has been integrated into the genome of a cell. In some embodiments, in order to affect a therapeutic response in a subject, the cells administered to the subject may be viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells are viable cells. In some embodiments, in order to affect a therapeutic response in a subject, the cells administered to a subject may be cells that have had one or more transgenes successfully integrated into the genome of the cell. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells have had one or more CAR transgenes successfully integrated into a genome of a cell.

In some cases, a subject can be administered subject anti-GPC3 CAR immunoresponsive cells, wherein CAR immunoresponsive cells that can be administered may be about 1 to about 35 days old. For example, administered cells may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or up to about 40 days old. An age of a CAR immunoresponsive cell can be considered from a time of stimulation. An age of a CAR immunoresponsive cell can be considered from a time of apheresis. An age of a CAR immunoresponsive cell can be considered from a time of transduction. In some embodiments, CAR immunoresponsive cell that can be administered to a subject are about 10 to about 14 or about 20 days old. In some cases, an "age" of a CAR immunoresponsive cell can be determined by a length of a telomere. For example, a "young" CAR immunoresponsive cell can have a longer telomere length than an "exhausted" or "old" CAR immunoresponsive cell. Without being bound to a particular theory, it can be believed that immunoresponsive cells lose an estimated telomere length of about 0.8 kb per week in culture, and that young CAR immunoresponsive cell cultures can have telomeres that are about 1.4 kb longer than immunoresponsive cells that are about 44 days old. Without being bound to a particular theory, it is believed that longer telomere lengths can be associated with positive objective clinical responses in patients and persistence of the cells in vivo.

In some cases, cells are isolated from the subject organism, transfected with a nucleic acid (e.g., gene or cDNA), and re-infused back into the subject organism (e.g., patient).

Cells (e.g., engineered cells or engineered primary T cells) before, after, and/or during transplantation can be functional. For example, transplanted cells can be functional for at least or at least about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 40, 50, 60, 70, 80, 90, or 100 days after transplantation. Transplanted cells can be functional for at least or at least about 1, 2, 3, 4, 5, 6, 7, 8, 9, 10, 11, or 12 months after transplantation. Transplanted cells can be functional for at least or at least about 1, 2, 3, 4, 5, 6, 7, 8, 9, 10, 15, 20, 25, or 30 years after transplantation. In some cases, transplanted cells can be functional for up to the lifetime of a recipient.

Further, transplanted cells can function at 100% of their normal intended function. Transplanted cells can also function 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or up to about 100% of their normal intended function.

Transplanted cells can also function over 100% of their normal intended function. For example, transplanted cells can function 110, 120, 130, 140, 150, 160, 170, 180, 190, 200, 250, 300, 400, 500, 600, 700, 800, 900, 1000, or up to about 5000% of their normal intended function.

Transplanting can be by any type of transplanting. Sites can include, but not limited to, liver subcapsular space, splenic subcapsular space, renal subcapsular space, omentum, gastric or intestinal submucosa, vascular segment of small intestine, venous sac, testis, brain, spleen, or cornea. For example, transplanting can be subcapsular transplanting. Transplanting can also be intramuscular transplanting. Transplanting can be intraportal transplanting.

After treatment (e.g., any of the treatment as disclosed herein), transplant rejection can be improved as compared to when one or more wild-type cells is transplanted into a recipient. For example, transplant rejection can be hyperacute rejection. Transplant rejection can also be acute rejection. Other types of rejection can include chronic rejection. Transplant rejection can also be cell-mediated rejection or T cell-mediated rejection. Transplant rejection can also be natural killer cell-mediated rejection.

Improving transplantation can mean lessening hyperacute rejection, which can encompass a decrease, lessening, or diminishing of an undesirable effect or symptom. Transplantation can refer to adoptive transplantation of a cellular product.

Another indication of successful transplantation can be the days a recipient does not require immunosuppressive therapy. For example, after treatment (e.g., transplantation) provided herein, a recipient can require no immunosuppressive therapy for at least or at least about 1, 2, 3, 4, 5, 6, 7, 8, 9, 10 or more days. This can indicate that transplantation was successful. This can also indicate that there is no rejection of the transplanted cells, tissues, and/or organs.

In some cases, a recipient can require no immunosuppressive therapy for at least 1 day. A recipient can also require no immunosuppressive therapy for at least 7 days. A recipient can require no immunosuppressive therapy for at least 14 days. A recipient can require no immunosuppressive therapy for at least 21 days. A recipient can require no immunosuppressive therapy for at least 28 days. A recipient can require no immunosuppressive therapy for at least 60 days. Furthermore, a recipient can require no immunosuppressive therapy for at least 1, 2, 3, 4, 5, 6, 7, 8, 9, 10, or more years.

Another indication of successful transplantation can be the days a recipient requires reduced immunosuppressive therapy. For example, after the said treatment provided herein, a recipient can require reduced immunosuppressive therapy for at least 1, 2, 3, 4, 5, 6, 7, 8, 9, 10 or more days. This can indicate that transplantation was successful. This can also indicate that there is no or minimal rejection of the transplanted cells, tissues, and/or organs.

For example, a recipient can require reduced immunosuppressive therapy for at least 1 day. A recipient can also require reduced immunosuppressive therapy for at least 7 days. A recipient can require reduced immunosuppressive therapy for at least 14 days. A recipient can require reduced immunosuppressive therapy for at least 21 days. A recipient can require reduced immunosuppressive therapy for at least 28 days. A recipient can require reduced immunosuppressive therapy for at least 60 days. Furthermore, a recipient can require reduced immunosuppressive therapy for at least 1, 2, 3, 4, 5, 6, 7, 8, 9, 10 or more years.

Reduced immunosuppressive therapy can refer to less immunosuppressive therapy compared to a required immunosuppressive therapy when one or more wild-type cells is transplanted into a recipient.

Immunosuppressive therapy can comprise any treatment that suppresses the immune system. Immunosuppressive therapy can help to alleviate, minimize, or eliminate transplant rejection in a recipient. For example, immunosuppressive therapy can comprise immuno-suppressive drugs. Immunosuppressive drugs that can be used before, during and/or after transplant, but are not limited to, MMF (mycophenolate mofetil (Cellcept)), ATG (anti-thymocyte globulin), anti-CD154 (CD40L), anti-CD40 (2C10, ASKP1240, CCFZ533X2201), alemtuzumab (Campath), anti-CD20 (rituximab), anti-IL-6R antibody (tocilizumab, Actemra), anti-IL-6 antibody (sarilumab, olokizumab), CTLA4-Ig (Abatacept/Orencia), belatacept (LEA29Y), sirolimus (Rapimune), everolimus, tacrolimus (Prograf), daclizumab (Ze-napax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, leflunomide, anti-IL-2R-Ab, rapamycin, anti-CXCR3 antibody, anti-ICOS antibody, anti-OX40 antibody, and anti-CD122 antibody. Furthermore, one or more than one immunosuppressive agents/drugs can be used together or sequentially. One or more than one immunosuppressive agents/drugs can be used for induction therapy or for maintenance therapy. The same or different drugs can be used during induction and maintenance stages. In some cases, daclizumab (Zenapax) can be used for induction therapy and tacrolimus (Prograf) and sirolimus (Rapimune) can be used for maintenance therapy. Daclizumab (Zenapax) can also be used for induction therapy and low dose tacrolimus (Prograf) and low dose sirolimus (Rapimune) can be used for maintenance therapy Immunosuppression can also be achieved using non-drug regimens including, but not limited to, whole body irradiation, thymic irradiation, and full and/or partial splenectomy. These techniques can also be used in combination with one or more immuno-suppressive drugs.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Construction of Anti-GPC3-CAR Vector

An exemplary lentiviral plasmid vector was constructed using a third-generation of self-inactivating lentiviral vector system. The system contains packaging plasmid pMDLg RRE encoding Gag/Pol (Addgene), packaging plasmid pRSV-REV encoding Rev (Addgene), envelope plasmid pCMV-VSV-G encoding VSV-G (Addgene), and a recombinant expression vector encoding a CAR gene based in an empty vector pRRLSIN-cPPT.PGK-GFP.WPRE (Addgene). The system can effectively lower the risk of forming replication capable lentivirus (RCL) particles.

The empty vector pRRLSIN-cPPT.PGK-GFP.WPRE contains a promoter of elongation factor-1 α (EF-1α), and insert MluI cleavage site between the promoter and CD8αsp signal peptide. Specifically, the pWPT-EGFP vector (Addgene) was double digested with ClaI/SalI (NEB) to recover DNA fragments of 1.1 Kb, which were then ligated with T4 DNA ligase to pRRLSIN-cPPT.PGK-GFP.WPRE which was double digested with ClaI/SalI. The ligation mixture was then transformed into host cell TOP10. Positive clones were identified by colony PCR and confirmed by sequencing, giving rise to recombinant plasmid pRRLSIN-cPPT.EF-1α-EGFP.WPRE. EF-1α promoter (SEQ ID NO: 33, including Mlu I cleavage site) of the CD8a signal domain (aka Fragment 1, 442 bp) was amplified with upstream primer 5'-gcaggggaaagaatagtagaca-3' (SEQ ID NO: 31), downstream primer 5'-CGGCCTGGCGGCGTGGAG-3' (SEQ ID NO: 32), and pRRLSIN-cPPT.EF-1α-EGFP.WPRE as template, and the amplification was conducted under the following conditions: initial denaturation at 94° C. for 4 min; denaturation at 94° C. for 30 s, annealing at 53° C. for 30 s, and extension at 68° C. for 30 s; and after 25 cycles, extension at 68° C. for 10 min. The amplified band was confirmed by agarose gel electrophoresis to have the expected fragment size.

Humanized antibody 35 has been described in Chinese Patent Application Publication No. CN106397593A, which is capable of specifically recognizing humanized GPC3 protein. To construct 35-CAR lentiviral plasmid, the following were used in amplification to provide heavy chain variable domain fragment: fragment containing heavy chain variable domain 35 (SEQ ID NO: CN106397593A) as template, upstream primer 5'-ctccacgccgccaggccg-gaggtgcagctggtgcag-3" (SEQ ID NO: 34), and downstream primer 5'-GCGGTGTCCTCGCTCCGCAGGCTGCTC AGCTCC ATGTAGGCGGTG-3' (SEQ ID NO: 35); the following were used to provide light chain variable domain fragment: fragment containing light chain variable domain of 35 (SEQ ID NO: 79 CN106397593A as template, upstream primer 5'-GCGGAGCGAGGAC ACCGCCGT GT ACT ACT GCGCCGGTTCT AC AGCT AC-3' (SEQ ID NO: 36), and downstream primer 5'-CGGCGCTGGCGTCGTGGTACGTTT-GATCTCCAGCTTGGTG-3' (SEQ ID NO: 37). The heavy chain and light chain variable domain primers were amplified with bridging PCR to provide 35 scFv fragment (SEQ ID NO: 38, aka Fragment 2, 765 bp), which comprises a sequence repetitive to the upstream CD8a signal peptide and the downstream hinge region. PCR amplification was conducted under the following conditions: initial denaturation at 94° C. for 4 min; denaturation at 94° C. for 40s, annealing at 58° C. for 40s; extension at 68° C. for 40s; and after 25 cycles, an extension at 68° C. for 10 min. The amplified band was confirmed by agarose gel electrophoresis to have the expected fragment size.

The upstream primer 5'-accacgacgccagcgccg-3' (SEQ ID NO: 39) and downstream primer 5'-aatccagaggttgat-tgtcgacctagcgagggggcagggcctgc-3' (SEQ ID NO: 40) were used, with pWPT-eGFP-F2A-GPC3-28Z as a template (See Chinese Patent Application CN 104140974 A), to amplify Hinge-28Z (SEQ ID NO: 41, Fragment 3, 703 bp) (with internal Sal I cleavage site). PCR amplification was conducted under the following conditions: initial denaturation at 94° C. for 4 min; denaturation at 94° C. for 30 s; annealing at 60° C. for 30 s; extension at 68° C. for 30 s; and after 25 cycles, final extension at 68° C. for 10 min. The amplified band was confirmed by agarose gel electrophoresis to have the expected fragment size. An equimolar amount (about 50 ng) of Fragment 1, Fragment 2 and Fragment 3 were amplified by overlap PCR under the following conditions: initial denaturation at 94° C. for 4 min; denaturation at 94° C. for 40 s; annealing at 60° C. for 40 s; extension at 68° C. for 140 s; and after 5 cycles, final extension at 68° C. for 10 min. DNA polymerase, upstream primer 5'-gcaggg-gaaagaatagtagaca-3' (SEQ ID NO: 31) and downstream primer 5'-aatccagaggttgattgtcgacctagcgagggggcagggcctgc-3' (SEQ ID NO: 40) were then supplemented to the mixture, and amplified for 25 cycles under the following conditions: initial denaturation at 94° C. for 4 min; denaturation at 94° C. for 40 s; annealing at 60° C. for 40 s; extension at 68° C. for 140 s; and final extension at 68° C. for 10 min. The theoretical size of the resulting 35-28Z (SEQ ID NO: 41) was 1874 bp. The amplified product was confirmed by agarose gel electrophoresis and had the expected fragment size, and sequence as shown as SEQ ID NO: 23.

The vector pRRLSIN-cPPT.EF-1α-EGFP.WPRE vector and 35-28Z were digested with MluI and SalI, and then ligated with T4 ligase, and transformed into TOP10. Positive clones were identified with colony PCR and sequenced by Invitrogen to confirm that pRRL-EF-1α-35-28Z was obtained.

Example 2: Packaging of Anti-GPC3-CAR Lentivirus

Anti-GPC3-CAR lentivirus stock solution (0.75 L) was prepared using Embryonic Kidney Cells 293 T (ATCC: CRL-11268). Specifically, 293T cells were seeded at $1.17 \times 10^4/cm^2$ onto a 5-layer cellstack (Corning). Solution A was prepared at the day of transfection to comprise 133.2 μg of packaging plasmid pRSV-Rev, 133.2 μg of pMDLg/pRRE, 51.56 μg of pCMV-VSV-G and 111.7 μg of pRRL-EF-1α-35-28Z, by dissolving 966 μg of all the plasmid into 17 ml DMEM basal medium and gently mixing it. Solution B was prepared by dissolving 2.9 mg PEI (Polysciences) into 17 ml DMEM basal medium, and the solution was gently mixed and incubated at room temperature for 5 min. Solution A was then introduced into Solution B, homogenously mixed, and allowed to stand still at room temperature for 20 min to 25 min. The 293 T culture solution was then transferred from a Cellstack into a 1 L flask. The combined solution comprising plasmid and PEI was then introduced into the culture solution and mixed gently. The resulting solution was then transferred into a Cellstack, and incubated for 5 h at 37° C., 5% $CO_2$ before the medium was changed to fresh growth medium DMEM supplemented with 10% FBS (Life Technology). The culture was then incubated at 37° C., 5% $CO_2$ for 48 h. The lentiviral stock solution was then recovered, filtered with a 0.45 μm (Millipore) filter, concentrated and purified with KrosFlo® Iii Tangential Flow Filtration System (Spectrum), and washed with AIM-V(Life technology) and stored. Titration of virus was conducted according to the method described in CN104140974A. Virus titer was calculated to be about $1 \times 10^8$/ml. The virus was packaged at $1 \times 10^8$/vial, and stored at −80° C. for later use.

Example 3: Preparation of Anti-GPC3-CAR T Cells and In Vitro Anti-Tumor Assay Against Liver Cancer Cells CAR T cells were prepared in an immune cell preparatory lab following cGMP standards. Specifically, peripheral blood of subjects or white blood cell enriched blood obtained using a COBE Spectra blood component separator were separated by density gradient centrifugation to obtain human peripheral blood mononuclear cells (PBMC).

PBMCs were mixed with magnetic beads coated with both anti-CD3 and anti-CD28 antibodies (Life technology) at a ratio of PMBC to magnetic beads of 1:3, stimulated with recombinant human IL-2 at a final concentration of 300 U/mL (Shanghai Hua Xin High Biotechnology Co., Ltd.) and cultivated for 48 h. Subsequently, the aforementioned lentivirus was used to transduce the activated T cells at MOI of approximately 5, with efficiency of transduction enhanced by RetroNectin (Takara). 24 h and 48 h following transduction, free viruses were removed by medium change through low-speed centrifugation (100 g×10 min). 72 h following transduction, the magnetic beads were removed. The aforementioned centrifugation was repeated, and a sub-culture was obtained at a density of $5\times10^5$/mL. Subsequently, the cells were sub-cultured every other day at a density of about $3\times10^5$/mL while recombinant human IL-2 was added into the lymphocyte culture medium at a final concentration of 300 U/mL.

The transduced CAR T cells were assayed for their expression of CAR by flow cytometry following in vitro cultivation for 10 to 12 days. That is, positive transduction rates of the CAR T cells were assayed and are shown in Table 7. Moreover, an in vitro anti-tumor assay was conducted by co-incubation with high GPC3 expressing liver cancer cells Huh-7, low GPC3 expressing PLC/PRF/5, and GPC3 negative SK-HEP-1 for 18 h at an effector to target ratio of 3:1, 1:1, and 1:3. For a detailed procedure, refer to CN104140974A. In vitro anti-tumor activity results at the effector to target ratio of 1:1 are presented in Table 8.

Results show that anti-GPC3-CAR T cells expressed a CAR ranging from about 40% to about 80%. Furthermore, the anti-GPC3-CAR T cells had specific killing of GPC3 positive Huh-3 and PLC/PRF/5 with a dose dependent effect on the effector-to-target ratio, whereas they did not have killing effect on GPC3 negative SK-HEP-1 (Table 8), indicating that anti-GPC3-CAR T cells prepared from the subjects in the present disclosure have excellent targeted killing effects.

TABLE 7

Summary of positive transduction rate of anti-GPC3-CAR T cells from the subjects and administration regimen

| Queue No. | Subject No. | CART-positive rate (%) | Times of administration | Total administered cell number of CAR T cells from the subject ($10^9$) |
|---|---|---|---|---|
| Queue 1 | H01[1] | 79 | 6 | 4.5 |
| | H01[2] | 74 | 1 | 1.2 |
| | H02 | 51.1 | 7 | 10.2 |
| | H03 | 41.4 | 3 | 0.9 |
| Queue 2 | H04 | 60.6 | 1 | 10.6 |

TABLE 8 in vitro killing of anti-GPC3-CAR T cells from subjects (effector to target ratio of 3:1, 1:1, and 1:3, in vitro for 18 h)

| | In vitro killing (%) | | | | | | | | |
|---|---|---|---|---|---|---|---|---|---|
| | Huh-7 at different effector to target ratio | | | PLC/PRF/5 at different effector to target ratio | | | SK-HEP-1 at different effector to target ratio | | |
| | 3:1 | 1:1 | 1:3 | 3:1 | 1:1 | 1:3 | 3:1 | 1:1 | 1:3 |
| H01[1/2] | 82.3 ± 10.3 | 87.5 ± 6.8 | 52.8 ± 1.8 | 48.4 ± 9.6 | 28.7 ± 4.8 | 13.1 ± 1.3 | (—)3.4 ± 1.38 | 4.0 ± 2.2 | 3.8 ± 1.4 |
| H02 | 96.1 ± 1.32 | 62.2 ± 6.1 | 9.5 ± 2.3 | 53.2 ± 8.2 | 42 ± 11.5 | (—)4.4 ± 4.1 | 1.4 ± 1.3 | 9.9 ± 2.1 | 0.4 ± 0.7 |
| H03 | 131.1 ± 9.3 | 81.1 ± 14.3 | 53.4 ± 5.9 | 64.5 ± 18.7 | 14.5 ± 4.6 | 8.1 ± 2.3 | 5.2 ± 1.6 | 2.4 ± 2.4 | 6.4 ± 0.6 |
| H04 | 136 ± 6.0 | 65 ± 6.0 | 22.2 ± 3.5 | 94.3 ± 1.5 | 72 ± 0.5 | 47 ± 2.9 | 26.5 ± 1.7 | 15.4 ± 0.8 | 9.2 ± 1.1 |

Example 4: Change of Lymphocytes after Lymphocyte Reduction

After confirmation that no abnormality occurred during anti-GPC3-CAR T cell preparation from treated subjects, the subjects were subjected to a comprehensive assessment of various physical conditions to determine whether the subjects were suitable for in vivo lymphocyte reduction. A primary lymphocyte reduction protocol was designed for administration to suitable subjects.

The following two lymphocyte reduction protocols were designed: Protocol 1: cyclophosphamide (CTX) single agent lymphocyte reduction protocol, at a dose of 1 g/m²/day×1 day. Protocol 2: combined fludarabine (FLU)+cyclophosphamide lymphocyte reduction protocol, at a dose of 20~30 mg fludarabine/m²/day×4 days+500 mg cyclophosphamide/m²/day×2 days.

The protocol was implemented with adjustment to include the following conditions: calculation of human surface area was conducted according to Stevenson's formula (Chinese Journal of Physiology, 12:327, 1937). That is, surface area (m²)=0.0061×height (cm)+0.0128×weight (kg)−0.1529. For example, an adult having a height of 170 cm and a weight of 60 kg has a surface area of 1.6521 m². Subjects not suitable for lymphocyte reduction due to existing physical conditions or on their own volition were assigned to a second queue. Different lymphocyte reduction treatments were performed on a total of three subjects (H01, H02, and H03). One subject (H04) was not subjected to ablation due to physical conditions and their volition. Protocols are presented in Table 9.

TABLE 9

Summary of lymphocyte reduction protocols for subjects

| Queue No. | Subject No. | Lymphocyte Reduction Protocol | | Time Window |
|---|---|---|---|---|
| | | CTX | FLU | |
| Queue 1 | H01[1] | 1 g/m²/d * 2 d | / | D-5~D-4 |
| | H01[2] | 500 mg/m²/d * 2 d | 25 mg/m²/d * 20 d | D37~D38 |
| | H02 | 1 g/m²/d * 2 d | / | D-2 |
| | H03 | 500 mg/m²/d * 2 d | 50 mg/m²/d * 4 d | D-6~D-2 |
| Queue 2 | H04 | | / | |

Figure 2:
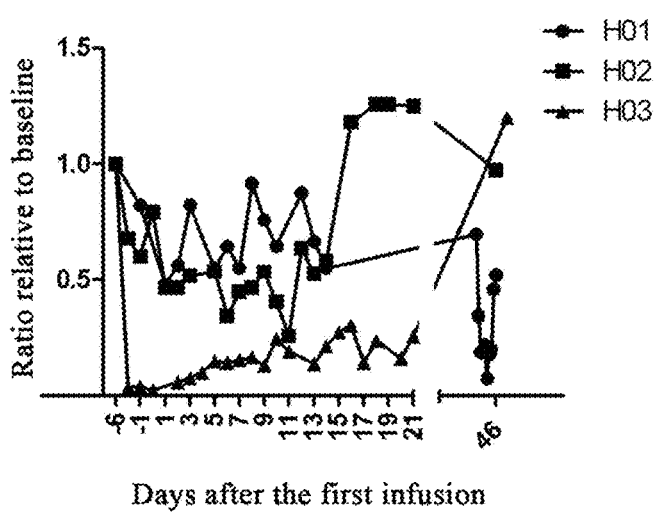
FIG. 2 shows the ratio-to-baseline level of lymphocytes of individuals H01, H02, or H03 treated with cyclophosphamide and/or fludarabine.

H01¹ indicates an initial administration of anti-GPC3-CAR T cell therapy to subject H01; H01² indicates a second administration of anti-GPC3-CAR T cell therapy to subject H01; and D0 was defined as the day when anti-GPC3-CAR T cell administration was conducted. Following implementation of the aforementioned lymphocyte reduction protocols, various changes occurred in the absolute values of lymphocytes in the subjects. As a result of the lymphocyte reduction treatment of cyclophosphamide as a single agent, lymphocytes decreased by about 40% to about 72%. The combination of fludarabine and cyclophosphamide lymphocyte reduction yielded a more significant difference in lymphocyte reduction, at about 82% to about 96.5%, as compared to the cyclophosphamide single agent administration. Specifically, FIG. 2 demonstrates the change of the ratio of the absolute number of lymphocytes to the baseline at each monitored time point before and after lymphocyte reduction treatment administration. The aforementioned results demonstrate that the combination of fludarabine and cyclophosphamide results in superior lymphocyte reduction as compared to the cyclophosphamide single agent reduction protocol.

Example 5: Clinical Response of Subjects Following Ablation

About 2 days after the implementation of lymphocyte reduction, subjects were administered anti-GPC3-CAR T cell treatment by intravenous administration. The doses of the administered anti-GPC3-CAR T cells are presented in Table 7. The clinical responses of the subjects following the treatment are summarized in Table 10. The results demonstrate that the three subjects that underwent lymphocyte reduction have stable disease (SD) or partial disease (PR) following the anti-GPC3-CAR T cell treatment up to now. In contrast, the subject H04, that did not receive the lymphocyte reduction treatment, shows progressive disease by MRI 4 weeks following the anti-GPC3-CAR T cell treatment.

Figure 3:
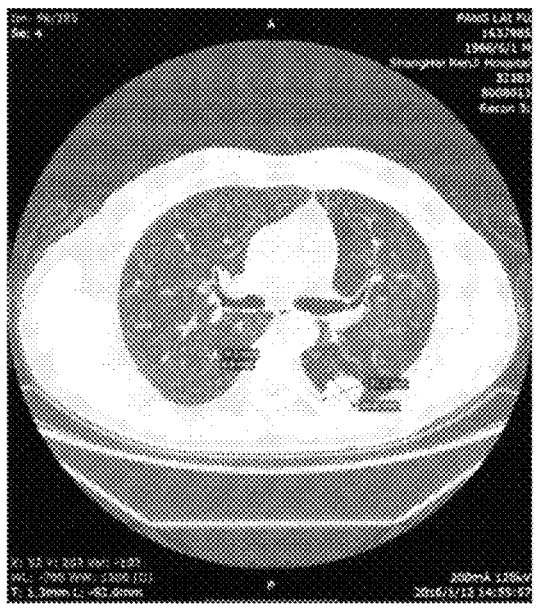
FIG. 3 shows a pre- and post-treatment magnetic resonance imaging (MRI) scan of a liver section.
Figure 3:
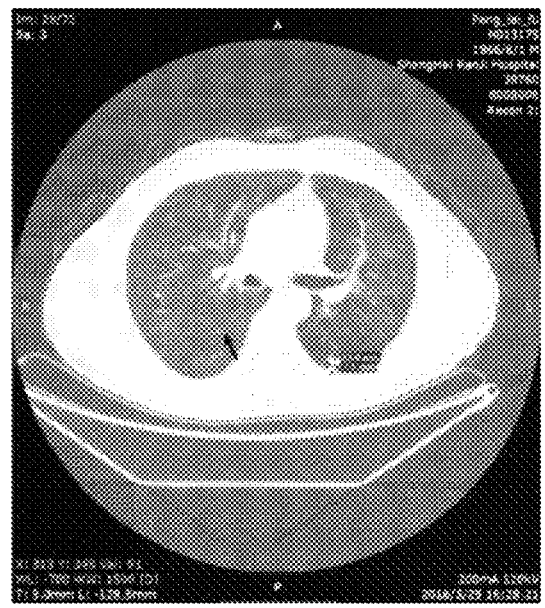

As to AFP results, the subject H02 could not be assessed for prognosis from the tumor marker due to AFP insensitivity. For two other subjects, their AFP levels somewhat decreased, as in Table 10. It should be noted that the subject H03, after lymphocyte reduction using combined fludarabine and cyclophosphamide, showed an 87% reduction of AFP as compared to the baseline before the treatment. Meanwhile, imaging shows that the target site has partial clinical response. FIG. 3 shows MRI results from subject H03 before treatment vs. 10 weeks post-treatment.

TABLE 10

Summary of clinical response of subjects following anti-GPC3-CAR T cell treatment

| Queue No. | Subject No. | AFP change | Efficacy as assessed by imaging | Time window for assessment |
|---|---|---|---|---|
| 1 | H01[1] | 18.8%↓ | SD | 3 days following first course of treatment |
| | H01[2] | 46.5%↓ | SD | 6 days following first course of treatment |
| | H02 | / | SD | 8 weeks post-treatment |
| | H03 | 87%↓ | PR | 10 weeks post-treatment |
| 2 | H04 | / | PD | 4 weeks post-treatment |

Note: ↓ indicates decreased AFP level; ↑ indicates increased AFP level; PD indicates progressive disease; CR indicates complete response; and PR indicates partial response. Safety data and clinical observation showed that following treatment with anti-GPC3-CAR T cells, no subjects develop intolerable toxic or side effect. All subjects had some extent of fever and GRP increase. Subjects H01 and H04 had a shiver following administration. Subject H03 had decreased albumin caused by fever. By taking exogenous nutrient and albumin, the subject had normal albumin after the fever was gone (Table 11).

TABLE 11

Summary of toxic or side effect on subjects after administration of anti-GPC3-CAR T cells following lymphocyte reduction therapy.

| Queue No. | Subject No. | Toxic or Side Effect |
|---|---|---|
| Queue 1 | H01[1] | Fever (<=38.9° C.); CRP (<=27.2 mg/L) |
| | H01[2] | Fever (<=39.3° C.); CRP (<=120 mg/L); Shiver |
| | H02 | Fever (<=39.3° C.); CRP (<=60 mg/L) |
| | H03 | Fever (<=39.3° C.); CRP (<=79.9 mg/L); Albumin (20-46.5 g/L) |
| Queue 2 | H04 | Fever (<=39.9° C.); CRP (<=55.9 mg/L); Shiver |

Moreover, cytokine release syndrome, which often occurs during treatment of blood cancers using CAR T cells, was not observed in this clinical study, indicating that anti-GPC3-CAR T cells are safe.

In sum, the results of the clinical studies using CAR-GPC T cells to treat GPC3 positive hepatocellular cancer demonstrate that subjects with effective lymphocyte reduction were conferred with certain clinical benefits by anti-GPC3-CAR T cell treatment, whereas the subjects without lymphocyte reduction therapy were not conferred any clinical benefit. Further, neither of the subjects with and without lymphocyte reduction exhibited intolerable toxic or side effect, with both of them having certain adverse responses such as fever and increased CRP, indicating that the lymphocyte reduction might not have worsened the adverse response of the subjects. Further, as regards to the effect of lymphocyte reduction therapy and benefit to the subjects, the combined fludarabine and cyclophosphamide lymphocyte reduction protocol may be superior to the cyclophosphamide single agent lymphocyte reduction protocol. In sum, anti-GPC3-CAR T cell treatment following implementation of effective lymphocyte reduction may provide an effective therapeutic solution to clinical treatment of GPC3 positive hepatocellular carcinoma.

Example 6: Phenotypic Analysis

Expression of cell surface molecules is determined by flow cytometry using standard methodology. The following monoclonal antibodies conjugated with phycoerythrin, fluorescein isothiocyanate, and/or peridinin chlorophyll protein are used: CD3, CD4, CD8, CD30, CCR4, CD45RA, CD45RO, CCR7, CD62L, CD56, αβT-cell receptor (BD Biosciences PharMingen). Expression of CAR by T cells is detected using an anti-CAR antibody. Samples are analyzed using a FACSCalibur (BD Biosciences PharMingen), and data is analyzed by CellQuest Pro software (BD Biosciences, San Jose, Calif.). At least 10,000 positive events are measured for each sample.

Example 7: Cytotoxicity Assay: Liver Cancer

Figure 4A:
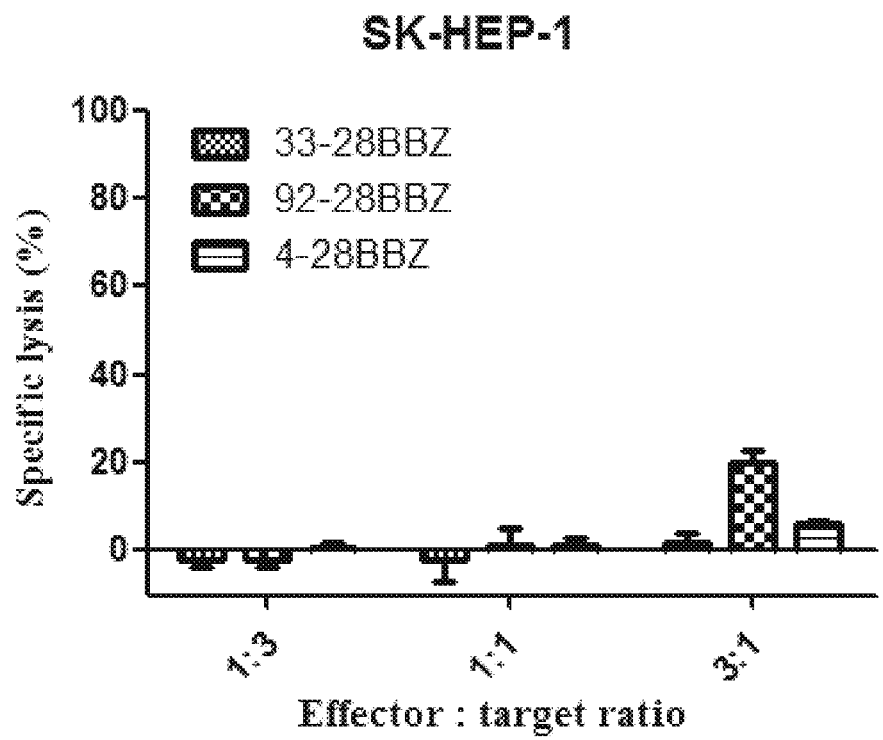
FIG. 4A shows a CytoTox 96® Non-Radioactive Cytotoxicity Assay performed on 33-28BBZ, 92-28BBZ, and 4-28BBZ co-cultured with control cells, SK-HEP-1
Figure 4B:
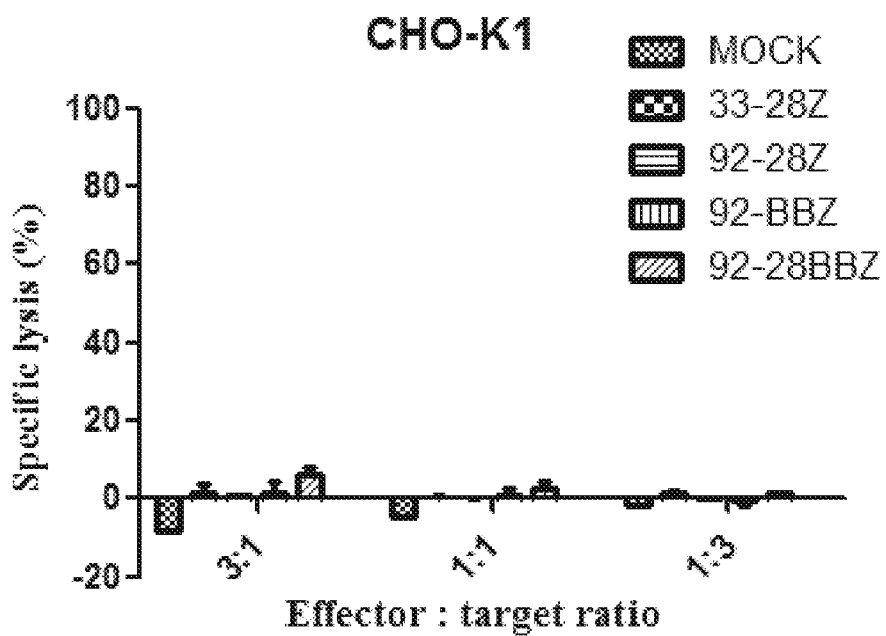
FIG. 4B shows a CytoTox 96® Non-Radioactive Cytotoxicity Assay performed on 33-28Z, 92-28Z, 92-BBZ, and 92-28BBZ co-cultured with a second control cell line, CHO-K1, at effector: target ratio of 3:1, 1:1, or 1:3.

To evaluate the potential cytotoxic effect of the second generation or third generation CAR-T transduced T cells, a CytoTox 96® Non-Radioactive Cytotoxicity Assay (Promega) was performed. Briefly, anti-GPC3 CAR-T cells, 33-28BBZ, 92-28BBZ, and 4-28BBZ, were co-cultured with control cells, SK-HEP-1 (FIG. 4A) and CHO-K1 (FIG. 4B), at effector: target ratio of 3:1, 1:1, or 1:3 with target cells at 10,000/well, and incubated for 18 hours at 37° C. Visible wavelength absorbance data was collected using a standard 96-well plate reader post incubation.

Figure 5A:
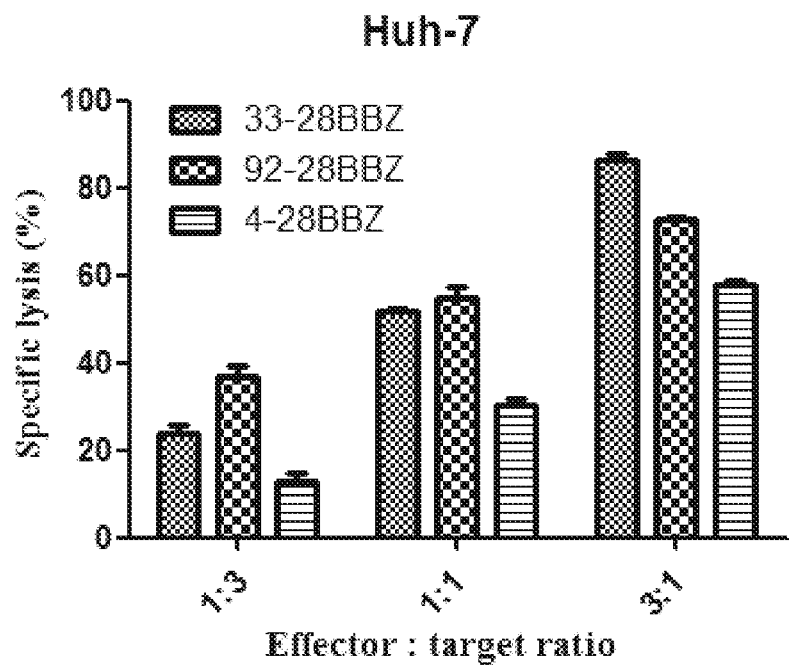
FIG. 5A shows a CytoTox 96® Non-Radioactive Cytotoxicity Assay performed on 33-28BBZ, 92-28BBZ, and 4-28BBZ co-cultured with GPC3-positive liver cancer cells, Huh-7, or control cells as shown in FIG. 5B transduced to express GPC3, CHO-K1-GPC3+, at effector: target ratio of 3:1, 1:1, or 1:3.
Figure 5B:
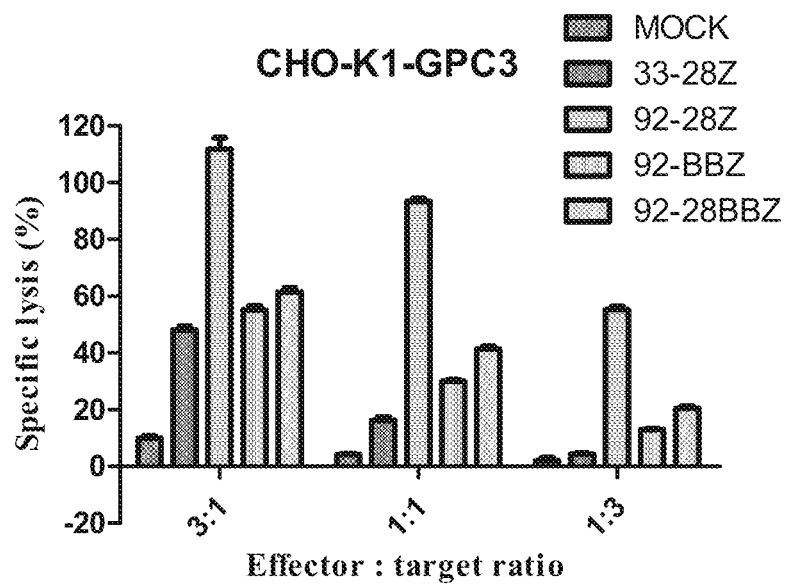

To evaluate anti-tumor cytotoxicity CAR-T cells, 33-28BBZ, 92-28BBZ, and 4-28BBZ, were co-cultured with GPC3-positive liver cancer cells, Huh-7, or control cells transduced to express GPC3, CHO-K1-GPC3+, at effector: target ratio of 3:1, 1:1, or 1:3 with target cells at 10,000/well, and incubated for 18 hours at 37° C., FIG. 5A and FIG. 5B respectively. Visible wavelength absorbance data was collected using a standard 96-well plate reader post incubation.

For all effector: target ratios, the cytotoxicity was obtained as the average value of 5 repetitive wells.
Results Cytotoxicity data show that 33-28BBZ, 92-28BBZ, and 4-28BBZ CAR-T constructs had cytotoxicity against tumor cell lines expressing GPC3 while having no cytotoxicity to non-GPC3 expressing control lines at 3:1, 1:1, and 1:3.

Example 8: Cytotoxicity Assay: Liver Cancer Panel

Figure 6A:
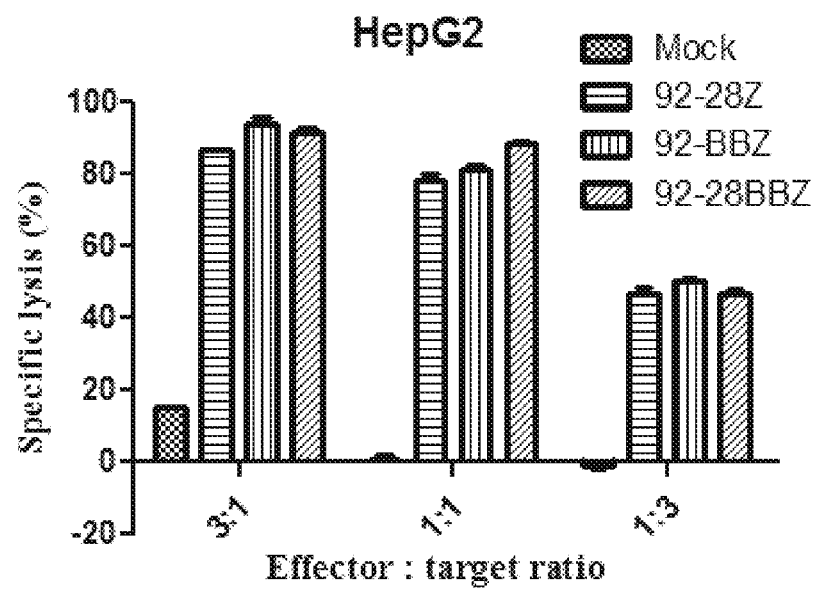
FIG. 6A shows a CytoTox 96® Non-Radioactive Cytotoxicity Assay performed on anti-GPC3 CAR-T cells, 92-28Z, 92-BBZ, 92-28BBZ, or mock co-cultured with HepG2 (HCC).
Figure 6B:
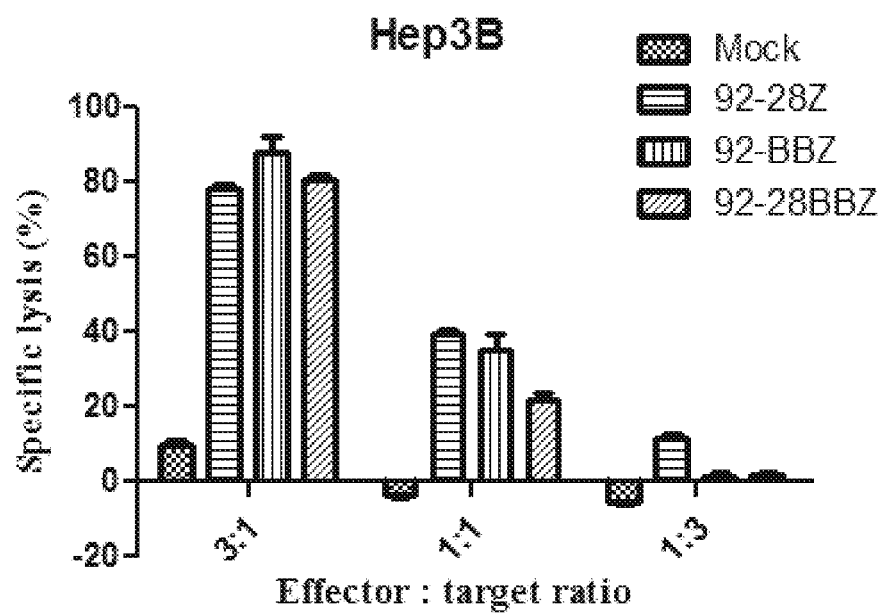
FIG. 6B shows a CytoTox 96® Non-Radioactive Cytotoxicity Assay performed on anti-GPC3 CAR-T cells, 92-28Z, 92-BBZ, 92-28BBZ, or mock co-cultured with Hep3B (HCC)
Figure 6C:
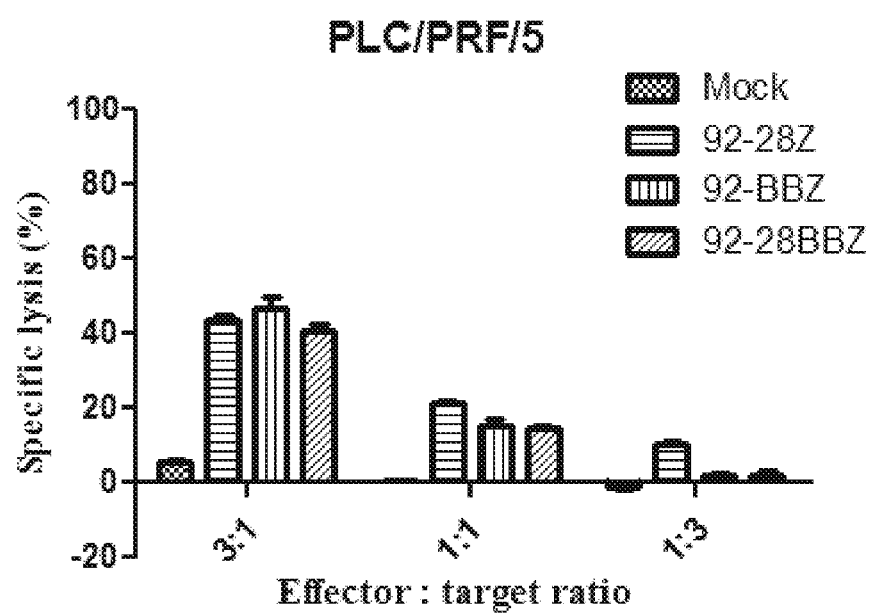
FIG. 6C shows a CytoTox 96® Non-Radioactive Cytotoxicity Assay performed on anti-GPC3 CAR-T cells, 92-28Z, 92-BBZ, 92-28BBZ, or mock co-cultured with or PLC/PRF/5 (Hepatoma).
Figure 7A:
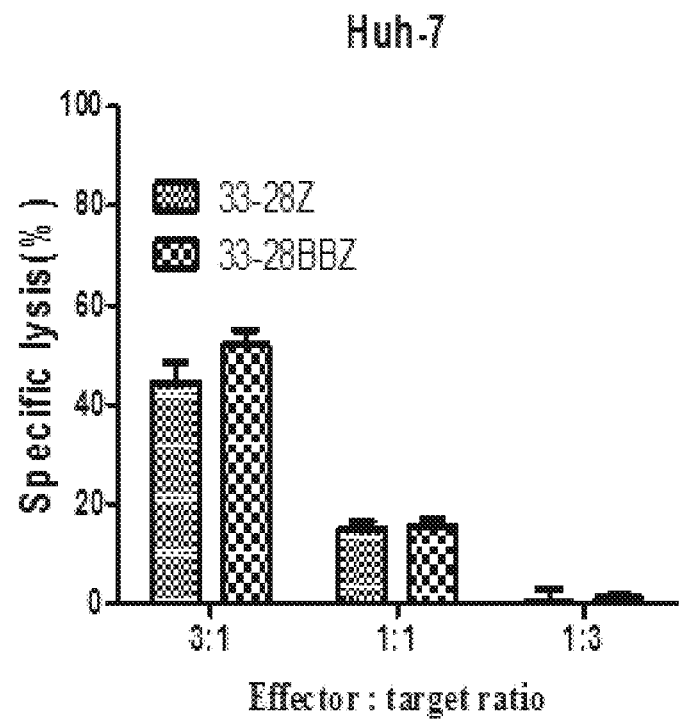
FIG. 7A shows a CytoTox 96® Non-Radioactive Cytotoxicity Assay performed on anti-GPC3 CAR-T cells, 33-28Z or 33-28BBZ co-cultured with Huh-7 cells at effector: target ratio of 3:1, 1:1, or 1:3.

To evaluate the potential cytotoxic effect of the second generation or third generation CAR-T transduced T cells, a CytoTox 96® Non-Radioactive Cytotoxicity Assay (Promega) was performed. Briefly, anti-GPC3 CAR-T cells, 92-28Z, 92-BBZ, 92-28BBZ, or mock were co-cultured with HepG2 (HCC)(FIG. 6A), Hep3B (HCC)(FIG. 6B), or PLC/PRF/5 (Hepatoma)(FIG. 6C) at effector: target ratio of 3:1, 1:1, or 1:3 with target cells at 10,000/well, and incubated for 18 hours at 37° C. To evaluate the cytotoxic effect of the second and third generation CAR-T a similar CytoTox 96® assay was performed using 92-28Z, 92-BBZ, 92-28BBZ, or mock co-cultured with high GPC3 expressing liver cancer cells, Huh-7, FIG. 7A. Visible wavelength absorbance data was collected using a standard 96-well plate reader post incubation.
Results Cytotoxicity data show that both second and third generation constructs had comparable cytotoxicity across all liver cancer panels including HCC and hepatoma tumor cell lines at 3:1, 1:1, and 1:3. The second and third generation contruts were able to target tumor cells of varying levels of GPC3 expression, revealing a broad range of tumor targeting potential.

Example 9: Cytotoxicity Assay: Gastric Carcinoma

Figure 7B:
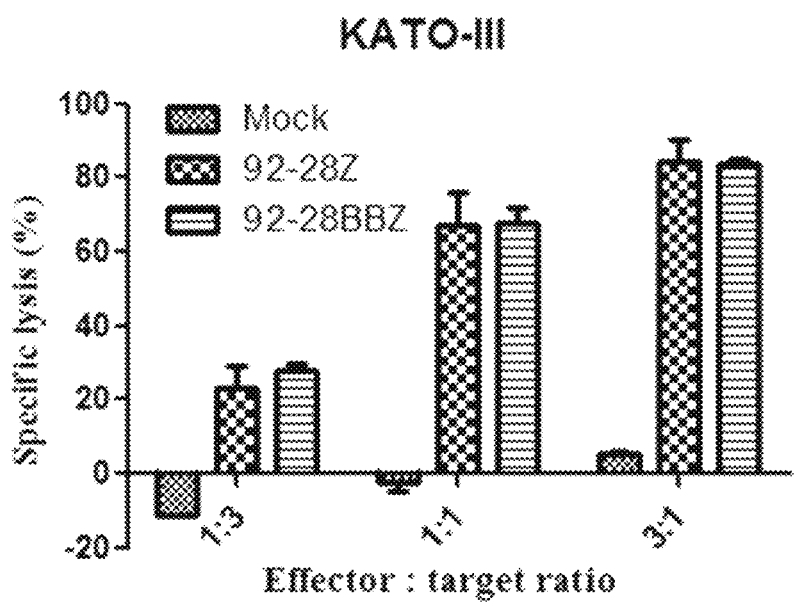
FIG. 7B shows a CytoTox 96® Non-Radioactive Cytotoxicity Assay performed on anti-GPC3 CAR-T cells, 92-28Z or 92-28BBZ co-cultured with a gastric carcinoma cell line KATO-III cells at effector: target ratio of 3:1, 1:1, or 1:3.

To evaluate the potential cytotoxic effect of the second generation or third generation CAR-T transduced T cells in a gastric carcinoma tumor setting, a CytoTox 96® Non-Radioactive Cytotoxicity Assay (Promega) was performed. Briefly, anti-GPC3 CAR-T cells, 92-28Z, 92-28BBZ, or mock were co-cultured with KATO-III at effector-to-target ratios of 1:3, 1:1, and 3:1 at 10,000/well, and incubated for 18 hours at 37° C.
Results Cytotoxicity data shows that both second and third generation constructs had comparable cytotoxicity against the gastric carcinoma tumor line, KATO-III, FIG. 7B, which mock transduced cells had no activity. Data suggests that CAR-T cells are specific to their tumor target and show no reactivity to tissues that does not express the GPC3 antigen.

Example 10: Comparison of scFv 33 Versus scFv 92

Figure 10A:
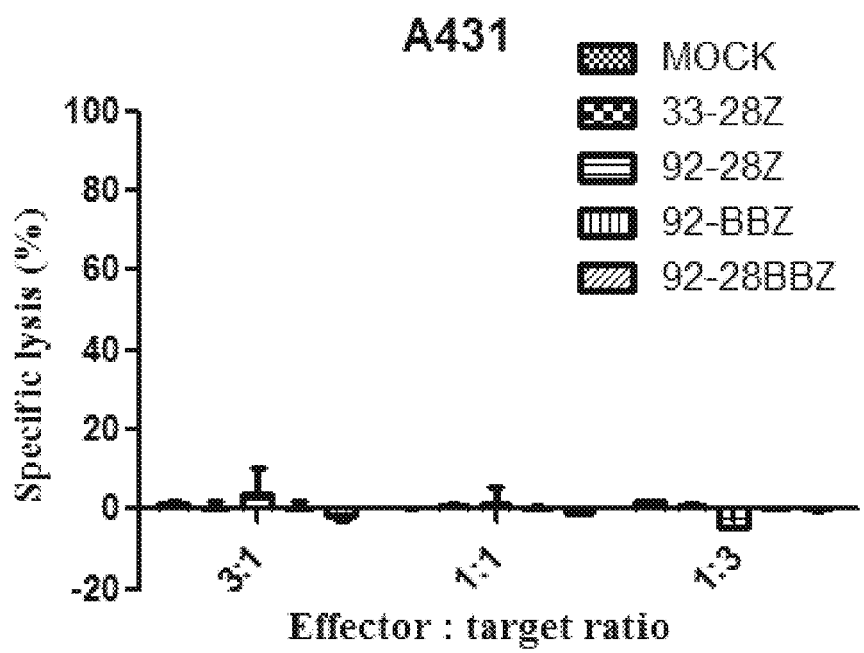
FIG. 10A shows a CytoTox 96® Non-Radioactive Cytotoxicity Assay performed on anti-GPC3 CAR-T cells, 33-28Z, 92-28Z, 92-BBZ, 92-28BBZ, or mock co-cultured with A431 (GPC3 neg).
Figure 10B:
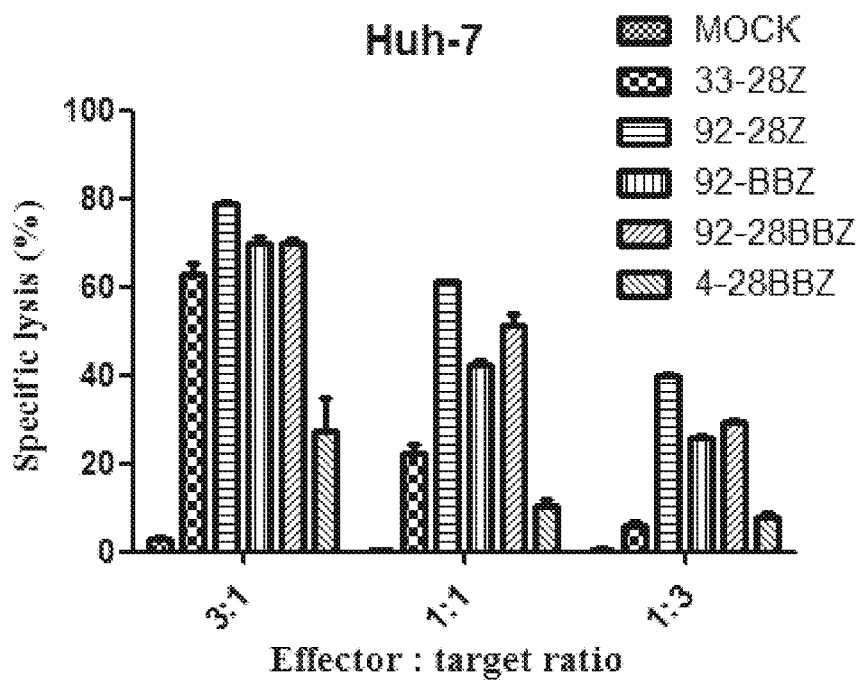
FIG. 10B shows a CytoTox 96® Non-Radioactive Cytotoxicity Assay performed on anti-GPC3 CAR-T cells, 33-28Z, 92-28Z, 92-BBZ, 92-28BBZ, or mock co-cultured with Huh-7 (GPC3 pos). CytoTox assays were all performed at effector: target ratio of 3:1, 1:1, or 1:3.

To compare CAR-T with different scFv's to GPC3, second generation or third generation CAR-T transduced T cells were used in a CytoTox 96® Non-Radioactive Cytotoxicity Assay (Promega). Briefly, anti-GPC3 CAR-T cells, 33-28Z, 92-28Z, 92-BBZ, 92-28BBZ, or mock were co-cultured with Huh-7 cells or control cells, A431 (GPC3 neg), at effector: target ratio of 3:1, 1:1, or 1:3 with target cells at 10,000/well, and incubated for 18 hours at 37° C.Visible wavelength absorbance data was collected using a standard 96-well plate reader post incubation.
Results Cytotoxicity data shows that constructs with the scFv 92 had increased cytotoxicy as compared to constructs with scFv 33 at 3:1, 1:1, and 1:3 effector to target ratios, FIG. 10B. Cytotoxicity was antigen specific as there was no cytotoxicity detected in the cocultured with the GPC3 neg tumor cell line A431, FIG. 10A.

Example 11: Comparison of Second and Third Generation CAR-T

Figure 9:
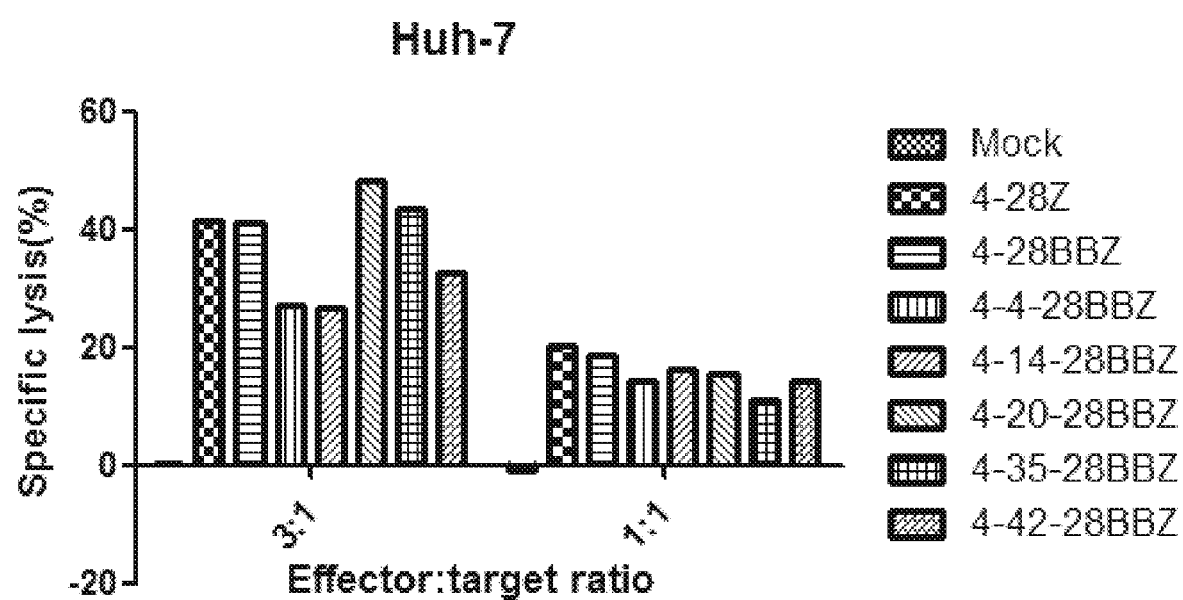
FIG. 9 shows specific lysis results of a cytoTox 96® Non-Radioactive Cytotoxicity Assay of various second and third generation anti-GPC3 CAR constructs: 4-28Z, 4-28BBZ, 4-4-28BBZ, 4-14-28BBZ, 4-20-28BBZ, 4-35-28BBZ, 4-42-28BBZ co-cultured with Huh7 (HCC) cells at effector: target ratio of 3:1, or 1:1.

To compare second and third generation CAR-T CAR-T transduced T cells were used in a CytoTox 96® Non-Radioactive Cytotoxicity Assay (Promega). Briefly, anti-GPC3 CAR-T cells, 4-28Z, 4-28BBZ, 4-4-28BBZ, 4-14-28BBZ, 4-20-28BBZ, 4-35-28BBZ, 4-42-28BBZ or mock-transduced were co-cultured with Huh7 (HCC) cells at effector: target ratio of 3:1, or 1:1 with target cells at 10,000/well, and incubated for 18 hours at 37° C. Visible wavelength absorbance data was collected using a standard 96-well plate reader post incubation.
Results Cytotoxicity data show that both second and third generation constructs had cytotoxicity with 4-20-28BBZ, 4-35-28BBZ, and 4-42-28BBZ having higher cycotoxicity as measured by increased lysis, FIG. 9.

Example 12: Proliferation Assay

Proliferation of anti-GPC3 CAR-T after exposure to target cells (Huh-7, GPC3+) or control cells (SK-HEP-1, GPC3-) is determined by carboxyfluorescein succinimidyl ester dilution assays.

One week post-transduction, control T lymphocytes and anti-GPC3 CAR-T cells are labeled with 1.5 µmol/L carboxyfluorescein diacetate succinimidyl ester (CFSE; Invitrogen) and plated with irradiated tumor targets (GPC3 positive and GPC3 negative lines) at an effector-to-target (E:

T) ratio of 5:1. CFSE dilution is measured on CD4+ and CD8+ T cells by flow cytometry on day 4 of co-culture.

Example 13: Patient Derived Tumor Graft Murine Model and Lymphocyte Reduction

Figure 8A:
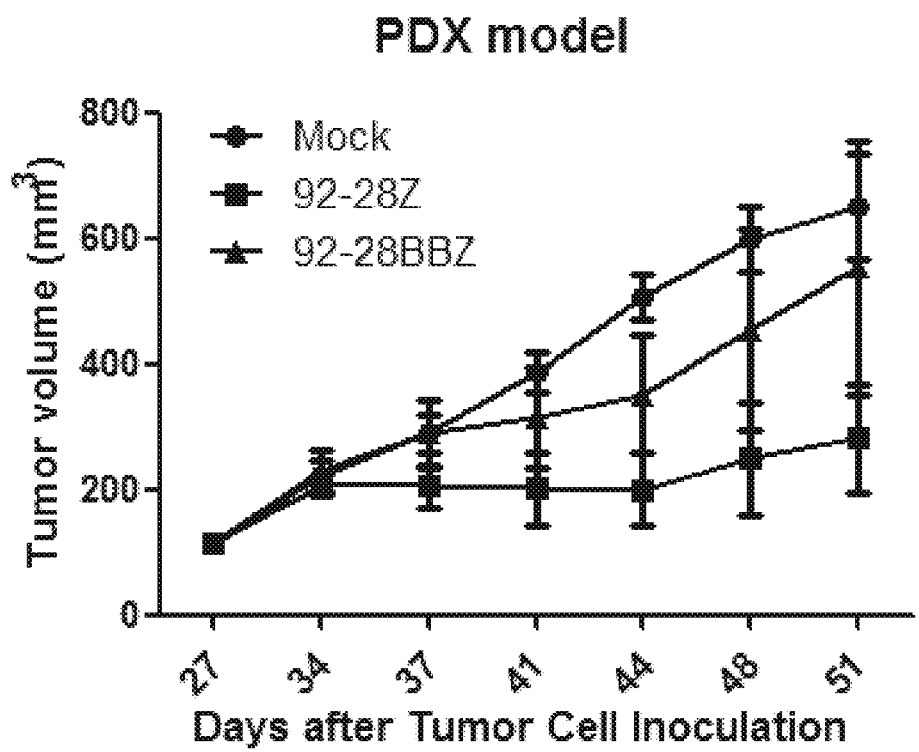
FIG. 8A shows that mice treated with 92-28Z, second generation CAR-T, had significantly reduced tumor size as compared to mice treated with 92-28BBZ, third generation CAR-T, or saline.
Figure 8B:
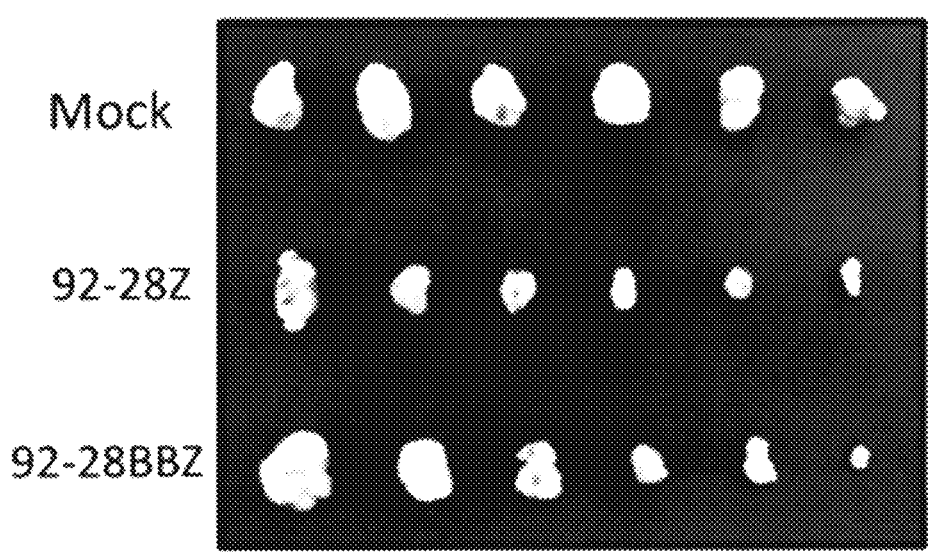
FIG. 8B shows an images of tumors that shows that mice engrafted with Huh-7 cells that were treated with 92-28Z, second generation CAR-T, had significantly reduced tumor size as compared to mice treated with 92-28BBZ, third generation CAR-T, or saline.
Figure 8C:
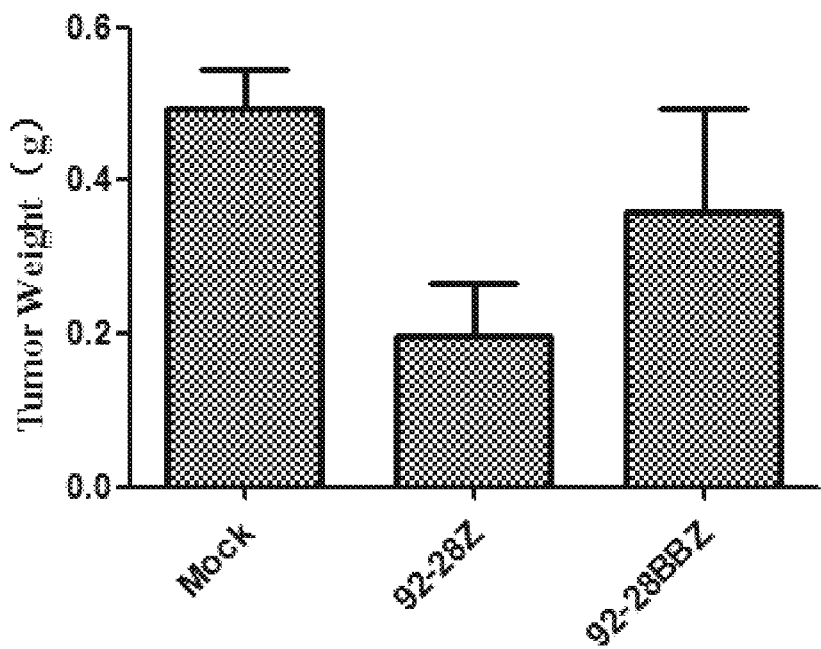
FIG. 8C shows mice treated with 92-28Z, second generation CAR-T, also had significantly reduced tumor weight as compared to mice treated with 92-28BBZ, third generation CAR-T, or saline.
Figure 8D:
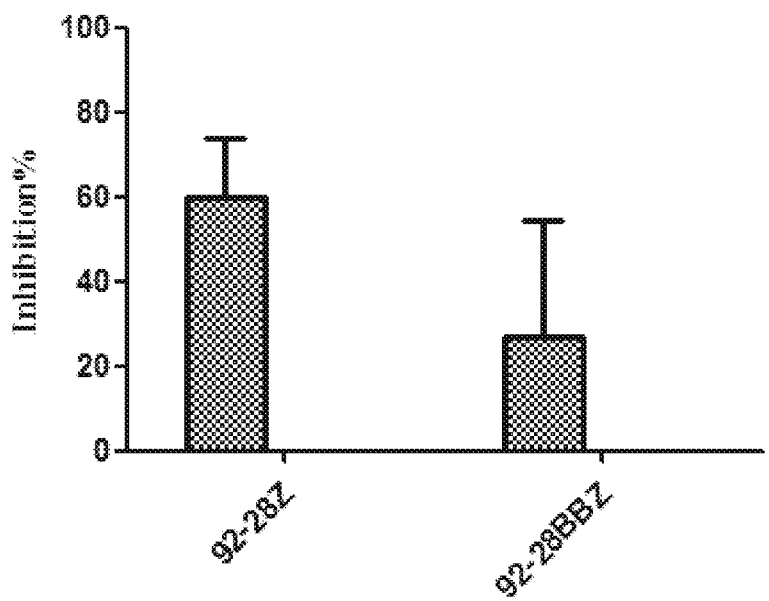
FIG. 8D shows mice treated with 92-28Z, second generation CAR-T, also had significantly reduced inhibition as compared to mice treated with 92-28BBZ, third generation CAR-T, or saline.

NOD/SCID mice were each implanted with 2×2×2 mm lung cancer tumors. On approximately day 27 post implantation or when tumor size, reached 220 mm³, mice were administered cyclophosphamide intravenously and either 1×10⁷ mock, hu92-28Z, or hu92-28BBZ CAR-T cells intraperitonealy. A second administration followed on day 34. Tumor volume was measured using caliper measurement approximately every 3-7 days until day 52 post tumor inoculation.
Results On day 51 post tumor inoculation, mice treated with 92-28Z, second generation CAR-T, had significantly reduced tumor size as compared to mice treated with 92-28BBZ, third generation CAR-T, or saline, FIG. 8A and FIG. 8B. Mice treated with 92-28Z, second generation CAR-T, also had significantly reduced tumor weight as compared to mice treated with 92-28BBZ, third generation CAR-T, or saline, FIG. 8C. Mice treated with 92-28Z, second generation CAR-T, also had significantly reduced inhibition as compared to mice treated with 92-28BBZ, third generation CAR-T, or saline, FIG. 8D.

Figure 11A:
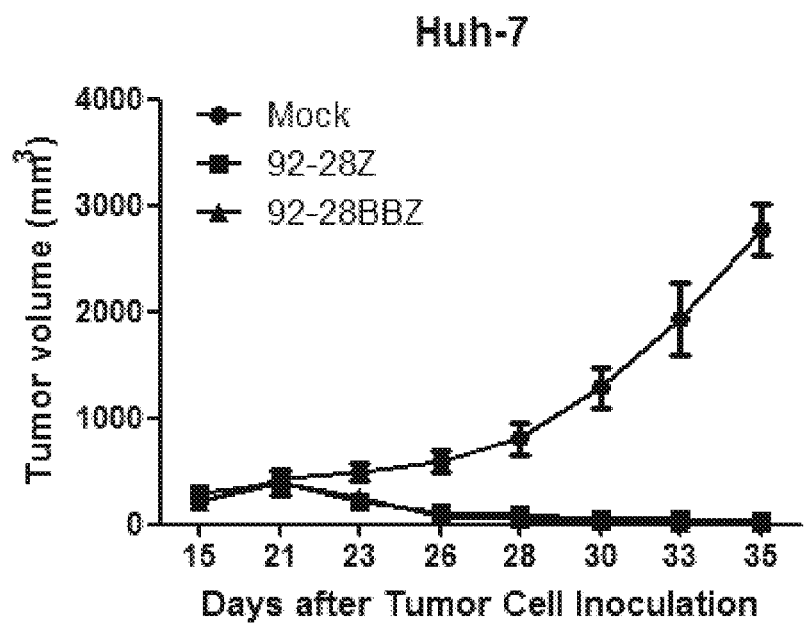
FIG. 11A shows results of a xenograft murine model where mice treated with 92-28Z, second generation CAR-T, had significantly reduced tumor volume (mm$^3$) as compared to mice treated with 92-28BBZ, third generation CAR-T, or mock.
Figure 11B:
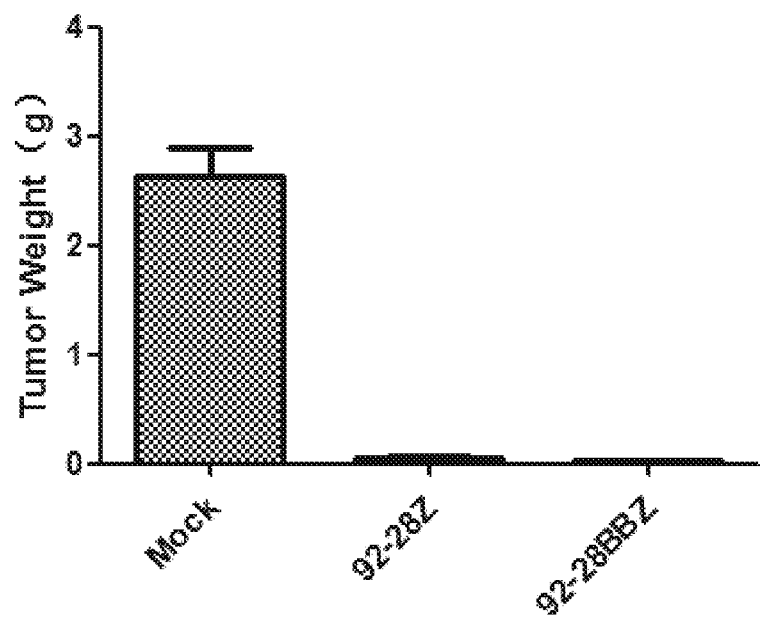
FIG. 11B shows that mice treated with 92-28Z, second generation CAR-T, had significantly reduced tumor weight as compared to mice treated with 92-28BBZ, third generation CAR-T, or saline.
Figure 11C:
FIG. 11C shows an image of tumors from mice treated with mock, 92-28BBZ, or 92-28Z CAR-T.

Example 14: Xenograft HCC Murine Model 8- to 12-week old NOD.Cg-Prkdc$^{scid}$Il2rg$^{tm1Wjl}$/SzJ (NSG) mice (Bar Harbor, Me.) were implanted with 0.5×10⁶ Huh-7 tumor cells on their left flank. 7 days post tumor inoculation mice were treated with 1×10⁷ mock-transduced T cells, hu92-28Z, or hu92-28BBZ by tail vein injection. Following treatment mice were monitored by caliper measurement at least once a week for 35 days post tumor cell inoculation.
Results Treatment with hu92-28Z and hu92-28BBZ had significant anti-tumor activity as compared to mice treated with mock-transduced T cells. FIG. 11A shows that mice treated with hu92-28Z or hu92-28BBZ had significantly reduced tumor volume on day 35 post tumor cell inoculation. FIG. 11B shows that mice treated with hu92-28Z or hu92-28BBZ had significantly smaller tumors as evidenced by their reduced weight measurements as compared to mice treated with mock transduced cells. FIG. 11C shows images of the xenograft tumors.

Example 15: Clinical Expansion of Anti-GPC3 CAR T Cells

In order to generate a large number of transduced T cells, the cells are induced to proliferate using a rapid expansion protocol (REP). Prior to being used in REPs, T cells are started in culture with anti-CD3, anti-CD28 and IL-2 and transduced on the second day after the initiation of culture as detailed above. The cells are cultured in a 75 cm² flask at 37° C. and 5% $CO_2$. The cells are counted and suspended at a concentration of 0.5×10⁶ cells/mL in fresh T cell medium with 300 IU/mL of IL-2 every two days for the remainder of the time they will be kept in culture.

Example 16: Clinical Trial

Patients with evaluable liver cancer undergo apheresis to isolate peripheral blood mononuclear cells. Lymphocytes are isolated, virally transduced with an anti-GPC3 CAR, expanded, and aliquots taken for immunologic testing. On days −7 and −6 before CAR-T administration, patients undergo a preparative regime of cyclophosphamide at 60 mg/kg/day×2 days IV over 1 hr. On days −7 and −3 before CAR-T administration, patients undergo a preparative regime of fludarabine 25 mg/m²/day IVPB daily over 30 minutes for 5 days. During the preparative regimen, patients undergo daily complete blood count (CBC) testing.

In the first part of a phase I study a dose escalation is initiated utilizing one patient per group starting at 10⁹ anti-GPC3 CAR-T per patient. Individual patients are treated at half log increments. Thus the following doses will be utilized: 10⁹, 3×10⁹ cells, 10¹⁰ cells, 3×10¹⁰ cells, and up to 1×10¹¹ cells. Autologous anti-GPC3 CAR-T are administered intravenously over 20 to 30 minutes via non-filtered tubing.

All patients return to the clinic for evaluation 6 weeks following administration of the CAR-T cell product.

TABLE 12

Sequences

| SEQ ID No | Sequence |
|---|---|
| 1 | QVQLQESGGGLVQPGRSLRLSCAASGFTFSSYAMHWVRQAPGKGLEWVSAISGSGGSTYYADS VKGRFTISRDNSKNTLYLQMNSLRAEDTAVYYCAKDRRGSHADAFDVWGQGTLVTVSSGGGGS GGGGSGGGGSQSALTQPPSASGSPGQSVTISCTGTSSDVGGYNYVSWYQQYPGKAPKLLIYGNS NRPSGVPDRFSGSKSGTSASLAITGLQAEDGADYYCQSYDSSLRVVFGGGTKVTVLG |
| 2 | QVQLQESGGGLVQPGRSLRLSCAASGFTFSTYAMNWVRQAPGKGLEWVSAISMSGESTYYADS VKGRFTISRDNSKNTLYLQMNSLRAEDTAVYYCAKDRRGSHADAFDVWGQGTLVTVSSGGGGS GGGGSGGGGSQSALTQPPSASGSPGQSVTISCTGTSSDVGGYNYVSWYQQYPGKAPKLLIYGNS NRPSGVPDRFSGSKSGTSASLAITGLQAEDGADYYCQSYDSSLRVVFGGGTKVTVLG |
| 3 | QVQLQESGGGLVQPGRSLRLSCAASGFTFSSYAMHWVRQAPGKGLEWVSAISSSGGSTYYADSV KGRFTISRDNSKNTLYLQMNSLRAEDTAVYYCAKDRRGSHADAFDVWGQGTLVTVSSGGGGSG GGGSGGGGSQSALTQPPSASGSPGQSVTISCTGTSSDVGHKFPVSWYQQYPGKAPKLLIYKNLLR PSGVPDRFSGSKSGTSASLAITGLQAEDGADYYCQSYDSSLRVVFGGGTKVTVLG |
| 4 | EVQLVQSGAEVKKPGASVKVSCKASGYTFSDYEMHWVRQAPGQGLEWMGAIHPGSGDTAYNQ RFKGRVTITADKSTSTAYMELSSLRSEDTAVYYCARFYSYAYWGQGTLVTVSAGGGGSGGGGS GGGGSDIVMTQTPLSLPVTPGEPASISCRSSQSLVHSNGNTYLQWYLQKPGQSPQLLIYKVSNRFS GVPDRFSGSGSGTDFTLKISRVEAEDVGVYYCSQSIYVPYTFGQGTKLEIKR |

TABLE 12-continued

Sequences

| SEQ ID No | Sequence |
|---|---|
| 5 | QVQLQESGGGLVQPGRSLRLSCAASGFTFSTYAMTWVRQAPGKGLEWVSSISSSGESTYYADSV<br>KGRFTISRDNSKNTLYLQMNSLRAEDTAVYYCAKDRRGSHADAFDVWGQGTLVTVSSGGGGSG<br>GGGSGGGGSQSALTQPPSASGSPGQSVTISCTGTSSDVGGYNYVSWYQQYPGKAPKLLIYGNSN<br>RPSGVPDRFSGSKSGTSASLAITGLQAEDGADYYCQSYDSSLRVVFGGGTKVTVLG |
| 6 | QVQLQESGGGLVQPGRSLRLSCAASGFTFSTYAMAWVRQAPGKGLEWVSEISSSGSRTYYADSV<br>KGRFTISRDNSKNTLYLQMNSLRAEDTAVYYCAKDRRGSHADAFDVWGQGTLVTVSSGGGGSG<br>GGGSGGGGSQSALTQPPSASGSPGQSVTISCTGTSSDVGGYNYVSWYQQYPGKAPKLLIYGNSN<br>RPSGVPDRFSGSKSGTSASLAITGLQAEDGADYYCQSYDSSLRVVFGGGTKVTVLG |
| 7 | QVQLQESGGGLVQPGRSLRLSCAASGFTFSSYAMHWVRQAPGKGLEWVSAISSSGGSTYYADSV<br>KGRFTISRDNSKNTLYLQMNSLRAEDTAVYYCAKDRRGSHADAFDVWGQGTLVTVSSGGGGSG<br>GGGSGGGGSQSALTQPPSASGSPGQSVTISCTGTSSDVGLMHNVSWYQQYPGKAPKLLIYKSSSR<br>PSGVPDRFSGSKSGTSASLAITGLQAEDGADYYCQSYDSSLRVVFGGGTKVTVLG |
| 8 | DVVMTQSPLSLPVTPGEPASISCRSSQSLVHSNANTYLHWYLQKPGQSPQLLIYKVSNRFSGVPD<br>RFSGSGSGTDFTLKISRVEAEDVGVYYCSQNTHVPPTFGQGTKLEIKRGGGSGGGGSGGGGSQ<br>VQLVQSGAEVKKPGASVKVSCKASGYTFTDYEMHWVRQAPGQGLEWMGALDPKTGDTAYSQ<br>KFKGRVTLTADESTSTAYMELSSLRSEDTAVYYCTRFYSYTYWGQGTLVTVSS |
| 9 | TTTPAPRPPTPAPTIASQPLSLRPEACRPAAGGAVHTRGLDFACD |
| 10 | FWVLVVVGGVLACYSLLVTVAFIIFWV |
| 11 | RSKRSRLLHSDYMNMTPRRPGPTRKHYQPYAPPRDFAAYRS |
| 12 | RVKFSRSADAPAYQQGQNQLYNELNLGRREEYDVLDKRRGRDPEMGGKPQRRKNPQEGLYNE<br>LQKDKMAEAYSEIGMKGERRRGKGHDGLYQGLSTATKDTYDALHMQALPPR |
| 13 | KRGRKKLLYIFKQPFMRPVQTTQEEDGCSCRFPEEEEGGCEL |
| 14 | QVQLQESGGGLVQPGRSLRLSCAASGFTFSSYAMHWVRQAPGKGLEWVSAISGSGGSTYYADS<br>VKGRFTISRDNSKNTLYLQMNSLRAEDTAVYYCAKDRRGSHADAFDVWGQGTLVTVSSGGGGS<br>GGGGSGGGGSQSALTQPPSASGSPGQSVTISCTGTSSDVGGYNYVSWYQQYPGKAPKLLIYGNS<br>NRPSGVPDRFSGSKSGTSASLAITGLQAEDGADYYCQSYDSSLRVVFGGGTKVTVLGTTTPAPRP<br>PTPAPTIASQPLSLRPEACRPAAGGAVHTRGLDFACDFWVLVVVGGVLACYSLLVTVAFIIFWVR<br>SKRSRLLHSDYMNMTPRRPGPTRKHYQPYAPPRDFAAYRSRVKFSRSADAPAYQQGQNQLYNE<br>LNLGRREEYDVLDKRRGRDPEMGGKPQRRKNPQEGLYNELQKDKMAEAYSEIGMKGERRRGK<br>GHDGLYQGLSTATKDTYDALHMQALPPR |
| 15 | QVQLQESGGGLVQPGRSLRLSCAASGFTFSSYAMHWVRQAPGKGLEWVSAISGSGGSTYYADS<br>VKGRFTISRDNSKNTLYLQMNSLRAEDTAVYYCAKDRRGSHADAFDVWGQGTLVTVSSGGGGS<br>GGGGSGGGGSQSALTQPPSASGSPGQSVTISCTGTSSDVGGYNYVSWYQQYPGKAPKLLIYGNS<br>NRPSGVPDRFSGSKSGTSASLAITGLQAEDGADYYCQSYDSSLRVVFGGGTKVTVLGTTTPAPRP<br>PTPAPTIASQPLSLRPEACRPAAGGAVHTRGLDFACDFWVLVVVGGVLACYSLLVTVAFIIFWVR<br>SKRSRLLHSDYMNMTPRRPGPTRKHYQPYAPPRDFAAYRSKRGRKKLLYIFKQPFMRPVQTTQE<br>EDGCSCRFPEEEEGGCELRVKFSRSADAPAYQQGQNQLYNELNLGRREEYDVLDKRRGRDPEM<br>GGKPQRRKNPQEGLYNELQKDKMAEAYSEIGMKGERRRGKGHDGLYQGLSTATKDTYDALHM<br>QALPPR |
| 16 | QVQLQESGGGLVQPGRSLRLSCAASGFTFSTYAMTWVRQAPGKGLEWVSSISSSGESTYYADSV<br>KGRFTISRDNSKNTLYLQMNSLRAEDTAVYYCAKDRRGSHADAFDVWGQGTLVTVSSGGGGSG<br>GGGSGGGGSQSALTQPPSASGSPGQSVTISCTGTSSDVGGYNYVSWYQQYPGKAPKLLIYGNSN<br>RPSGVPDRFSGSKSGTSASLAITGLQAEDGADYYCQSYDSSLRVVFGGGTKVTVLGTTTPAPRPP<br>TPAPTIASQPLSLRPEACRPAAGGAVHTRGLDFACDFWVLVVVGGVLACYSLLVTVAFIIFWVRS<br>KRSRLLHSDYMNMTPRRPGPTRKHYQPYAPPRDFAAYRSKRGRKKLLYIFKQPFMRPVQTTQEE<br>DGCSCRFPEEEEGGCELRVKFSRSADAPAYQQGQNQLYNELNLGRREEYDVLDKRRGRDPEMG<br>GKPQRRKNPQEGLYNELQKDKMAEAYSEIGMKGERRRGKGHDGLYQGLSTATKDTYDALHMQ<br>ALPPR |
| 17 | QVQLQESGGGLVQPGRSLRLSCAASGFTFSTYAMTWVRQAPGKGLEWVSSISSSGESTYYADSV<br>KGRFTISRDNSKNTLYLQMNSLRAEDTAVYYCAKDRRGSHADAFDVWGQGTLVTVSSGGGGSG<br>GGGSGGGGSQSALTQPPSASGSPGQSVTISCTGTSSDVGGYNYVSWYQQYPGKAPKLLIYGNSN<br>RPSGVPDRFSGSKSGTSASLAITGLQAEDGADYYCQSYDSSLRVVFGGGTKVTVLGTTTPAPRPP<br>TPAPTIASQPLSLRPEACRPAAGGAVHTRGLDFACDFWVLVVVGGVLACYSLLVTVAFIIFWVRS<br>KRSRLLHSDYMNMTPRRPGPTRKHYQPYAPPRDFAAYRSVKFSRSADAPAYQQGQNQLYNEL<br>NLGRREEYDVLDKRRGRDPEMGGKPQRRKNPQEGLYNELQKDKMAEAYSEIGMKGERRRGKG<br>HDGLYQGLSTATKDTYDALHMQALPPR |
| 18 | QVQLQESGGGLVQPGRSLRLSCAASGFTFSTYAMAWVRQAPGKGLEWVSEISSSGSRTYYADSV<br>KGRFTISRDNSKNTLYLQMNSLRAEDTAVYYCAKDRRGSHADAFDVWGQGTLVTVSSGGGGSG<br>GGGSGGGGSQSALTQPPSASGSPGQSVTISCTGTSSDVGGYNYVSWYQQYPGKAPKLLIYGNSN<br>RPSGVPDRFSGSKSGTSASLAITGLQAEDGADYYCQSYDSSLRVVFGGGTKVTVLGTTTPAPRPP<br>TPAPTIASQPLSLRPEACRPAAGGAVHTRGLDFACDFWVLVVVGGVLACYSLLVTVAFIIFWVRS<br>KRSRLLHSDYMNMTPRRPGPTRKHYQPYAPPRDFAAYRSKRGRKKLLYIFKQPFMRPVQTTQEE |

TABLE 12-continued

Sequences

| SEQ ID No | Sequence |
|---|---|
| | DGCSCRFPEEEEGGCELRVKFSRSADAPAYQQGQNQLYNELNLGRREEYDVLDKRRGRDPEMG GKPQRRKNPQEGLYNELQKDKMAEAYSEIGMKGERRRGKGHDGLYQGLSTATKDTYDALHMQ ALPPR |
| 19 | QVQLQESGGGLVQPGRSLRLSCAASGFTFSTYAMAWVRQAPGKGLEWVSEISSSGSRTYYADSV KGRFTISRDNSKNTLYLQMNSLRAEDTAVYYCAKDRRGSHADAFDVWGQGTLVTVSSGGGGSG GGGSGGGGSQSALTQPPSASGSPGQSVTISCTGTSSDVGGYNYVSWYQQYPGKAPKLLIYGNSN RPSGVPDRFSGSKSGTSASLAITGLQAEDGADYYCQSYDSSLRVVFGGGTKVTVLGTTTPAPRPP TPAPTIASQPLSLRPEACRPAAGGAVHTRGLDFACDFWVLVVVGGVLACYSLLVTVAFIIFWVRS KRSRLLHSDYMNMTPRRPGPTRKHYQPYAPPRDFAAYRSRVKFSRSADAPAYQQGQNQLYNEL NLGRREEYDVLDKRRGRDPEMGGKPQRRKNPQEGLYNELQKDKMAEAYSEIGMKGERRRGKG HDGLYQGLSTATKDTYDALHMQALPPR |
| 20 | QVQLQESGGGLVQPGRSLRLSCAASGFTFSTYAMNWVRQAPGKGLEWVSAISMSGESTYYADS VKGRFTISRDNSKNTLYLQMNSLRAEDTAVYYCAKDRRGSHADAFDVWGQGTLVTVSSGGGGS GGGGSGGGGSQSALTQPPSASGSPGQSVTISCTGTSSDVGGYNYVSWYQQYPGKAPKLLIYGNS NRPSGVPDRFSGSKSGTSASLAITGLQAEDGADYYCQSYDSSLRVVFGGGTKVTVLGTTTPAPRP PTPAPTIASQPLSLRPEACRPAAGGAVHTRGLDFACDFWVLVVVGGVLACYSLLVTVAFIIFWVR SKRSRLLHSDYMNMTPRRPGPTRKHYQPYAPPRDFAAYRS KRGRKKLLYIFKQPFMRPVQTTQEEDGCSCRFPEEEEGGCELRVKFSRSADAPAYQQGQNQLYN ELNLGRREEYDVLDKRRGRDPEMGGKPQRRKNPQEGLYNELQKDKMAEAYSEIGMKGERRRG KGHDGLYQGLSTATKDTYDALHMQALPPR |
| 21 | QVQLQESGGGLVQPGRSLRLSCAASGFTFSTYAMNWVRQAPGKGLEWVSAISMSGESTYYADS VKGRFTISRDNSKNTLYLQMNSLRAEDTAVYYCAKDRRGSHADAFDVWGQGTLVTVSSGGGGS GGGGSGGGGSQSALTQPPSASGSPGQSVTISCTGTSSDVGGYNYVSWYQQYPGKAPKLLIYGNS NRPSGVPDRFSGSKSGTSASLAITGLQAEDGADYYCQSYDSSLRVVFGGGTKVTVLGTTTPAPRP PTPAPTIASQPLSLRPEACRPAAGGAVHTRGLDFACDFWVLVVVGGVLACYSLLVTVAFIIFWVR SKRSRLLHSDYMNMTPRRPGPTRKHYQPYAPPRDFAAYRSRVKFSRSADAPAYQQGQNQLYNE LNLGRREEYDVLDKRRGRDPEMGGKPQRRKNPQEGLYNELQKDKMAEAYSEIGMKGERRRGK GHDGLYQGLSTATKDTYDALHMQALPPR |
| 22 | QVQLQESGGGLVQPGRSLRLSCAASGFTFSSYAMHWVRQAPGKGLEWVSAISSSGGSTYYADSV KGRFTISRDNSKNTLYLQMNSLRAEDTAVYYCAKDRRGSHADAFDVWGQGTLVTVSSGGGGSG GGGSGGGGSQSALTQPPSASGSPGQSVTISCTGTSSDVGHKFPVSWYQQYPGKAPKLLIYKNLLR PSGVPDRFSGSKSGTSASLAITGLQAEDGADYYCQSYDSSLRVVFGGGTKVTVLGTTTPAPRPPT PAPTIASQPLSLRPEACRPAAGGAVHTRGLDFACDFWVLVVVGGVLACYSLLVTVAFIIFWVRSK RSRLLHSDYMNMTPRRPGPTRKHYQPYAPPRDFAAYRSKRGRKKLLYIFKQPFMRPVQTTQEED GCSCRFPEEEEGGCELRVKFSRSADAPAYQQGQNQLYNELNLGRREEYDVLDKRRGRDPEMGG KPQRRKNPQEGLYNELQKDKMAEAYSEIGMKGERRRGKGHDGLYQGLSTATKDTYDALHMQA LPPR |
| 23 | QVQLQESGGGLVQPGRSLRLSCAASGFTFSSYAMHWVRQAPGKGLEWVSAISSSGGSTYYADSV KGRFTISRDNSKNTLYLQMNSLRAEDTAVYYCAKDRRGSHADAFDVWGQGTLVTVSSGGGGSG GGGSGGGGSQSALTQPPSASGSPGQSVTISCTGTSSDVGHKFPVSWYQQYPGKAPKLLIYKNLLR PSGVPDRFSGSKSGTSASLAITGLQAEDGADYYCQSYDSSLRVVFGGGTKVTVLGTTTPAPRPPT PAPTIASQPLSLRPEACRPAAGGAVHTRGLDFACDFWVLVVVGGVLACYSLLVTVAFIIFWVRSK RSRLLHSDYMNMTPRRPGPTRKHYQPYAPPRDFAAYRSVKFSRSADAPAYQQGQNQLYNELN LGRREEYDVLDKRRGRDPEMGGKPQRRKNPQEGLYNELQKDKMAEAYSEIGMKGERRRGKGH DGLYQGLSTATKDTYDALHMQALPPR |
| 24 | QVQLQESGGGLVQPGRSLRLSCAASGFTFSSYAMHWVRQAPGKGLEWVSAISSSGGSTYYADSV KGRFTISRDNSKNTLYLQMNSLRAEDTAVYYCAKDRRGSHADAFDVWGQGTLVTVSSGGGGSG GGGSGGGGSQSALTQPPSASGSPGQSVTISCTGTSSDVGLMHNVSWYQQYPGKAPKLLIYKSSSR PSGVPDRFSGSKSGTSASLAITGLQAEDGADYYCQSYDSSLRVVFGGGTKVTVLGTTTPAPRPPT PAPTIASQPLSLRPEACRPAAGGAVHTRGLDFACDFWVLVVVGGVLACYSLLVTVAFIIFWVRSK RSRLLHSDYMNMTPRRPGPTRKHYQPYAPPRDFAAYRSKRGRKKLLYIFKQPFMRPVQTTQEED GCSCRFPEEEEGGCELRVKFSRSADAPAYQQGQNQLYNELNLGRREEYDVLDKRRGRDPEMGG KPQRRKNPQEGLYNELQKDKMAEAYSEIGMKGERRRGKGHDGLYQGLSTATKDTYDALHMQA LPPR |
| 25 | QVQLQESGGGLVQPGRSLRLSCAASGFTFSSYAMHWVRQAPGKGLEWVSAISSSGGSTYYADSV KGRFTISRDNSKNTLYLQMNSLRAEDTAVYYCAKDRRGSHADAFDVWGQGTLVTVSSGGGGSG GGGSGGGGSQSALTQPPSASGSPGQSVTISCTGTSSDVGLMHNVSWYQQYPGKAPKLLIYKSSSR PSGVPDRFSGSKSGTSASLAITGLQAEDGADYYCQSYDSSLRVVFGGGTKVTVLGTTTPAPRPPT PAPTIASQPLSLRPEACRPAAGGAVHTRGLDFACDFWVLVVVGGVLACYSLLVTVAFIIFWVRSK RSRLLHSDYMNMTPRRPGPTRKHYQPYAPPRDFAAYRSVKFSRSADAPAYQQGQNQLYNELN LGRREEYDVLDKRRGRDPEMGGKPQRRKNPQEGLYNELQKDKMAEAYSEIGMKGERRRGKGH DGLYQGLSTATKDTYDALHMQALPPR |
| 26 | DVVMTQSPLSLPVTPGEPASISCRSSQSLVHSNANTYLHWYLQKPGQSPQLLIYKVSNRFSGVPD RFSGSGSGTDFTLKISRVEAEDVGVYYCSQNTHVPPTFGQGTKLEIKRGGGGSGGGGSGGGGSQ VQLVQSGAEVKKPGASVKVSCKASGYTFTDYEMHWVRQAPGQGLEWMGALDPKTGDTAYSQ KFKGRVTLTADESTSTAYMELSSLRSEDTAVYYCTRFYSYTYWGQGTLVTVSSTTTPAPRPPTPA PTIASQPLSLRPEACRPAAGGAVHTRGLDFACDFWVLVVVGGVLACYSLLVTVAFIIFWVRSKRS |

TABLE 12-continued

Sequences

| SEQ ID No | Sequence |
|---|---|
| | RLLHSDYMNMTPRRPGPTRKHYQPYAPPRDFAAYRSRVKFSRSADAPAYQQGQNQLYNELNLG<br>RREEYDVLDKRRGRDPEMGGKPQRRKNPQEGLYNELQKDKMAEAYSEIGMKGERRRGKGHDG<br>LYQGLSTATKDTYDALHMQALPPR |
| 27 | DVVMTQSPLSLPVTPGEPASISCRSSQSLVHSNANTYLHWYLQKPGQSPQLLIYKVSNRFSGVPD<br>RFSGSGSGTDFTLKISRVEAEDVGVYYCSQNTHVPPTFGQGTKLEIKRGGGGSGGGGSGGGGSQ<br>VQLVQSGAEVKKPGASVKVSCKASGYTFTDYEMHWVRQAPGQGLEWMGALDPKTGDTAYSQ<br>KFKGRVTLTADESTSTAYMELSSLRSEDTAVYYCTRFYSYTYWGQGTLVTVSSTTTPAPRPPTPA<br>PTIASQPLSLRPEACRPAAGGAVHTRGLDFACDFWVLVVVGGVLACYSLLVTVAFIIFWVRSKRS<br>RLLHSDYMNMTPRRPGPTRKHYQPYAPPRDFAAYRSKRGRKKLLYIFKQPFMRPVQTTQEEDGC<br>SCRFPEEEEGGCELRVKFSRSADAPAYQQGQNQLYNELNLGRREEYDVLDKRRGRDPEMGGKP<br>QRRKNPQEGLYNELQKDKMAEAYSEIGMKGERRRGKGHDGLYQGLSTATKDTYDALHMQALP<br>PR |
| 28 | EVQLVQSGAEVKKPGASVKVSCKASGYTFSDYEMHWVRQAPGQGLEWMGAIHPGSGDTAYNQ<br>RFKGRVTITADKSTSTAYMELSSLRSEDTAVYYCARFYSYAYWGQGTLVTVSAGGGGSGGGGS<br>GGGGSDIVMTQTPLSLPVTPGEPASISCRSSQSLVHSNGNTYLQWYLQKPGQSPQLLIYKVSNRFS<br>GVPDRFSGSGSGTDFTLKISRVEAEDVGVYYCSQSIYVPYTFGQGTKLEIKRTTTPAPRPPTPAPTI<br>ASQPLSLRPEACRPAAGGAVHTRGLDFACDFWVLVVVGGVLACYSLLVTVAFIIFWVRSKRSRL<br>LHSDYMNMTPRRPGPTRKHYQPYAPPRDFAAYRSRVKFSRSADAPAYQQGQNQLYNELNLGRR<br>EEYDVLDKRRGRDPEMGGKPQRRKNPQEGLYNELQKDKMAEAYSEIGMKGERRRGKGHDGLY<br>QGLSTATKDTYDALHMQALPPR |
| 29 | EVQLVQSGAEVKKPGASVKVSCKASGYTFSDYEMHWVRQAPGQGLEWMGAIHPGSGDTAYNQ<br>RFKGRVTITADKSTSTAYMELSSLRSEDTAVYYCARFYSYAYWGQGTLVTVSAGGGGSGGGGS<br>GGGGSDIVMTQTPLSLPVTPGEPASISCRSSQSLVHSNGNTYLQWYLQKPGQSPQLLIYKVSNRFS<br>GVPDRFSGSGSGTDFTLKISRVEAEDVGVYYCSQSIYVPYTFGQGTKLEIKRTTTPAPRPPTPAPTI<br>ASQPLSLRPEACRPAAGGAVHTRGLDFACDIYIWAPLAGTGVLLLSLVITLYCKRGRKKLLYIF<br>KQPFMRPVQTTQEEDGCSCRFPEEEEGGCELRVKFSRSADAPAYKQGQNQLYNELNLGRREEYD<br>VLDKRRGRDPEMGGKPRRKNPQEGLYNELQKDKMAEAYSEIGMKGERRRGKGHDGLYQGLST<br>ATKDTYDALHMQALPPR |
| 30 | EVQLVQSGAEVKKPGASVKVSCKASGYTFSDYEMHWVRQAPGQGLEWMGAIHPGSGDTAYNQ<br>RFKGRVTITADKSTSTAYMELSSLRSEDTAVYYCARFYSYAYWGQGTLVTVSAGGGGSGGGGS<br>GGGGSDIVMTQTPLSLPVTPGEPASISCRSSQSLVHSNGNTYLQWYLQKPGQSPQLLIYKVSNRFS<br>GVPDRFSGSGSGTDFTLKISRVEAEDVGVYYCSQSIYVPYTFGQGTKLEIKRTTTPAPRPPTPAPTI<br>ASQPLSLRPEACRPAAGGAVHTRGLDFACDFWVLVVVGGVLACYSLLVTVAFIIFWVRSKRSRL<br>LHSDYMNMTPRRPGPTRKHYQPYAPPRDFAAYRSKRGRKKLLYIFKQPFMRPVQTTQEEDGCSC<br>RFPEEEEGGCELRVKFSRSADAPAYQQGQNQLYNELNLGRREEYDVLDKRRGRDPEMGGKPQR<br>RKNPQEGLYNELQKDKMAEAYSEIGMKGERRRGKGHDGLYQGLSTATKDTYDALHMQALPPR |
| 31 | GCAGGGGAAAGAATAGTAGACA |
| 32 | CGGCCTGGCGGCGTGGAG |
| 33 | GCAGGGGAAAGAATAGTAGACATAATAGCAACAGACATACAAACTAAAGAATTACAAAAA<br>CAAATTACAAAAATTCAAAATTTTATCGATGGCTCCGGTGCCCGTCAGTGGGCAGAGCGC<br>ACATCGCCCACAGTCCCCGAGAAGTTGGGGGGAGGGGTCGGCAATTGAACCGGTGCCTAG<br>AGAAGGTGGCGCGGGGTAAACTGGGAAAGTGATGTCGTGTACTGGCTCCGCCTTTTTCCC<br>GAGGGTGGGGGAGAACCGTATATAAGTGCAGTAGTCGCCGTGAACGTTCTTTTTCGCAAC<br>GGGTTTGCCGCCAGAACACAGGTGTCGTGACGCGGATCCAGGCCTAAGCTTACGCGTCCT<br>AGCGCTACCGGTCGCCACCATGGCCTTACCAGTGACCGCCTTGCTCCTGCCGCTGGCCTT<br>GCTGCTCCACGCCGCCAGGCCG |
| 34 | CTCCACGCCGCCAGGCCGGAGGTGCAGCTGGTGCAG |
| 35 | GCGGTGTCCTCGCTCCGCAGGCTGCTCAGCTCCATGTAGGCGGTG |
| 36 | GCGGAGCGAGGACACCGCCGTGTACTACTGCGCCCGGTTCTACAGCTAC |
| 37 | CGGCGCTGGCGTCGTGGTACGTTTGATCTCCAGCTTGGTG |
| 38 | CTCCACGCCGCCAGGCCGGAGGTGCAGCTGGTGCAGAGCGGCGCCGAGGTGAAGAAGCCCG<br>GCGCCAGCGTGAAGGTGAGCTGCAAGGCCAGCGGCTACACCTTCAGCGACTACGAGATGCA<br>CTGGGTGCGGCAGGCCCCCGGCCAGGGCCTGGAGTGGATGGGCGCCATCCACCCCGGCAGC<br>GGCGACACCGCCTACAACCAGCGGTTCAAGGGCCGGGTGACCATCACCGCCGACAAGAGCA<br>CCAGCACCGCCTACATGGAGCTGAGCAGCCTGCGGAGCGAGGACACCGCCGTGTACTACTG<br>CGCCCGGTTCTACAGCTACGCCTACTGGGGCCAGGGCACCCTGGTGACCGTGAGCGCCGGTG<br>GAGGCGGTTCAGGCGGAGGTGGTTCTGGCGGTGGCGGATCGGACATCGTGATGACCCAGAC<br>CCCCCTGAGCCTGCCCGTGACCCCCGGCGAGCCCGCCAGCATCAGCTGCCGGAGCAGCCAG<br>AGCCTGGTGCACAGCAACGGCAACACCTACCTGCAGTGGTACCTGCAGAAGCCCGGCCAGA<br>GCCCCCAGCTGCTGATCTACAAGGTGAGCAACCGGTTCAGCGGCGTGCCCGACCGGTTCAGC<br>GGCAGCGGCAGCGGCACCGACTTCACCCTGAAGATCAGCCGGGTGGAGGCCGAGGACGTGG<br>GCGTGTACTACTGCAGCCAGAGCATCTACGTGCCCTACACCTTCGGCCAGGGCACCAAGCTG<br>GAGATCAAACGTACCACGACGCCAGCGCCG |

TABLE 12-continued

Sequences

| SEQ ID No | Sequence |
|---|---|
| 39 | ACCACGACGCCAGCGCCG |
| 40 | AATCCAGAGGTTGATTGTCGACCTAGCGAGGGGGCAGGGCCTGC |
| 41 | ACCACGACGCCAGCGCCGCGACCACCAACACCGGCGCCCACCATCGCGTCGCAGCCCCTGTC<br>CCTGCGCCCAGAGGCGTGCCGGCCAGCGGCGGGGGGCGCAGTGCACACGAGGGGGCTGGAC<br>TTCGCCTGTGATTTTTGGGTGCTGGTGGTGGTTGGTGGAGTCCTGGCTTGCTATAGCTTGCTA<br>GTAACAGTGGCCTTTATTATTTTCTGGGTGAGGAGTAAGAGGAGCAGGCTCCTGCACAGTGA<br>CTACATGAACATGACTCCCCGCCGCCCCGGGCCAACCCGCAAGCATTACCAGCCCTATGCCC<br>CACCACGCGACTTCGCAGCCTATCGCTCCAGAGTGAAGTTCAGCAGGAGCGCAGACGCCCCC<br>GCGTACCAGCAGGGCCAGAACCAGCTCTATAACGAGCTCAATCTAGGACGAAGAGAGGAGT<br>ACGATGTTTTGGACAAGAGACGTGGCCGGGACCCTGAGATGGGGGGAAAGCCGCAGAGAAG<br>GAAGAACCCTCAGGAAGGCCTGTACAATGAACTGCAGAAAGATAAGATGGCGGAGGCCTAC<br>AGTGAGATTGGGATGAAAGGCGAGCGCCGGAGGGGCAAGGGGCACGATGGCCTTTACCAGG<br>GTCTCAGTACAGCCACCAAGGACACCTACGACGCCCTTCACATGCAGGCCCTGCCCCCTCGC<br>TAGGTCGACAATCAACCTCTGGATT |

What is claimed is:

1. A method of treating a subject exhibiting a solid tumor that expresses Glypican-3 (GPC3), the method comprising administering anti-GPC3 chimeric antigen receptor immunoresponsive cells to the subject, wherein the administering takes place after or concurrent with subjecting the subject to a lymphocyte reduction treatment, and wherein the lymphocyte reduction treatment comprises administering cyclophosphamide and fludarabine to the subject.

2. The method of claim 1, wherein the immunoresponsive cells are NK cells (anti-GPC3-CAR NK cells) or T cells (anti-GPC3-CAR T cells).

3. The method of claim 2, wherein the administering the anti-GPC3-CAR T cells to the subject takes place after subjecting the subject to the lymphocyte reduction treatment.

4. The method of claim 2, wherein at least about $5 \times 10^4$ anti-GPC3-CAR T cells/kg are administered to the subject.

5. The method of claim 2, wherein from about $5 \times 10^4$ to about $1 \times 10^{12}$ anti-GPC3-CAR T cells/kg are administered to the subject.

6. The method of claim 1, wherein the administration is effective in reducing tumor size by at least 30% as measured by computerized tomography (CT) scan.

7. The method of claim 1, wherein the administration is effective in stabilizing tumor size as measured by a less than 10% change in a baseline measurement of a diameter of the tumor lesion as measured by computerized tomography (CT) scan.

8. The method of claim 2, wherein the administering of anti-GPC3-CAR T cells and the subjecting the subject to the lymphocyte reduction treatment synergistically increase the subject's medium survival time by at least about 6 months as compared to administering the anti-GPC3-CAR T cells alone.

9. The method of claim 1, wherein the solid tumor is liver cancer, stomach cancer, lung cancer, breast cancer, head and neck cancer, ovarian cancer, thyroid cancer, kidney cancer, bladder cancer, cervical cancer, pancreatic cancer, liposarcoma, testicular nonseminomatous germ cell cancer, melanoma, adenoma of the adrenal gland, schwannoma, malignant fibrous histiocytoma, or esophageal cancer.

10. The method of claim 1, wherein the anti-GPC3 chimeric antigen receptor comprises an antigen binding unit that exhibits specific binding to C-terminus of GPC3.

11. The method of claim 10, wherein the antigen binding unit comprises a sequence selected from the group consisting of SEQ ID NO: 1, SEQ ID NO: 2, SEQ ID NO: 3, SEQ ID NO:4, SEQ ID NO: 5, SEQ ID NO: 6, SEQ ID NO: 7, or SEQ ID NO: 8.

12. The method of claim 1, wherein the anti-GPC3-CAR comprises a sequence selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO: 30.

13. The method of claim 1, wherein the anti-GPC3-CAR comprises a sequence selected from the group consisting of SEQ ID NO 28, SEQ ID NO:29 or SEQ ID NO 30.

14. The method of claim 2, wherein the anti-GPC3-CAR T cells comprise at least two intracellular signaling domains.

15. The method of claim 2, wherein the anti-GPC3-CAR T cells comprise at least three intracellular signaling domains.

16. The method of claim 14, wherein the intracellular signaling domains are selected from a signaling domain derived from CD3, CD28, 4-1BB, OX40, DAP10, or ICOS.

17. The method of claim 1, wherein the lymphocyte reduction treatment comprises reducing a quantity of regulatory T cells in the subject.

18. The method of claim 17, wherein the reducing the quantity of regulatory T cells comprises a reduction of at least about 30% of the regulatory T cells as measured by flow cytometric analysis of circulating CD4$^+$ and CD25$^+$ cells in the subject.

19. The method of claim 1, wherein the lymphocyte reduction treatment further comprises administering radiation or a biological agent to the subject.

20. The method of claim 1, wherein the lymphocyte reduction treatment further comprises administering another chemotherapy to the subject.

21. The method of claim 20, wherein the administering another chemotherapy to the subject comprises administering a chemotherapeutic agent selected from the group consisting of etoposide, cytarabine, methotrexate, vincristine adriamycin, and any combination thereof.

22. The method of claim 21, wherein the chemotherapeutic agent is administered to the subject at least one time prior to administration of the anti-GPC3-CAR T cells.

23. The method of claim 1, wherein the lymphocyte reduction treatment reduces a quantity of lymphocytes by at least about 20% as measured by complete blood count (CBC) analysis.

24. The method of claim 2, further comprising a second administration of the anti-GPC3-CAR T cells to the subject.

25. The method of claim 1, wherein the subject has refractory, persistent, or progressive disease.

26. The method of claim 2, wherein the anti-GPC3-CAR T cells are autologous or allogenic to the subject.

27. The method of claim 1, further comprising administering at least one immunostimulatory agent to the subject concurrent or after administration of the anti-GPC3 chimeric antigen receptor immunoresponsive cells.

28. The method of claim 27, wherein the immunostimulatory agent is selected from the group consisting of aldesleukin (IL-2), IL-3, IL-6, IL-11, GM-CSF, and any combination thereof.

29. The method of claim 19, wherein the biological agent is an antibody directed to an antigen expressed on a lymphocyte.

* * * * *

SEQUENCE LISTING

<160> NUMBER OF SEQ ID NOS: 41

<210> SEQ ID NO 1
<211> LENGTH: 247
<212> TYPE: PRT
<213> ORGANISM: Unknown
<220> FEATURE:
<223> OTHER INFORMATION: Description of Unknown:
      Anti-GPC3 extracellular antigen binding region

<400> SEQUENCE: 1

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205
```

```
Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly
            245

<210> SEQ ID NO 2
<211> LENGTH: 247
<212> TYPE: PRT
<213> ORGANISM: Unknown
<220> FEATURE:
<223> OTHER INFORMATION: Description of Unknown:
      Anti-GPC3 extracellular antigen binding region

<400> SEQUENCE: 2

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Ala Ile Ser Met Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly
            245

<210> SEQ ID NO 3
<211> LENGTH: 247
<212> TYPE: PRT
<213> ORGANISM: Unknown
<220> FEATURE:
<223> OTHER INFORMATION: Description of Unknown:
      Anti-GPC3 extracellular antigen binding region
```

```
<400> SEQUENCE: 3

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
                100                 105                 110

Gln Gly Thr Leu Val Thr Val Ser Ser Gly Gly Gly Ser Gly Gly
            115                 120                 125

Gly Gly Ser Gly Gly Gly Gly Ser Gln Ser Ala Leu Thr Gln Pro Pro
130                 135                 140

Ser Ala Ser Gly Ser Pro Gly Gln Ser Val Thr Ile Ser Cys Thr Gly
145                 150                 155                 160

Thr Ser Ser Asp Val Gly His Lys Phe Pro Val Ser Trp Tyr Gln Gln
                165                 170                 175

Tyr Pro Gly Lys Ala Pro Lys Leu Leu Ile Tyr Lys Asn Leu Leu Arg
            180                 185                 190

Pro Ser Gly Val Pro Asp Arg Phe Ser Gly Ser Lys Ser Gly Thr Ser
            195                 200                 205

Ala Ser Leu Ala Ile Thr Gly Leu Gln Ala Glu Asp Gly Ala Asp Tyr
210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245

<210> SEQ ID NO 4
<211> LENGTH: 243
<212> TYPE: PRT
<213> ORGANISM: Unknown
<220> FEATURE:
<223> OTHER INFORMATION: Description of Unknown:
      Anti-GPC3 extracellular antigen binding region

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Ser Gly Gly Gly
        115                 120                 125

Gly Ser Asp Ile Val Met Thr Gln Thr Pro Leu Ser Leu Pro Val Thr
130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
210                 215                 220

Gln Ser Ile Tyr Val Pro Tyr Thr Phe Gly Gln Gly Thr Lys Leu Glu
225                 230                 235                 240

Ile Lys Arg

<210> SEQ ID NO 5
<211> LENGTH: 247
<212> TYPE: PRT
<213> ORGANISM: Unknown
<220> FEATURE:
<223> OTHER INFORMATION: Description of Unknown:
      Anti-GPC3 extracellular antigen binding region

<400> SEQUENCE: 5

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Thr Trp Val Arg Gln Ala Pro Gly Lys Gly Leu Glu Trp Val
        35                  40                  45

Ser Ser Ile Ser Ser Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
        210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245

<210> SEQ ID NO 6
<211> LENGTH: 247
<212> TYPE: PRT
<213> ORGANISM: Unknown
<220> FEATURE:
<223> OTHER INFORMATION: Description of Unknown:
      Anti-GPC3 extracellular antigen binding region

<400> SEQUENCE: 6

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Ala Pro Gly Lys Gly Leu Glu Trp Val
        35                  40                  45

Ser Glu Ile Ser Ser Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245

<210> SEQ ID NO 7
<211> LENGTH: 247
<212> TYPE: PRT
<213> ORGANISM: Unknown
<220> FEATURE:
<223> OTHER INFORMATION: Description of Unknown:
      Anti-GPC3 extracellular antigen binding region

<400> SEQUENCE: 7

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Leu Met His Asn Val Ser Trp Tyr Gln Gln
                165                 170                 175

Tyr Pro Gly Lys Ala Pro Lys Leu Leu Ile Tyr Lys Ser Ser Arg
            180                 185                 190

Pro Ser Gly Val Pro Asp Arg Phe Ser Gly Ser Lys Ser Gly Thr Ser
    195                 200                 205

Ala Ser Leu Ala Ile Thr Gly Leu Gln Ala Glu Asp Gly Ala Asp Tyr
210                 215                 220

Tyr Cys Gln Ser Tyr Asp Ser Ser Leu Arg Val Val Phe Gly Gly Gly
225                 230                 235                 240

Thr Lys Val Thr Val Leu Gly
                245
```

<210> SEQ ID NO 8
<211> LENGTH: 243
<212> TYPE: PRT
<213> ORGANISM: Unknown
<220> FEATURE:
<223> OTHER INFORMATION: Description of Unknown: Anti-GPC3 extracellular antigen binding region

<400> SEQUENCE: 8

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95
```

Thr His Val Pro Pro Thr Phe Gly Gln Gly Thr Lys Leu Glu Ile Lys
                100                 105                 110

Arg Gly Gly Gly Ser Gly Gly Gly Ser Gly Gly Gly Ser
        115                 120                 125

Gln Val Gln Leu Val Gln Ser Gly Ala Glu Val Lys Lys Pro Gly Ala
130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
210                 215                 220

Thr Arg Phe Tyr Ser Tyr Thr Tyr Trp Gly Gln Gly Thr Leu Val Thr
225                 230                 235                 240

Val Ser Ser

<210> SEQ ID NO 9
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 11
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 13
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 14
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Gly Gly Leu Val Gln Pro Gly Arg
1               5                   10                  15

```
Ser Leu Arg Leu Ser Cys Ala Ala Ser Gly Phe Thr Phe Ser Ser Tyr
         20                  25                  30

Ala Met His Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Arg Gly Ser His Ala Asp Ala Phe Asp Val Trp Gly
                100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
        210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
        290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
        370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430
```

```
Ser Glu Ile Gly Met Lys Gly Glu Arg Arg Gly Lys Gly His Asp
            435                 440                 445

Gly Leu Tyr Gln Gly Leu Ser Thr Ala Thr Lys Asp Thr Tyr Asp Ala
450                 455                 460

Leu His Met Gln Ala Leu Pro Pro Arg
465                 470

<210> SEQ ID NO 15
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320
```

```
Ser Lys Arg Ser Arg Leu Leu His Ser Asp Tyr Met Asn Met Thr Pro
            325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
            355                 360                 365

Tyr Ile Phe Lys Gln Pro Phe Met Arg Pro Val Gln Thr Thr Gln Glu
        370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
        450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 16
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Thr Trp Val Arg Gln Ala Pro Gly Lys Gly Leu Glu Trp Val
        35                  40                  45

Ser Ser Ile Ser Ser Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Arg Arg Gly Ser His Ala Asp Ala Phe Asp Val Trp Gly
        100                 105                 110

Gln Gly Thr Leu Val Thr Val Ser Ser Gly Gly Gly Ser Gly Gly
        115                 120                 125

Gly Gly Ser Gly Gly Gly Gly Ser Gln Ser Ala Leu Thr Gln Pro Pro
        130                 135                 140
```

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 17
<211> LENGTH: 473
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 17

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Thr Trp Val Arg Gln Ala Pro Gly Lys Gly Leu Glu Trp Val
        35                  40                  45

Ser Ser Ile Ser Ser Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400
```

```
Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470
```

<210> SEQ ID NO 18
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Ala Pro Gly Lys Gly Leu Glu Trp Val
        35                  40                  45

Ser Glu Ile Ser Ser Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270
```

```
Ala Cys Arg Pro Ala Ala Gly Gly Ala Val His Thr Arg Gly Leu Asp
            275                 280                 285

Phe Ala Cys Asp Phe Trp Val Leu Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
            325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
            355                 360                 365

Tyr Ile Phe Lys Gln Pro Phe Met Arg Pro Val Gln Thr Thr Gln Glu
            370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
            435                 440                 445

Gly Lys Pro Gln Arg Arg Lys Asn Pro Gln Glu Gly Leu Tyr Asn Glu
            450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 19
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Ala Pro Gly Lys Gly Leu Glu Trp Val
        35                  40                  45

Ser Glu Ile Ser Ser Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Asp Arg Arg Gly Ser His Ala Asp Ala Phe Asp Val Trp Gly
            100                 105                 110

Gln Gly Thr Leu Val Thr Val Ser Gly Gly Gly Ser Gly Gly
            115                 120                 125

Gly Gly Ser Gly Gly Gly Ser Gln Ser Ala Leu Thr Gln Pro Pro
130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
            195                 200                 205

Ala Ser Leu Ala Ile Thr Gly Leu Gln Ala Glu Asp Gly Ala Asp Tyr
            210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Phe Trp Val Leu Val Val Val Gly Gly Val Leu Ala
290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
            355                 360                 365

Asp Ala Pro Ala Tyr Gln Gln Gly Gln Asn Gln Leu Tyr Asn Glu Leu
            370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
            405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
            450                 455                 460

Leu His Met Gln Ala Leu Pro Pro Arg
465                 470

<210> SEQ ID NO 20
<211> LENGTH: 515
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 20

```
Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Ala Ile Ser Met Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400
```

```
Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 21
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Ala Ile Ser Met Ser Gly Glu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Gly Tyr Asn Tyr Val Ser Trp Tyr Gln Gln
                165                 170                 175

Tyr Pro Gly Lys Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220
```

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
            245                 250                 255

Thr Pro Ala Pro Thr Ile Ala Ser Gln Pro Leu Ser Leu Arg Pro Glu
        260                 265                 270

Ala Cys Arg Pro Ala Ala Gly Gly Ala Val His Thr Arg Gly Leu Asp
    275                 280                 285

Phe Ala Cys Asp Phe Trp Val Leu Val Val Gly Gly Val Leu Ala
290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
            325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
            405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470

<210> SEQ ID NO 22
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Arg Arg Gly Ser His Ala Asp Ala Phe Asp Val Trp Gly
            100                 105                 110

Gln Gly Thr Leu Val Thr Val Ser Gly Gly Gly Ser Gly Gly
        115                 120                 125

Gly Gly Ser Gly Gly Gly Gly Ser Gln Ser Ala Leu Thr Gln Pro Pro
        130                 135                 140

Ser Ala Ser Gly Ser Pro Gly Gln Ser Val Thr Ile Ser Cys Thr Gly
145                 150                 155                 160

Thr Ser Ser Asp Val Gly His Lys Phe Pro Val Ser Trp Tyr Gln Gln
                165                 170                 175

Tyr Pro Gly Lys Ala Pro Lys Leu Leu Ile Tyr Lys Asn Leu Leu Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
        435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510
```

Pro Pro Arg
    515

<210> SEQ ID NO 23
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly His Lys Phe Pro Val Ser Trp Tyr Gln Gln
                165                 170                 175

Tyr Pro Gly Lys Ala Pro Lys Leu Leu Ile Tyr Lys Asn Leu Leu Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

```
Arg Asp Phe Ala Ala Tyr Arg Ser Arg Val Lys Phe Ser Arg Ser Ala
            355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
                435                 440                 445

Gly Leu Tyr Gln Gly Leu Ser Thr Ala Thr Lys Asp Thr Tyr Asp Ala
            450                 455                 460

Leu His Met Gln Ala Leu Pro Pro Arg
465                 470

<210> SEQ ID NO 24
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Arg Arg Gly Ser His Ala Asp Ala Phe Asp Val Trp Gly
        100                 105                 110

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Pro
130                 135                 140

Ser Ala Ser Gly Ser Pro Gly Gln Ser Val Thr Ile Ser Cys Thr Gly
145                 150                 155                 160

Thr Ser Ser Asp Val Gly Leu Met His Asn Val Ser Trp Tyr Gln Gln
            165                 170                 175

Tyr Pro Gly Lys Ala Pro Lys Leu Leu Ile Tyr Lys Ser Ser Ser Arg
        180                 185                 190

Pro Ser Gly Val Pro Asp Arg Phe Ser Gly Ser Lys Ser Gly Thr Ser
    195                 200                 205

Ala Ser Leu Ala Ile Thr Gly Leu Gln Ala Glu Asp Gly Ala Asp Tyr
210                 215                 220
```

```
Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
            245                 250                 255

Thr Pro Ala Pro Thr Ile Ala Ser Gln Pro Leu Ser Leu Arg Pro Glu
        260                 265                 270

Ala Cys Arg Pro Ala Ala Gly Gly Ala Val His Thr Arg Gly Leu Asp
    275                 280                 285

Phe Ala Cys Asp Phe Trp Val Leu Val Val Gly Gly Val Leu Ala
290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
            325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Arg Gly Arg Lys Lys Leu Leu
        355                 360                 365

Tyr Ile Phe Lys Gln Pro Phe Met Arg Pro Val Gln Thr Thr Gln Glu
370                 375                 380

Glu Asp Gly Cys Ser Cys Arg Phe Pro Glu Glu Glu Glu Gly Gly Cys
385                 390                 395                 400

Glu Leu Arg Val Lys Phe Ser Arg Ser Ala Asp Ala Pro Ala Tyr Gln
            405                 410                 415

Gln Gly Gln Asn Gln Leu Tyr Asn Glu Leu Asn Leu Gly Arg Arg Glu
        420                 425                 430

Glu Tyr Asp Val Leu Asp Lys Arg Arg Gly Arg Asp Pro Glu Met Gly
    435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
            485                 490                 495

Ser Thr Ala Thr Lys Asp Thr Tyr Asp Ala Leu His Met Gln Ala Leu
            500                 505                 510

Pro Pro Arg
        515

<210> SEQ ID NO 25
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45
```

```
Ser Ala Ile Ser Ser Ser Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Arg Gly Ser His Ala Asp Ala Phe Asp Val Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Gln Ser Ala Leu Thr Gln Pro Pro
    130                 135                 140

Ser Ala Ser Gly Ser Pro Gly Gln Ser Val Thr Ile Ser Cys Thr Gly
145                 150                 155                 160

Thr Ser Ser Asp Val Gly Leu Met His Asn Val Ser Trp Tyr Gln Gln
            165                 170                 175

Tyr Pro Gly Lys Ala Pro Lys Leu Leu Ile Tyr Lys Ser Ser Ser Arg
            180                 185                 190

Pro Ser Gly Val Pro Asp Arg Phe Ser Gly Ser Lys Ser Gly Thr Ser
    195                 200                 205

Ala Ser Leu Ala Ile Thr Gly Leu Gln Ala Glu Asp Gly Ala Asp Tyr
    210                 215                 220

Tyr Cys Gln Ser Tyr Asp Ser Ser Leu Arg Val Val Phe Gly Gly Gly
225                 230                 235                 240

Thr Lys Val Thr Val Leu Gly Thr Thr Thr Pro Ala Pro Arg Pro Pro
            245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
            275                 280                 285

Phe Ala Cys Asp Phe Trp Val Leu Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Arg Val Lys Phe Ser Arg Ser Ala
            355                 360                 365

Asp Ala Pro Ala Tyr Gln Gln Gly Gln Asn Gln Leu Tyr Asn Glu Leu
            370                 375                 380

Asn Leu Gly Arg Arg Glu Glu Tyr Asp Val Leu Asp Lys Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
    450                 455                 460
```

Leu His Met Gln Ala Leu Pro Pro Arg
465                 470

<210> SEQ ID NO 26
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

```
Ala Tyr Arg Ser Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 27
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220
```

-continued

Thr Arg Phe Tyr Ser Tyr Thr Tyr Trp Gly Gln Gly Thr Leu Val Thr
225                 230                 235                 240

Val Ser Ser Thr Thr Thr Pro Ala Pro Arg Pro Pro Thr Pro Ala Pro
            245                 250                 255

Thr Ile Ala Ser Gln Pro Leu Ser Leu Arg Pro Glu Ala Cys Arg Pro
        260                 265                 270

Ala Ala Gly Gly Ala Val His Thr Arg Gly Leu Asp Phe Ala Cys Asp
    275                 280                 285

Phe Trp Val Leu Val Val Val Gly Val Leu Ala Cys Tyr Ser Leu
290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510

<210> SEQ ID NO 28
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Tyr Ser Tyr Ala Tyr Trp Gly Gln Gly Thr Leu Val Thr
            100                 105                 110

Val Ser Ala Gly Gly Gly Ser Gly Gly Gly Ser Gly Gly Gly
        115                 120                 125

Gly Ser Asp Ile Val Met Thr Gln Thr Pro Leu Ser Leu Pro Val Thr
130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
            165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
            195                 200                 205

Lys Ile Ser Arg Val Glu Ala Glu Asp Val Gly Val Tyr Tyr Cys Ser
210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
            275                 280                 285

Phe Trp Val Leu Val Val Val Gly Gly Val Leu Ala Cys Tyr Ser Leu
290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
            325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
            370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
            450                 455                 460

Ala Leu Pro Pro Arg
465
```

<210> SEQ ID NO 29
<211> LENGTH: 466
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Ser Gly Gly Gly
            115                 120                 125

Gly Ser Asp Ile Val Met Thr Gln Thr Pro Leu Ser Leu Pro Val Thr
    130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Ser Gly Thr Asp Phe Thr Leu
        195                 200                 205

Lys Ile Ser Arg Val Glu Ala Glu Asp Val Gly Val Tyr Tyr Cys Ser
    210                 215                 220

Gln Ser Ile Tyr Val Pro Tyr Thr Phe Gly Gln Gly Thr Lys Leu Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Lys
        355                 360                 365
```

```
Gln Gly Gln Asn Gln Leu Tyr Asn Glu Leu Asn Leu Gly Arg Arg Glu
        370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 30
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Ala Ile His Pro Gly Ser Gly Asp Thr Ala Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Asp Ile Val Met Thr Gln Thr Pro Leu Ser Leu Pro Val Thr
    130                 135                 140

Pro Gly Glu Pro Ala Ser Ile Ser Cys Arg Ser Ser Gln Ser Leu Val
145                 150                 155                 160

His Ser Asn Gly Asn Thr Tyr Leu Gln Trp Tyr Leu Gln Lys Pro Gly
                165                 170                 175

Gln Ser Pro Gln Leu Leu Ile Tyr Lys Val Ser Asn Arg Phe Ser Gly
            180                 185                 190

Val Pro Asp Arg Phe Ser Gly Ser Gly Thr Asp Phe Thr Leu
            195                 200                 205

Lys Ile Ser Arg Val Glu Ala Glu Asp Val Gly Val Tyr Tyr Cys Ser
    210                 215                 220

Gln Ser Ile Tyr Val Pro Tyr Thr Phe Gly Gln Gly Thr Lys Leu Glu
225                 230                 235                 240
```

```
Ile Lys Arg Thr Thr Thr Pro Ala Pro Arg Pro Pro Thr Pro Ala Pro
            245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
            275                 280                 285

Phe Trp Val Leu Val Val Gly Gly Val Leu Ala Cys Tyr Ser Leu
290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
            325                 330                 335

Pro Thr Arg Lys His Tyr Gln Pro Tyr Ala Pro Pro Arg Asp Phe Ala
            340                 345                 350

Ala Tyr Arg Ser Lys Arg Gly Arg Lys Lys Leu Leu Tyr Ile Phe Lys
            355                 360                 365

Gln Pro Phe Met Arg Pro Val Gln Thr Thr Gln Glu Glu Asp Gly Cys
            370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
            405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
            435                 440                 445

Arg Arg Lys Asn Pro Gln Glu Gly Leu Tyr Asn Glu Leu Gln Lys Asp
450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
            485                 490                 495

Lys Asp Thr Tyr Asp Ala Leu His Met Gln Ala Leu Pro Pro Arg
            500                 505                 510
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31 gcagggggaaa gaatagtaga ca                                             22

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cggcctggcg gcgtggag                                                   18

```
<210> SEQ ID NO 33
<211> LENGTH: 442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gcaggggaaa gaatagtaga cataatagca acagacatac aaactaaaga attacaaaaa     60
caaattacaa aaattcaaaa tttttatcgat ggctccggtg cccgtcagtg ggcagagcgc   120
acatcgccca cagtccccga gaagttgggg ggaggggtcg gcaattgaac cggtgcctag   180
agaaggtggc gcggggtaaa ctgggaaagt gatgtcgtgt actggctccg ccttttttccc  240 gagggtgggg gagaaccgta tataagtgca gtagtcgccg tgaacgttct ttttcgcaac   300
gggtttgccg ccagaacaca ggtgtcgtga cgcggatcca ggcctaagct tacgcgtcct   360
agcgctaccg gtcgccacca tggccttacc agtgaccgcc ttgctcctgc cgctggcctt   420
gctgctccac gccgccaggc cg                                            442

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctccacgccg ccaggccgga ggtgcagctg gtgcag                              36

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcggtgtcct cgctccgcag gctgctcagc tccatgtagg cggtg                    45

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcggagcgag gacaccgccg tgtactactg cgcccggttc tacagctac                49

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cggcgctggc gtcgtggtac gtttgatctc cagcttggtg                          40
```

-continued

```
<210> SEQ ID NO 38
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ctccacgccg ccaggccgga ggtgcagctg gtgcagagcg gcgccgaggt gaagaagccc      60
ggcgccagcg tgaaggtgag ctgcaaggcc agcggctaca ccttcagcga ctacgagatg     120
cactgggtgc ggcaggcccc cggccagggc ctggagtgga tgggcgccat ccacccggc      180 agcggcgaca ccgcctacaa ccagcggttc aagggccggg tgaccatcac cgccgacaag     240
agcaccagca ccgcctacat ggagctgagc agcctgcgga gcgaggacac cgccgtgtac     300
tactgcgccc ggttctacag ctacgcctac tggggccagg gcaccctggt gaccgtgagc     360
gccggtggag gcggttcagg cggaggtggt tctggcggtg gcggatcgga catcgtgatg     420
acccagaccc ccctgagcct gcccgtgacc cccggcgagc cgccagcat cagctgccgg      480 agcagccaga gcctggtgca cagcaacggc aacacctacc tgcagtggta cctgcagaag     540
cccggccaga gcccccagct gctgatctac aaggtgagca ccggttcag cggcgtgccc      600 gaccggttca gcggcagcgg cagcggcacc gacttcaccc tgaagatcag ccgggtggag     660
gccgaggacg tgggcgtgta ctactgcagc cagagcatct acgtgcccta caccttcggc     720
cagggcacca gctggagat caaacgtacc acgacgccag cgccg                      765

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
accacgacgc cagcgccg                                                    18

<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aatccagagg ttgattgtcg acctagcgag ggggcagggc ctgc                       44

<210> SEQ ID NO 41
<211> LENGTH: 703
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
accacgacgc cagcgccgcg accaccaaca ccggcgccca ccatcgcgtc gcagcccctg      60
tccctgcgcc cagaggcgtg ccggccagcg gcgggggggcg cagtgcacac gagggggctg    120
gacttcgcct gtgattttg ggtgctggtg gtggttggtg gagtcctggc ttgctatagc      180
```

-continued

```
ttgctagtaa cagtggcctt tattattttc tgggtgagga gtaagaggag caggctcctg    240
cacagtgact acatgaacat gactccccgc cgccccgggc caacccgcaa gcattaccag    300
ccctatgccc caccacgcga cttcgcagcc tatcgctcca gagtgaagtt cagcaggagc    360
gcagacgccc ccgcgtacca gcagggccag aaccagctct ataacgagct caatctagga    420
cgaagagagg agtacgatgt tttggacaag agacgtggcc gggaccctga gatggggga    480 aagccgcaga gaaggaagaa ccctcaggaa ggcctgtaca atgaactgca gaaagataag    540
atggcggagg cctacagtga gattgggatg aaaggcgagc gccggagggg caagggcac    600 gatggccttt accagggtct cagtacagcc accaaggaca cctacgacgc ccttcacatg    660
caggccctgc cccctcgcta ggtcgacaat caacctctgg att                      703
```